US008795658B2

(12) United States Patent
Butterweck et al.

(10) Patent No.: US 8,795,658 B2
(45) Date of Patent: Aug. 5, 2014

(54) STABILIZATION OF IMMUNOGLOBULINS THROUGH AQUEOUS FORMULATION WITH HISTIDINE AT WEAK ACIDIC TO NEUTRAL PH

(75) Inventors: Harald Arno Butterweck, Vienna (AT); Bernhard Kölbl, Achau (AT); Lucia Hofbauer, Eggenburg (AT); Wolfgang Teschner, Vienna (AT); Hans-Peter Schwarz, Vienna (AT)

(73) Assignees: Baxter International Inc., Deerfield, IL (US); Baxter Healthcare SA, Glattpark (Opfikon)

( * ) Notice: Subject to any disclaimer, the term of this patent is extended or adjusted under 35 U.S.C. 154(b) by 87 days.

(21) Appl. No.: 13/235,314

(22) Filed: Sep. 16, 2011

(65) Prior Publication Data

US 2012/0076772 A1    Mar. 29, 2012

Related U.S. Application Data

(60) Provisional application No. 61/384,209, filed on Sep. 17, 2010.

(51) Int. Cl.
*A61K 39/395* (2006.01)
*A61K 47/02* (2006.01)
*A61K 47/18* (2006.01)
*A61K 9/00* (2006.01)

(52) U.S. Cl.
CPC .............. *A61K 9/0019* (2013.01); *A61K 47/02* (2013.01); *A61K 47/183* (2013.01)
USPC .................... 424/130.1; 424/133.1; 424/134.1

(58) Field of Classification Search
None
See application file for complete search history.

(56) References Cited

U.S. PATENT DOCUMENTS

| 4,597,966 A | 7/1986 | Zolton et al. |
| 5,763,394 A | 6/1998 | O'Connor et al. |
| 5,871,736 A | 2/1999 | Bruegger et al. |
| 6,252,055 B1 | 6/2001 | Relton |
| 6,267,958 B1 | 7/2001 | Andya et al. |
| 7,060,268 B2 | 6/2006 | Andya et al. |
| 2005/0276823 A1 | 12/2005 | Cini et al. |
| 2006/0088523 A1 | 4/2006 | Andya et al. |
| 2007/0172475 A1 | 7/2007 | Matheus et al. |
| 2008/0071063 A1 | 3/2008 | Allan et al. |
| 2010/0015157 A1 | 1/2010 | Andya et al. |

FOREIGN PATENT DOCUMENTS

| EP | 1 029 548 A1 | 8/2000 |
| WO | WO 00/56772 A1 | 9/2000 |
| WO | WO 03/039485 A2 | 5/2003 |
| WO | WO 03/039485 A3 | 5/2003 |
| WO | WO 2006/083889 A2 | 8/2006 |
| WO | WO 2007/019232 A2 | 2/2007 |
| WO | WO 2009/009406 A1 | 1/2009 |
| WO | WO 2010/062896 A1 | 6/2010 |
| WO | WO 2011/028961 A2 | 3/2011 |
| WO | WO 2012/037530 A1 | 3/2012 |
| WO | WO 2012/037534 A1 | 3/2012 |

OTHER PUBLICATIONS

Gaines, A. et al., "Renal insufficiency and Failure Associated with Immune Globulin Intravenous Therapy—United States, 1985-1998," *MMWR Weekly*, Jun. 25, 1999, vol. 46, No. 24, pp. 518-521, located at <<http://www.cdc.gov/mmwr/preview/mmwrhtml/mm4824a3.htm>>, 3 pages.
International Search Report mailed on Feb. 6, 2012, for International Patent Application No. PCT/US2011/052053, filed Sep. 16, 2011, 5 pages.
Kwan, T.H. et al., "Acute renal failure related to intravenous immunoglobulin infusion in an elderly woman," *Hong Kong Med J.*, Feb. 2005, vol. 11, No. 1, pp. 45-49.
Wang, W. et al., "Antibody Structure, Instability and Formulation," *Journal of Pharmaceutical Sciences*, Jan. 2007, vol. 96, No. 1, pp. 1-26.
Cordoba, A.J., et al., "Non-Enzymatic hinge region fragmentation of antibodies in solution," *Journal of Chromatography B*, 2005, vol. 818, pp. 115-121.

*Primary Examiner* — Yunsoo Kim
(74) *Attorney, Agent, or Firm* — Morgan, Lewis & Bockius LLP

(57) ABSTRACT

The present invention provides, among other aspects, storage stabile aqueous formulations of immunoglobulins with histidine at a mildly acidic to neutral pH. The present invention also provides methods for stabilizing immunoglobulin compositions by formulating with histidine at a mildly acidic to neutral pH. Advantageously, the methods and formulations provided herein allow stabile aqueous compositions of immunoglobulins at mildly acidic to neutral pH useful for parenteral administration.

34 Claims, 5 Drawing Sheets

STABILIZATION OF IMMUNOGLOBULINS THROUGH AQUEOUS FORMULATION WITH HISTIDINE AT WEAK ACIDIC TO NEUTRAL PH

CROSS-REFERENCES TO RELATED APPLICATIONS

The present application claims the benefit of U.S. Provisional Application No. 61/384,209, filed Sep. 17, 2010, the content of which is expressly incorporated herein by reference in its entirety for all purposes.

BACKGROUND OF THE INVENTION

Biologics are medicinal products created by biological processes, including preparations isolated from natural sources (e.g., human plasma) and recombinant DNA technologies. Within the healthcare and pharmaceutical industries, biologics are becoming increasingly important for patient treatment and overall revenue growth (Goodman M. Nat Rev Drug Discov. (2009) November; 8(11):837). One important class of biologic drugs is therapeutic proteins, both isolated from natural sources and recombinantly produced. For example, plasma proteins are manufactured for therapeutic administration by isolation from pooled human plasma (e.g., GAMMAGARD LIQUID® [IVIG, Immune Globulin Intravenous (Human) 10%]; Baxter International, Deerfield, Ill.) and recombinant means (e.g., ADVATE® [Antihemophilic Factor (Recombinant), Plasma/Albumin-Free Method]; Baxter International, Deerfield, Ill.).

The administration of therapeutic proteins are primarily performed by intravenous (IV), subcutaneous (SQ), and intramuscular administration, although other routes of administration may be used depending upon the therapeutic protein and condition being treated. Most of the immunoglobulins are administered intravenously as larger volumes can be delivered rapidly by the intravenous route to provide the physiologic levels of IgG needed for the effective treatment of various diseases, such as primary immune deficiencies (PID), immune (idiopathic) thrombocytopenic purpura (ITP) and the Kawasaki syndrome. Due to the nature of IV administration, therapy via this route is a slow and timely process, leading to problems with patient compliance.

Subcutaneous (SQ) administration of therapeutic proteins is an alternative to intravenous administration. Compared to IV infusions, SQ administration has several advantages. For example, it can reduce the incidence of systemic reactions, it does not require sometimes-difficult IV access, and gives patients more independence.

In order to improve patient compliance, it would be convenient to provide the protein in a liquid ready to use formulation. However, many human or humanized therapeutic proteins are unstable when formulated at or near neutral pH. A variety of degradation pathways exist for proteins especially in liquid formulations, implicating both chemical and physical instability. Chemical instability includes deamination, aggregation, clipping of the peptide backbone, and oxidation of methionine residues. Physical instability encompasses many phenomena, including, for example, aggregation. Protein instability is particularly problematic for labile proteins that are unstable at mildly acidic to neutral pH. To combat these issues, intravenously administrable immunoglobulins have been formulated at acidic pH, effectively increasing their stability in the formulation (products that are formulated at acidic pH are, e.g., Gamunex (Talecris), Gammagard Liquid (Baxter) or Privigen (CSL).

To combat these issues, therapeutic protein compositions are often formulated at acidic pH, effectively increasing their stability in the formulation. Unfortunately, scientific publications have reported that, for example, intramuscular administration of acidic aqueous preparations can cause pain, and potentially could result in tissue damage (Steen et al., 2001; Sluka et al., 2000, the disclosures of which are incorporated by reference herein in their entireties for all purposes). In other cases, where aqueous formulations have been found not to adequately stabilize the therapeutic proteins, lyophilized formulations are used which must be reconstituted prior to administration. In both cases, these factors can cause a less satisfactory drug administration experience and/or inconvenience for the patient, resulting in reduced patient compliance.

U.S. Pat. No. 6,267,958 describes the formulation of lyophilized monoclonal antibodies with low concentrations of histidine buffer (i.e., 5-10 mM) at pH 6.0 or 7.0 and a disaccharide (i.e., sucrose or trehalose) at a molar concentration that is 100 to 1500 times greater than the molar concentration of the monoclonal antibody. However, the monoclonal antibody formulations are unstable in the absence of the disaccharide, as evidenced by the high level of aggregate formation upon reconstitution when formulated with histidine alone.

U.S. Patent Application Publication No. 2010/0015157 describes the formulation of monoclonal antibodies with low concentrations of histidine acetate buffer (i.e., 10-20 mM) at pH 5.5 to 6.5 with non-ionic surfactants and/or disaccharides (i.e., sucrose or trehalose). However, the monoclonal antibody formulations are unstable in the absence of a non-ionic surfactants and/or disaccharides, as evidenced by the high turbidity and level of antibody aggregation seen in compositions formulated with histidine alone.

As such, there is a need in the art for formulations and methods of formulation that stabilize these labile therapeutic proteins in aqueous compositions at mildly acidic to neutral pH. The present invention satisfies these and other needs by, among other aspects, providing immunoglobulin compositions formulated with histidine at mild acidic to neutral pH that stabilize labile therapeutic proteins.

BRIEF SUMMARY OF INVENTION

The present invention is based in part by the surprising finding that the inclusion of histidine in an immunoglobulin composition formulated at mildly acidic to neutral pH significantly stabilizes the formulation.

Advantageously, the storage-stable aqueous immunoglobulin compositions provided herein remain stable for long periods at temperatures (e.g., for a year or longer) without the inclusion of additional excipients such as non-ionic surfactants and saccharides.

In contrast to previously described monoclonal antibody compositions, that are formulated using low concentrations of histidine (i.e., from 5 mM to 20 mM) at mildly acidic to neutral pH, the aqueous immunoglobulin compositions provided herein, which are formulated with moderate to high concentrations of histidine (i.e., from 50 mM to 500 mM), are stable at mildly acidic to neutral pH in the absence of surfactants (e.g., non-ionic surfactants such as polysorbate 80) and saccharides (e.g., disaccharides such as sucrose and trehalose). The use of fewer components for the formulation of immunoglobulins may be beneficial, as acute renal failure or insufficiency has been linked to the use of IVIG formulated with sucrose, maltose, and glucose (MMWR Morb Mortal Wkly Rep. 1999 Jun. 25; 48(24):518-21; Kwan et al. Hong Kong Med J. 2005 February; 11(1):45-9). Similarly, sever hypersensitivity reactions may occur in patients administered IVIG formulated with polysorbate 80. In fact, Hizentra® (Immune Globulin Subcutaneous (Human), 20% Liquid; CSL Behring AG, Bern, Switzerland) is contraindicated in patients who have had an anaphylactic or severe systemic reaction to the administration of human immune globulin or to components of Hizentra, such as polysorbate 80 (Hizentra Prescribing Information). Furthermore, the ability to stably formulate immunoglobulins at mildly acidic to neutral pH allows for the manufacture of pharmaceutical compositions that may be administered subcutaneously (SQ) or intramuscularly (IM) without the pain and potential for tissue damage that is associated with the SQ and IM administration of compositions formulated at acidic pH.

In one aspect, the present invention provides a storage stable, aqueous immunoglobulin composition comprising: (a) an immunoglobulin; (b) from 50 mM to 500 mM histidine; (c) from 0 mM to 10 mM of an alkali metal cation; and (d) a pH from 5.5 to 7.0.

In a specific embodiment of the storage stable, aqueous immunoglobulin compositions provided above, the composition contains from 150 mM to 350 mM histidine.

In a specific embodiment of the storage stable, aqueous immunoglobulin compositions provided above, the composition contains from 225 mM to 275 mM histidine.

In a specific embodiment of the storage stable, aqueous immunoglobulin compositions provided above, the composition contains from 0 mM to 1 mM of an alkali metal cation.

In a specific embodiment of the storage stable, aqueous immunoglobulin compositions provided above, the composition contains from 10 mM to 400 mM chloride ions.

In a specific embodiment of the storage stable, aqueous immunoglobulin compositions provided above, the composition contains from 100 mM to 200 mM chloride ions.

In a specific embodiment of the storage stable, aqueous immunoglobulin compositions provided above, the pH of the composition is from 5.5 to 6.5.

In a specific embodiment of the storage stable, aqueous immunoglobulin compositions provided above, the pH of the composition is 6.1±0.2.

In a specific embodiment of the storage stable, aqueous immunoglobulin compositions provided above, the composition further comprises an antioxidant.

In a specific embodiment of the storage stable, aqueous immunoglobulin compositions provided above, the composition does not contain a surfactant or sugar.

In a specific embodiment of the storage stable, aqueous immunoglobulin compositions provided above, the composition is stored under an inert gas.

In a specific embodiment of the storage stable, aqueous immunoglobulin compositions provided above, the composition is stored under an inert gas selected from the group consisting of nitrogen, argon, carbon dioxide, helium, krypton, and xenon.

In a specific embodiment of the storage stable, aqueous immunoglobulin compositions provided above, the composition is stored under nitrogen.

In a specific embodiment of the storage stable, aqueous immunoglobulin compositions provided above, the composition is stored under argon.

In a specific embodiment of the storage stable, aqueous immunoglobulin compositions provided above, the immunoglobulin is a polyclonal immunoglobulin.

In a specific embodiment of the storage stable, aqueous immunoglobulin compositions provided above, the immunoglobulin is a monoclonal immunoglobulin.

In a specific embodiment of the storage stable, aqueous immunoglobulin compositions provided above, the immunoglobulin is an IgG immunoglobulin.

In a specific embodiment of the storage stable, aqueous immunoglobulin compositions provided above, the immunoglobulin is enriched from pooled human plasma.

In a specific embodiment of the storage stable, aqueous immunoglobulin compositions provided above, the immunoglobulin is a recombinant immunoglobulin.

In a specific embodiment of the storage stable, aqueous immunoglobulin compositions provided above, the concentration of the immunoglobulin is 50±5 g/L.

In a specific embodiment of the storage stable, aqueous immunoglobulin compositions provided above, the concentration of the immunoglobulin is less than 50 g/L.

In a specific embodiment of the storage stable, aqueous immunoglobulin compositions provided above, the concentration of the immunoglobulin is at least 50 g/L.

In a specific embodiment of the storage stable, aqueous immunoglobulin compositions provided above, the concentration of the immunoglobulin is from 50 g/L to 150 g/L.

In a specific embodiment of the storage stable, aqueous immunoglobulin compositions provided above, the concentration of the immunoglobulin is 100±10 g/L.

In a specific embodiment of the storage stable, aqueous immunoglobulin compositions provided above, the concentration of the immunoglobulin is at least 100 g/L.

In a specific embodiment of the storage stable, aqueous immunoglobulin compositions provided above, the concentration of the immunoglobulin is 150±15 g/L.

In a specific embodiment of the storage stable, aqueous immunoglobulin compositions provided above, the concentration of the immunoglobulin is from 150 g/L to 250 g/L.

In a specific embodiment of the storage stable, aqueous immunoglobulin compositions provided above, the concentration of the immunoglobulin is 200±20 g/L.

In a specific embodiment of the storage stable, aqueous immunoglobulin compositions provided above, the concentration of the immunoglobulin is at least 200 g/L.

In a specific embodiment of the storage stable, aqueous immunoglobulin compositions provided above, the composition is stable for at least 1 month when stored at from 38° C. to 42° C.

In a specific embodiment of the storage stable, aqueous immunoglobulin compositions provided above, the composition is stable for at least 3 months when stored at from 38° C. to 42° C.

In a specific embodiment of the storage stable, aqueous immunoglobulin compositions provided above, the composition is stable for at least 6 months when stored at from 38° C. to 42° C.

In a specific embodiment of the storage stable, aqueous immunoglobulin compositions provided above, the composition is stable for at least 6 months when stored at from 28° C. to 32° C.

In a specific embodiment of the storage stable, aqueous immunoglobulin compositions provided above, the composition is stable for at least 1 year when stored at from 28° C. to 32° C.

In a specific embodiment of the storage stable, aqueous immunoglobulin compositions provided above, the composition is stable for at least 2 years when stored at from 28° C. to 32° C.

In a specific embodiment of the storage stable, aqueous immunoglobulin compositions provided above, the composition is considered stable as long as the percentage of immunoglobulin in the aggregated state remains below 2%.

In a specific embodiment of the storage stable, aqueous immunoglobulin compositions provided above, the composition is considered stable as long as the percentage of immunoglobulin in the aggregated state is from 0% to 2% and the percentage of immunoglobulin in the monomeric state is from 85% to 100%.

In a specific embodiment of the storage stable, aqueous immunoglobulin compositions provided above, a composition having the same components, but formulated at pH 4.8, is stable for less than 1 month when stored at from 38° C. to 42° C.

In a specific embodiment of the storage stable, aqueous immunoglobulin compositions provided above, a composition having the same components, but formulated at pH 4.8, is stable for less than 6 months when stored at from 28° C. to 32° C.

In one aspect, the present invention provides a method for stabilizing an immunoglobulin composition, the method comprising formulating the composition at a pH between 5.5 and 7.0, wherein the formulated composition comprises: (a) an immunoglobulin; (b) from 50 mM to 500 mM histidine; and (c) from 0 mM to 10 mM of an alkali metal cation.

In a specific embodiment of the methods provided above, the formulated composition contains from 150 mM to 350 mM histidine.

In a specific embodiment of the methods provided above, the formulated composition contains from 225 mM to 275 mM histidine.

In a specific embodiment of the methods provided above, the formulated composition contains from 0 mM to 1 mM of an alkali metal cation.

In a specific embodiment of the methods provided above, the formulated composition contains from 10 mM to 400 mM chloride ions.

In a specific embodiment of the methods provided above, the formulated composition contains from 100 mM to 200 mM chloride ions.

In a specific embodiment of the methods provided above, the pH of the formulated composition is from 5.5 to 6.5.

In a specific embodiment of the methods provided above, the pH of the formulated composition is 6.1±0.2.

In a specific embodiment of the methods provided above, the formulated composition further comprises an antioxidant.

In a specific embodiment of the methods provided above, the formulated composition does not contain a surfactant or sugar.

In a specific embodiment of the methods provided above, the formulated composition is stored under an inert gas.

In a specific embodiment of the methods provided above, the formulated composition is stored under an inert gas selected from the group consisting of nitrogen, argon, carbon dioxide, helium, krypton, and xenon.

In a specific embodiment of the methods provided above, the formulated composition is stored under nitrogen.

In a specific embodiment of the methods provided above, the formulated composition is stored under argon.

In a specific embodiment of the methods provided above, the immunoglobulin is a polyclonal immunoglobulin.

In a specific embodiment of the methods provided above, the immunoglobulin is a monoclonal immunoglobulin.

In a specific embodiment of the methods provided above, the immunoglobulin is an IgG immunoglobulin.

In a specific embodiment of the methods provided above, the immunoglobulin is enriched from pooled human plasma.

In a specific embodiment of the methods provided above, the immunoglobulin is a recombinant immunoglobulin.

In a specific embodiment of the methods provided above, the concentration of the immunoglobulin in the formulated composition is 50±5 g/L.

In a specific embodiment of the methods provided above, the concentration of the immunoglobulin in the formulated composition is less than 50 g/L.

In a specific embodiment of the methods provided above, the concentration of the immunoglobulin in the formulated composition is at least 50 g/L.

In a specific embodiment of the methods provided above, the concentration of the immunoglobulin in the formulated composition is from 50 g/L to 150 g/L.

In a specific embodiment of the methods provided above, the concentration of the immunoglobulin in the formulated composition is 100±10 g/L.

In a specific embodiment of the methods provided above, the concentration of the immunoglobulin in the formulated composition is at least 100 g/L.

In a specific embodiment of the methods provided above, the concentration of the immunoglobulin in the formulated composition is 150±15 g/L.

In a specific embodiment of the methods provided above, the concentration of the immunoglobulin in the formulated composition is from 150 g/L to 250 g/L.

In a specific embodiment of the methods provided above, the concentration of the immunoglobulin in the formulated composition is 200±20 g/L.

In a specific embodiment of the methods provided above, the concentration of the immunoglobulin in the formulated composition is at least 200 g/L.

In a specific embodiment of the methods provided above, the formulated composition is stable for at least 1 month when stored at from 38° C. to 42° C.

In a specific embodiment of the methods provided above, the formulated composition is stable for at least 3 months when stored at from 38° C. to 42° C.

In a specific embodiment of the methods provided above, the formulated composition is stable for at least 6 months when stored at from 38° C. to 42° C.

In a specific embodiment of the methods provided above, the formulated composition is stable for at least 6 months when stored at from 28° C. to 32° C.

In a specific embodiment of the methods provided above, the formulated composition is stable for at least 1 year when stored at from 28° C. to 32° C.

In a specific embodiment of the methods provided above, the formulated composition is stable for at least 2 years when stored at from 28° C. to 32° C.

In a specific embodiment of the methods provided above, the formulated composition is considered stable as long as the percentage of immunoglobulin in the aggregated state remains below 2%.

In a specific embodiment of the methods provided above, the formulated composition is considered stable as long as the percentage of immunoglobulin in the aggregated state is from 0% to 2% and the percentage of immunoglobulin in the monomeric state is from 85% to 100%.

In a specific embodiment of the methods provided above, an immunoglobulin composition having the same components as the formulated composition, but formulated at pH 4.8, is stable for less than 1 month when stored at from 38° C. to 42° C.

In a specific embodiment of the methods provided above, an immunoglobulin composition having the same components as the formulated composition, but formulated at pH 4.8, is stable for less than 6 months when stored at from 28° C. to 32° C.

DETAILED DESCRIPTION OF INVENTION

I. Introduction

Figure 1:
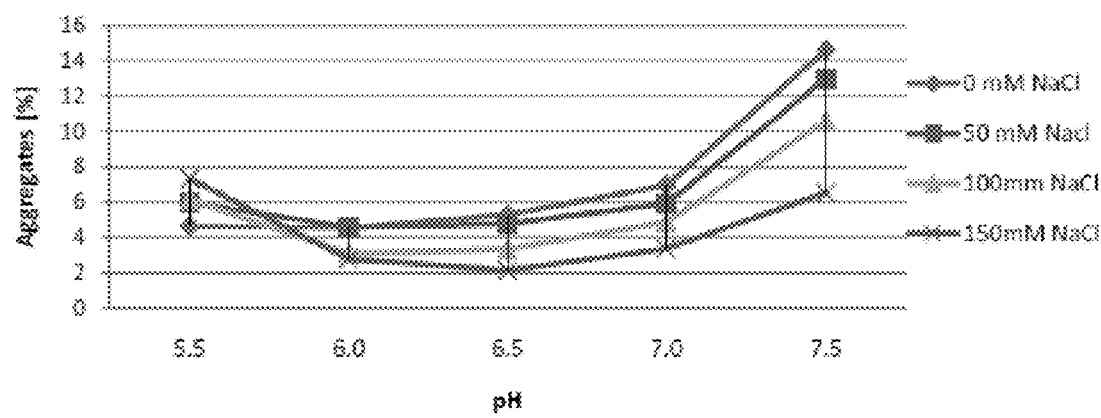
FIG. 1. Aggregation of 20% IgG formulations after 6 months storage at 38° C. to 42° C.

Therapeutic immunoglobulin preparations are often times formulated at acidic pH or as lyophilized compositions due to their labile nature in aqueous solution at or near neutral pH. As discussed above, these formulations are less convenient, may cause pain and/or tissue damage upon administration, and likely reduce patient compliance. Advantageously, the present invention provides means for stably formulating immunoglobulins in aqueous solution at or near neutral pH. In one aspect, the present invention provides immunoglobulin compositions stabilized by the addition of a moderate amount of histidine (e.g., 50 mM to 500 mM histidine, preferably 150 mM to 350 mM histidine) to formulations at mildly acidic to neutral pH (e.g., 5.5 to 7.0).

The present invention is based in part on the discovery that immunoglobulin compositions can be stabilized by the addition of moderate levels of histidine to formulations at mildly acidic to neutral pH in the absence of an alkali metal cation (e.g., $Na^+$ or $K^+$). Notably, the histidine formulations at mildly acidic to neutral pH provided herein are significantly more stable than similar compositions formulated at acidic pH, as well as immunoglobulin compositions formulated with proline or glycine at acidic pH. Advantageously, the ability to stably formulate immunoglobulins at mildly acidic to neutral pH provides for formulations that are not painful upon administration and do not have the same risks for tissue damage.

Our new studies provided herein demonstrate that purified plasma-derived immunoglobulin preparations formulated in 0.25 M glycine could be stabilized by the addition of sodium chloride in a pH dependent manner. Examples 1 and 2 shows that these immunoglobulin preparations, having a final concentration of between about 90 g/L and about 220 g/L, were stabilized for at least 24 months when stored at a temperature of 28° C. to 32° C., and for at least 6 months when stored at a temperature of 38° C. to 42° C. Maximum stability was observed with addition of 150 mM sodium chloride.

Under these conditions, the addition of sodium chloride to formulations at pH values at and above 7.0 resulted in considerably higher aggregation and fragmentation rates of the immunoglobulins, compared to samples formulated at a pH between 5.5 and 7.0 (Table 3). Similarly, it was previously observed that sodium chloride significantly destabilized immunoglobulin formulations with acidic pH values (under 5.5).

Advantageously, it is shown herein (e.g., in Examples 3 to 17) that the use of histidine stabilizes immunoglobulin formulations at mildly acidic to neutral pH in the absence of sodium chloride. It should be noted that the formulations may contain chloride ions provided from hydrochloric acid used to pH histidine buffers and the final formulation itself.

II. Definitions

As used herein, a "storage stable" aqueous composition refers to a protein solution (e.g., an immunoglobulin solution) that has been formulated with histidine to increase the stability of the protein in solution, for example by at least 20%, over a given storage time. In the context of the present invention, a labile protein solution (e.g., immunoglobulin solution) formulated at a mildly acidic to neutral pH can be made "storage stable" by the addition of histidine as a stabilizing agent. The stability of the immunoglobulin formulation can be measured, for example, by monitoring the formation of aggregates, loss of bulk enzymatic activity, loss of antigenic titer or formation of degradation products, over a period of time.

As used herein, the term "time of stability" refers to the length of time a composition is considered stable. For example, the time of stability for a composition may refer to the length of time for which the level of protein aggregation and/or degradation in the composition remains below a certain threshold (e.g., 1%, 2%, 3%, 4%, 5%, 6%, 7%, 8%, 9%, 10%, 11%, 12%, 13%, 14%, 15%, 16%, 17%, 18%, 19%, 20%, etc.), the length of time a composition maintains an enzymatic activity above a certain threshold (e.g., 100%, 95%, 90%, 85%, 80%, 75%, 70%, 65%, 60%, 55%, 50%, etc. of the amount of activity present in the composition at the start of the storage period), or the length of time a composition maintains an antigenic titer (e.g., 100%, 95%, 90%, 85%, 80%, 75%, 70%, 65%, 60%, 55%, 50%, etc. of the antigenic titer present in the composition at the start of the storage period).

In the context of the present invention, a storage stable aqueous composition of a therapeutic protein (e.g., an immunoglobulin composition) formulated with histidine at mildly acidic to neutral pH will have a longer time of stability than a composition of the same therapeutic protein formulated at acidic pH with histidine or mildly acidic to neutral pH without histidine. A storage stable aqueous composition of a therapeutic protein (e.g., an immunoglobulin composition), as provided herein, will have a time of stability that is, for example, at least 20% greater than the time of stability for the same composition formulated in the absence of a histidine or formulated at acid pH with histidine, or formulated at acidic pH with glycine or proline, or at least 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190% greater, or at least 2 times greater, or at least 2.5 times, 3.0 times, 3.5 times, 4.0 times, 4.5 times, 5.0 times, 5.5 times, 6.0 times, 6.5 times, 7.0 times, 7.5 times, 8.0 times, 8.5 times, 9.0 times, 9.5 times, 10 times, or more times greater than the time of stability for the same composition formulated in the absence of a histidine or formulated at acid pH with histidine, or formulated at acidic pH with glycine or proline. In one embodiment, the immunoglobulin composition may be stable under storage conditions for from 25% to 1000% longer when formulated with histidine at mildly acidic to neutral pH, as provided herein, as compared to the stability of the same immunoglobulin under formulated in the absence of a histidine or formulated at acid pH with histidine, or formulated at acidic pH with glycine or proline. In other embodiments, the composition may be stable for from 50% to 1000%, 100% to 1000%, 200% to 1000%, 300% to 1000%, 400% to 1000%, 500% to 1000%, 600% to 1000%, or 700% to 1000%, when formulated according to the present invention.

As used herein, the term "stable" refers to a state of a protein composition (e.g., an immunoglobulin solution) suitable for pharmaceutical administration. In the context of the present invention, an immunoglobulin solution is generally considered to be stable when the level of immunoglobulin aggregation and/or degradation in the composition remains below a certain threshold (e.g., below 1%, 2%, 3%, 4%, 5%, 6%, 7%, 8%, 9%, 10%, 11%, 12%, 13%, 14%, 15%, 16%, 17%, 18%, 19%, 20%, etc.) or the when the antigenic titer remains above a certain threshold (e.g., above 100%, 95%, 90%, 85%, 80%, 75%, 70%, 65%, 60%, 55%, 50%, etc. of the antigenic titer present in the composition at the start of a storage period).

The European Pharmacopoeia (Ph. Eur.) standard for normal human immunoglobulins is that the composition have: (i) a monomer and dimer content equal to or greater than 85% of the total area of a standard chromatogram; and (ii) a polymer and aggregate sum content of not more than 10% of the total area of the chromatogram. For IGIV the sum of the peak areas of the monomer and dimer represents not less than 95 percent and the maximum amount of polymers and aggregates is no more than 2%. Accordingly, in one embodiment, a composition provided herein is considered to be stable when at least 85% of the immunoglobulin content is monomeric and no more than 2% of the immunoglobulin content is aggregated.

As used herein, "storage" means that a formulation is not immediately administered to a subject once prepared, but is kept for a period of time under particular conditions (e.g., at a particular temperature, under a particular atmosphere, protected from light, etc.) prior to use. For example, a liquid formulation can be kept for days, weeks, months or years, prior to administration to a subject under varied temperatures such as refrigerated (0° to 10° C.) or room temperature (e.g., temperature between 20 and 25° C.).

For the purposes of the present invention, when referring to a concentration of an individual component of a composition, the phrases "no more than X" and "from 0 to X" are equivalent and refer to any concentration between and including 0 and X. For example, the phrases "a concentration of no more than 2%" and "a concentration of from 0% to 2%" are equivalent and include 0%, 1%, and 2%.

For the purposes of the present invention, when referring to a concentration of an individual component of a composition, the phrases "no less than X" refers to any concentration X or higher. For example, the phrase "a concentration of no less than 98%" includes 98%, 99%, and 100%.

For the purposes of the present invention, when referring to a concentration of an individual component of a composition, the phrases "between X and Y" and "from X to X" are equivalent and refer to any concentration between and including X and Y. For example, the phrases "a concentration of between 49% and 51%" and "a concentration of from 49% to 51%" are equivalent and include 49%, 50%, and 51%.

As used herein, an "alkali metal chloride salt" refers to an inorganic salt of an alkali metal and chlorine. For the purposes of the present invention, the alkali metal chloride salt will be a pharmaceutically acceptable salt, most commonly sodium or potassium chloride. In a preferred embodiment, the salt is sodium chloride.

Likewise, an "alkali metal cation" will most commonly refer to a sodium cation ($Na^+$) or potassium cation ($K^+$) and can be contributed by an alkali metal chloride salt or other source. In the context of the present invention, a hydrogen ion is not considered an alkali metal cation, and thus the inclusion of hydrochloric acid will not contribute to the alkali metal cation content of the formulation.

As used herein, an "antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively.

An exemplary immunoglobulin (antibody) structural unit is composed of two pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. In a particular exemplary embodiment, the immunoglobulin will consist of an immunoglobulin preparation isolated from pooled plasma (preferably human plasma) comprising IgG immunoglobulins.

As used herein, the term "about" denotes an approximate range of plus or minus 10% from a specified value. For instance, the language "about 20%" encompasses a range of 18-22%. As used herein, about also includes the exact amount. Hence "about 20%" means "about 20%" and also "20%."

By "therapeutically effective amount or dose" or "sufficient/effective amount or dose," it is meant a dose that produces effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

As used herein, a "stabilizing agent" refers to a chemical, other than an alkali metal chloride salt, which aids in the stabilization of a therapeutic agent in an aqueous formulation under mildly acid to neutral pH. Examples of suitable stabilizing agents for the formulations and methods provided herein include, without limitation, buffering agents (e.g., TRIS, HEPES, potassium or sodium phosphate, amino acids, etc.), osmolytes (e.g., sugars, sugar alcohols, etc.), bulking agents (e.g., amino acids, etc.), divalent salts, surfactants, and the like.

As used herein, "amino acids" refers to any natural or non-natural pharmaceutically acceptable amino acid. Non-limiting examples of amino acids include, isoleucine, alanine, leucine, asparagine, lysine, aspartic acid, methionine, cysteine, phenylalanine, glutamic acid, threonine, glutamine, tryptophan, glycine, valine, proline, selenocysteine, serine, tyrosine, arginine, histidine, ornithine, taurine, and the like.

Any sugar such as mono-, di-, or polysaccharides, or water-soluble glucans, including for example fructose, glucose, mannose, sorbose, xylose, maltose, lactose, sucrose, dextran, trehalose, pullulan, dextrin, cyclodextrin, soluble starch, hydroxyethyl starch, and carboxymethylcellulose may be used.

As used herein, a "sugar alcohol" refers to a hydrocarbon having between about 4 and about 8 carbon atoms and at least one hydroxyl group. Non-limiting examples of sugar alcohols that may be used in formulations provided herein include, mannitol, sorbitol, inositol, galactitol, dulcitol, xylitol, and arabitol.

As used herein, the term "activity" refers to a functional activity or activities of a polypeptide or portion thereof associated with a full-length (complete) protein. Functional activities include, but are not limited to, biological activity, catalytic or enzymatic activity, antigenicity (i.e., the ability to bind or compete with a polypeptide for binding to an anti-polypeptide antibody), immunogenicity, ability to form multimers, and the ability to specifically bind to a receptor or ligand for the polypeptide.

III. Formulations

Among other aspects, the present invention provides stabilized formulations of immunoglobulins for therapeutic administration. The following embodiments are based in part on the unexpected discovery that the formulation of immunoglobulins with histidine at mildly acidic to neutral pH stabilizes the immunoglobulins that are otherwise labile at these pH values, and/or labile when formulated with histidine at an acidic pH, and/or labile when formulated in the presence of alkali metal cations.

As will be recognized by one of skill in the art, immunoglobulin compositions formulated at a particular pH may contain residual counter ions contributed from one or more pH modifying agents. For example, the storage stable compositions provided herein may contain chloride anions contributed from hydrochloric acid, acetate anions contributed from glacial acetic acid, sodium cations contributed from sodium hydroxide, and the like. In the context of the present invention, a storage stable immunoglobulin composition consisting of or consisting essentially of: an immunoglobulin and histidine may further comprise one or more counter ion, as necessitated by the formulation process at a particular pH.

Any immunoglobulin may be stabilized by the formulations provided herein. Non-limiting examples of immunoglobulin preparations that may be stabilized include, plasma-derived immunoglobulin preparations, recombinant polyclonal or monoclonal preparations, minibodies, diabodies, triabodies, antibody fragments such as Fv, Fab and F(ab)2 or fragmented antibodies such as monovalent or multivalent single chain Fvs (scFv, sc(Fv)2, minibodies, diabodies, and triabodies such as scFv dimers) in which the variable regions of an antibody are joined together via a linker such as a peptide linker, and the like. Recombinant antibodies include murine antibodies, rodent antibodies, human antibodies, chimeric human antibodies (e.g., human/murine chimeras), humanized antibodies (e.g., humanized murine antibodies), and the like. In preferred embodiments, the recombinant antibody is a human, chimeric human, or humanized antibody suitable for administration to a human. In a preferred embodiment, the immunoglobulin in a full length, or near full length immunoglobulin, which will generally be more labile then engineered fragments thereof.

Generally, storage stable immunoglobulin formulations provided herein will be stabilized at room temperature (i.e., between 20° C. and 25° C.) for an extended period of time. For example, in one embodiment, a storage stable, aqueous immunoglobulin composition will be stable when stored at room temperature for at least about 2 months. In another embodiment, the composition will be stable for at least about 3 months. In yet other embodiment, the composition will be stable for at least 1 about month, or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more months. In a preferred embodiment, the composition will be stable for at least about 6 months. In a more preferred embodiment, the composition will be stable for at least about 1 year. In a more preferred embodiment, the composition will be stable for at least about 2 years.

In one embodiment, the storage stable, aqueous immunoglobulin composition will be stable for at least six months at a temperature between about 28° C. and about 32° C. In a specific embodiment, the storage stable, aqueous immunoglobulin composition will be stable for at least one year at a temperature between about 28° C. and about 32° C. In a more specific embodiment, the storage stable, aqueous immunoglobulin composition will be stable for at least two years at a temperature between about 28° C. and about 32° C. In another embodiment, the storage stable, aqueous immunoglobulin composition will be stable for at least one month at a temperature between about 38° C. and about 42° C. In a specific embodiment, the storage stable, aqueous immunoglobulin composition will be stable for at least three months at a temperature between about 38° C. and about 42° C. In a more specific embodiment, the storage stable, aqueous immunoglobulin composition will be stable for at least one year at a temperature between about 38° C. and about 42° C.

In one embodiment, the composition is considered stable as long as the percentage of immunoglobulin in the aggregated state no more than 10%. In a preferred embodiment, the composition is considered stable as long as the percentage of immunoglobulin in the aggregated state no more than 9%. In a more preferred embodiment, the composition is considered stable as long as the percentage of immunoglobulin in the aggregated state no more than 8%. In a more preferred embodiment, the composition is considered stable as long as the percentage of immunoglobulin in the aggregated state no more than 7%. In a more preferred embodiment, the composition is considered stable as long as the percentage of immunoglobulin in the aggregated state no more than 6%. In a more preferred embodiment, the composition is considered stable as long as the percentage of immunoglobulin in the aggregated state no more than 5%. In a more preferred embodiment, the composition is considered stable as long as the percentage of immunoglobulin in the aggregated state no more than 4%. In a more preferred embodiment, the composition is considered stable as long as the percentage of immunoglobulin in the aggregated state no more than 3%. In a most preferred embodiment, the composition is considered stable as long as the percentage of immunoglobulin in the aggregated state no more than 2%.

In one embodiment, the composition is considered stable as long as the percentage of immunoglobulin in the aggregated state no more than 10% and the percentage of immunoglobulin in the monomeric state is no less than 85%. In a preferred embodiment, the composition is considered stable as long as the percentage of immunoglobulin in the aggregated state no more than 9% and the percentage of immunoglobulin in the monomeric state is no less than 85%. In a preferred embodiment, the composition is considered stable as long as the percentage of immunoglobulin in the aggregated state no more than 8% and the percentage of immunoglobulin in the monomeric state is no less than 85%. In a preferred embodiment, the composition is considered stable as long as the percentage of immunoglobulin in the aggregated state no more than 7% and the percentage of immunoglobulin in the monomeric state is no less than 85%. In a preferred embodiment, the composition is considered stable as long as the percentage of immunoglobulin in the aggregated state no more than 6% and the percentage of immunoglobulin in the monomeric state is no less than 85%. In a preferred embodiment, the composition is considered stable as long as the percentage of immunoglobulin in the aggregated state no more than 5% and the percentage of immunoglobulin in the monomeric state is no less than 85%. In a preferred embodiment, the composition is considered stable as long as the percentage of immunoglobulin in the aggregated state no more than 4% and the percentage of immunoglobulin in the monomeric state is no less than 85%. In a preferred embodiment, the composition is considered stable as long as the percentage of immunoglobulin in the aggregated state no more than 3% and the percentage of immunoglobulin in the monomeric state is no less than 85%. In a most preferred embodiment, the composition is considered stable as long as the percentage of immunoglobulin in the aggregated state no more than 2% and the percentage of immunoglobulin in the monomeric state is no less than 85%.

After formulation, the storage stable, aqueous immunoglobulin compositions provided herein are typically sterile filtered and dispensed into a sterile containment vessel, which is sealed air-tight, for example, using a rubber stopper. Immunoglobulin compositions in the air-tight vessels are preferably protected from ambient light by storage in a dark place, the use of a tinted vessel material (typically glass or plastic), and/or covering the surface of the vessel with an opaque substance.

In certain embodiments, the headspace air in the containment vessel is replaced with an inert gas. The inert gas helps to maintain an inert atmosphere above the liquid composition. In one embodiment, the liquid is overlaid with inert gas. In another embodiment the liquid is degassed before overlaying it with inert gas, meaning that residual oxygen in the atmosphere may vary. In the context of the present invention, when an immunoglobulin composition is stored in a vessel in which the headspace air has been replaced with an inert gas, the composition has been overlaid with inert gas, or the composition is degassed prior to overlaying with inert gas, the composition is said to be "stored under inert gas." Non-limiting examples of inert gasses than may be used in conjunction with the present invention include, nitrogen, argon, carbon dioxide, helium, krypton, and xenon. In one particular embodiment, the inert gas is nitrogen. In another particular embodiment, the inert gas is argon.

A. General Immunoglobulin Formulations

In one embodiment, the present invention provides storage stable, aqueous immunoglobulin composition comprising: an immunoglobulin; between 50 mM and 500 mM histidine; no more than 10 mM of an alkali metal cation; and a pH between 5.5 and 7.0. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a particular embodiment, the storage stable, aqueous immunoglobulin composition comprises: an immunoglobulin; between 50 mM and 500 mM histidine; no more than 1 mM of an alkali metal cation; and a pH between 5.5 and 7.0. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

Advantageously, it has been found that the formulation of immunoglobulins with moderate concentrations of histidine (e.g., 50 mM to 500 mM) at mildly acidic to neutral pH stabilizes the immunoglobulin composition in the absence of traditional stabilizing and bulking agents, such as surfactants (e.g., non-ionic surfactants), sugars, and sugar alcohols.

Accordingly, in a specific embodiment, the present invention provides a storage stable, aqueous immunoglobulin composition comprising an immunoglobulin; between 50 mM and 500 mM histidine; no more than 1 mM of an alkali metal cation; no more than 0.01% of a surfactant; no more than 1 mM of a sugar; no more than 1 mM of a sugar alcohol; and a pH between 5.5 and 7.0. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In another specific embodiment, the present invention provides a storage stable, aqueous immunoglobulin composition consisting essentially of: an immunoglobulin; between 50 mM and 500 mM histidine; and a pH between 5.5 and 7.0. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a more specific embodiment, the present invention provides a storage stable, aqueous immunoglobulin composition consisting of an immunoglobulin; between 50 mM and 500 mM histidine; no more than 1 mM of an alkali metal cation; no more than 0.01% of a surfactant; no more than 1 mM of a sugar; no more than 1 mM of a sugar alcohol; and a pH between 5.5 and 7.0. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

The histidine formulations provided by the present invention may be used to stabilize any immunoglobulin composition, including but not limited to: immunoglobulin compositions isolated from pooled plasma (e.g., human pooled plasma); immunoglobulin compositions isolated from mammary secretions; immunoglobulin compositions isolated from avian sources (e.g., IgY containing compositions isolated from the yolk of chicken eggs); and recombinant immunoglobulins (e.g., monoclonal or polyclonal antibodies). In a specific embodiment, the final composition does not contain a surfactant or sugar.

In a preferred embodiment, the present invention provides a storage stable composition of immunoglobulins isolated from pooled plasma (e.g., human pooled plasma). In a particular embodiment, the immunoglobulin composition isolated from pooled plasma comprises at least 90% IgG immunoglobulins. In a specific embodiment, the immunoglobulin composition isolated from pooled plasma comprises at least 95% IgG immunoglobulins. In a more specific embodiment, the immunoglobulin composition isolated from pooled plasma comprises at least 98% IgG immunoglobulins. In certain embodiments, the immunoglobulin composition isolated from pooled plasma comprises IgA and/or IgM immunoglobulins. In a specific embodiment, the final composition does not contain a surfactant or sugar.

1. Histidine

In one embodiment, the concentration of histidine in a storage stable immunoglobulin composition provided herein is between 50 mM and 500 mM. In another embodiment, the concentration of histidine in the formulation will be between 100 mM and 400 mM. In another embodiment, the concentration of histidine in the formulation will be between 200 mM and 300 mM. In another embodiment, the concentration of histidine in the formulation will be between 225 mM and 275 mM. In another embodiment, the concentration of histidine in the formulation will be between 240 mM and 260 mM. In a particular embodiment, the concentration of histidine will be 250 mM. In certain other embodiments, the concentration of histidine in the formulation will be 5±0.5 mM, 10±1 mM, 15±1.5 mM, 20±2 mM, 25±2.5 mM, 50±5 mM, 75±7.5 mM, 100±10 mM, 125±12.5 mM, 150±15 mM, 175±17.5 mM, 200±20 mM, 225±22.5 mM, 250±25 mM, 275±27.5 mM, 300±30 mM, 325±32.5 mM, 350±35 mM, 375±37.5 mM, 400±40 mM, 425±42.5 mM, 450±45 mM, 475±47.5 mM, 500±50 mM or higher. In yet other embodiments, the concentration of histidine in the formulation will be 5 mM, 10 mM, 15 mM, 20 mM, 25 mM, 50 mM, 75 mM, 100 mM, 125 mM, 150 mM, 175 mM, 200 mM, 225 mM, 250 mM, 275 mM, 300 mM, 325 mM, 350 mM, 375 mM, 400 mM, 425 mM, 450 mM, 475 mM, 500 mM or higher.

Accordingly, in one embodiment, the present invention provides a storage stable, aqueous immunoglobulin composition comprising: an immunoglobulin; between 100 mM and 400 mM histidine; no more than 10 mM of an alkali metal cation; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a specific embodiment, the present invention provides a storage stable, aqueous immunoglobulin composition consisting essentially of: an immunoglobulin; between 100 mM and 400 mM histidine; and a pH between 5.5 and 7.0. In a particular embodiment; the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a more specific embodiment, the present invention provides a storage stable, aqueous immunoglobulin composition consisting of: an immunoglobulin; between 100 mM and 400 mM histidine; no more than 10 mM of an alkali metal cation; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In one embodiment, the present invention provides a storage stable, aqueous immunoglobulin composition comprising: an immunoglobulin; between 200 mM and 300 mM histidine; no more than 10 mM of an alkali metal cation; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a specific embodiment, the present invention provides a storage stable, aqueous immunoglobulin composition consisting essentially of: an immunoglobulin; between 200 mM and 300 mM histidine; and a pH between 5.5 and 7.0. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a more specific embodiment, the present invention provides a storage stable, aqueous immunoglobulin composition consisting of: an immunoglobulin; between 200 mM and 300 mM histidine; no more than 10 mM of an alkali metal cation; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In one embodiment, the present invention provides a storage stable, aqueous immunoglobulin composition comprising: an immunoglobulin; between 225 mM and 275 mM histidine; no more than 10 mM of an alkali metal cation; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a specific embodiment, the present invention provides a storage stable, aqueous immunoglobulin composition consisting essentially of: an immunoglobulin; between 225 mM and 275 mM histidine; and a pH between 5.5 and 7.0. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a more specific embodiment, the present invention provides a storage stable, aqueous immunoglobulin composition consisting of: an immunoglobulin; between 225 mM and 275 mM histidine; no more than 10 mM of an alkali metal cation; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In one embodiment, the present invention provides a storage stable, aqueous immunoglobulin composition comprising: an immunoglobulin; between 240 mM and 260 mM histidine; no more than 10 mM of an alkali metal cation; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a specific embodiment, the present invention provides a storage stable, aqueous immunoglobulin composition consisting essentially of: an immunoglobulin; between 240 mM and 260 mM histidine; and a pH between 5.5 and 7.0. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a more specific embodiment, the present invention provides a storage stable, aqueous immunoglobulin composition consisting of: an immunoglobulin; between 240 mM and 260 mM histidine; no more than 10 mM of an alkali metal cation; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In one embodiment, the present invention provides a storage stable, aqueous immunoglobulin composition comprising: an immunoglobulin; 250 mM histidine; no more than 10 mM of an alkali metal cation; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a specific embodiment, the present invention provides a storage stable, aqueous immunoglobulin composition consisting essentially of: an immunoglobulin; 250 mM histidine; and a pH between 5.5 and 7.0. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a more specific embodiment, the present invention provides a storage stable, aqueous immunoglobulin composition consisting of: an immunoglobulin; 250 mM histidine; no more than 10 mM of an alkali metal cation; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

2. pH

The storage stable immunoglobulin compositions provided by the present invention are formulated at mildly acidic to neutral pH. Generally, this includes pH values between 5.5 and 7.0. In a preferred embodiment, the pH value is between 5.5 and 6.5. However, the range of pH values at which any individual immunoglobulin composition is stabilized by the inclusion of histidine in the formulation may vary, dependent upon the properties of the particular immunoglobulin.

For example, in one embodiment, a storage stable formulation will have a pH between 5.5 and 7.0. In another embodiment, a storage stable formulation will have a pH between 5.5 and 6.5. In other embodiments, the pH of the stabilizing formulation will be between 6.0 and 7.0. In another embodiment, the pH of the stabilizing formulation will be between 5.5 and 6.0.

In one embodiment, the pH of the stabilizing formulation will be between 6.0 and 6.5. In another embodiment, the pH of the stabilizing formulation will be between 6.5 and 7.0. In another embodiment, the stabilizing formulation will have a pH of 6.0±0.4. In another embodiment, the stabilizing formulation will have a pH of 6.0±0.3. In another embodiment, the stabilizing formulation will have a pH of 6.0±0.2. In another embodiment, the stabilizing formulation will have a pH of 6.0±0.1. In another embodiment, the stabilizing formulation will have a pH of 6.1±0.5. In another embodiment, the stabilizing formulation will have a pH of 6.1±0.4. In another embodiment, the stabilizing formulation will have a pH of 6.1±0.3. In another embodiment, the stabilizing formulation will have a pH of 6.1±0.2. In another embodiment, the stabilizing formulation will have a pH of 6.1±0.1. In other embodiments, the pH of the stabilizing formulation may be 5.5±0.2, or 5.6±0.2, 5.7±0.2, 5.8±0.2, 5.9±0.2, 6.0±0.2, 6.1±0.2, 6.2±0.2, 6.3±0.2, 6.4±0.2, 6.5±0.2, 6.6±0.2, 6.7±0.2, 6.8±0.2, 6.9±0.2, or 7.0±0.2. In other embodiments, the pH of the stabilizing formulation may be 5.5±0.1, or 5.6±0.1, 5.7±0.1, 5.8±0.1, 5.9±0.1, 6.0±0.1, 6.1±0.1, 6.2±0.1, 6.3±0.1, 6.4±0.1, 6.5±0.1, 6.6±0.1, 6.7±0.1, 6.8±0.1, 6.9±0.1, or 7.0±0.1. In yet other embodiments, the pH of the stabilizing formulation may be 5.5, or 5.6, 5.7, 5.8, 5.9, 6.0, 6.1, 6.2, 6.3, 6.4, 6.5, 6.6, 6.7, 6.8, 6.9, or 7.0.

Accordingly, in one embodiment, the present invention provides a storage stable, aqueous immunoglobulin composition comprising: an immunoglobulin; between 50 mM and 500 mM histidine; no more than 10 mM of an alkali metal cation; and a pH between 5.5 and 6.5. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a specific embodiment, the present invention provides a storage stable, aqueous immunoglobulin composition consisting essentially of: an immunoglobulin; between 50 mM and 500 mM histidine; and a pH between 5.5 and 6.5. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a more specific embodiment, the present invention provides a storage stable, aqueous immunoglobulin composition consisting of: an immunoglobulin; between 50 mM and 500 mM histidine; no more than 10 mM of an alkali metal cation; and a pH between 5.5 and 6.5. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In one embodiment, the present invention provides a storage stable, aqueous immunoglobulin composition comprising: an immunoglobulin; between 200 mM and 300 mM histidine; no more than 10 mM of an alkali metal cation; and a pH between 5.5 and 6.5. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a specific embodiment, the present invention provides a storage stable, aqueous immunoglobulin composition consisting essentially of: an immunoglobulin; between 200 mM and 300 mM histidine; and a pH between 5.5 and 6.5. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a more specific embodiment, the present invention provides a storage stable, aqueous immunoglobulin composition consisting of: an immunoglobulin; between 200 mM and 300 mM histidine; no more than 10 mM of an alkali metal cation; and a pH between 5.5 and 6.5. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In one embodiment, the present invention provides a storage stable, aqueous immunoglobulin composition comprising: an immunoglobulin; between 200 mM and 300 mM histidine; no more than 10 mM of an alkali metal cation; and a pH of 6.1±0.4. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a specific embodiment, the present invention provides a storage stable, aqueous immunoglobulin composition consisting essentially of: an immunoglobulin; between 200 mM and 300 mM histidine; and a pH of 6.1±0.4. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a more specific embodiment, the present invention provides a storage stable, aqueous immunoglobulin composition consisting of: an immunoglobulin; between 200 mM and 300 mM histidine; no more than 10 mM of an alkali metal cation; and a pH of 6.1±0.4. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In one embodiment, the present invention provides a storage stable, aqueous immunoglobulin composition comprising: an immunoglobulin; between 200 mM and 300 mM histidine; no more than 10 mM of an alkali metal cation; and a pH of 6.1±0.3. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a specific embodiment, the present invention provides a storage stable, aqueous immunoglobulin composition consisting essentially of: an immunoglobulin; between 200 mM and 300 mM histidine; and a pH of 6.1±0.3. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a more specific embodiment, the present invention provides a storage stable, aqueous immunoglobulin composition consisting of: an immunoglobulin; between 200 mM and 300 mM histidine; no more than 10 mM of an alkali metal cation; and a pH of 6.1±0.3. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In one embodiment, the present invention provides a storage stable, aqueous immunoglobulin composition comprising: an immunoglobulin; between 200 mM and 300 mM histidine; no more than 10 mM of an alkali metal cation; and a pH of 6.1±0.2. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a specific embodiment, the present invention provides a storage stable, aqueous immunoglobulin composition consisting essentially of: an immunoglobulin; between 200 mM and 300 mM histidine; and a pH of 6.1±0.2. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a more specific embodiment, the present invention provides a storage stable, aqueous immunoglobulin composition consisting of: an immunoglobulin; between 200 mM and 300 mM histidine; no more than 10 mM of an alkali metal cation; and a pH of 6.1±0.2. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In one embodiment, the present invention provides a storage stable, aqueous immunoglobulin composition comprising: an immunoglobulin; between 200 mM and 300 mM histidine; no more than 10 mM of an alkali metal cation; and a pH of 6.1±0.1. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. An a specific embodiment, the final composition does not contain a surfactant or sugar.

In a specific embodiment, the present invention provides a storage stable, aqueous immunoglobulin composition consisting essentially of: an immunoglobulin; between 200 mM and 300 mM histidine; and a pH of 6.1±0.1. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In as specific embodiment, the composition is stored Under nitrogen. In another specific embodiment, the composition is stored under argon. In yet another specific embodiment, the composition is stored under carbon dioxide. In a specific embodiment, the final composition does not contain a surfactant or sugar.

In a more specific embodiment, the present invention provides a storage stable, aqueous immunoglobulin composition consisting of: an immunoglobulin; between 200 mM and 300 mM histidine; no more than 10 mM of an alkali metal cation; and a pH of 6.1±0.1. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In one embodiment, the present invention provides a storage stable, aqueous immunoglobulin composition comprising: an immunoglobulin; between 200 mM and 300 mM histidine; no more than 10 mM of an alkali metal cation; and a pH of 6.1. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a specific embodiment, the present invention provides a storage stable, aqueous immunoglobulin composition consisting essentially of: an immunoglobulin; between 200 mM and 300 mM histidine; and a pH of 6.1. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a more specific embodiment, the present invention provides a storage stable, aqueous immunoglobulin composition consisting of: an immunoglobulin; between 200 mM and 300 mM histidine; no more than 10 mM of an alkali metal cation; and a pH of 6.1. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In certain embodiments, the combination of histidine concentration and pH of the formulation will be selected from any one of variations (Var.) 1 to 952, as provided in Table 1 and Table 2.

Accordingly, in one embodiment, the present invention provides a storage stable, aqueous immunoglobulin composition comprising: an immunoglobulin; no more than 10 mM of an alkali metal cation; and a histidine/pH combination selected from the group consisting of variations 1 to 952, as provided in Table 1 and Table 2. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a specific embodiment, the present invention provides a storage stable, aqueous immunoglobulin composition consisting essentially of: an immunoglobulin and a histidine/pH combination selected from the group consisting of variations 1 to 952, as provided in Table 1 and Table 2. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a more specific embodiment, the present invention provides a storage stable, aqueous immunoglobulin composition consisting of: an immunoglobulin; no more than 10 mM of an alkali metal cation; and a histidine/pH combination selected from the group consisting of variations 1 to 952, as provided in Table 1 and Table 2. In a particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

TABLE 1

Particular combinations of histidine concentration and pH useful for the formulation of immunoglobulins.

| pH | Histidine (mM) | | | | | | | |
|---|---|---|---|---|---|---|---|---|
|  | 5-500 | 100-400 | 200-300 | 225-275 | 250 ± 10 | 250 | 50 ± 5 | 100 ± 10 |
| 5.5-7.0 | Var. 1 | Var. 57 | Var. 113 | Var. 169 | Var. 225 | Var. 281 | Var. 337 | Var. 393 |
| 5.5-6.5 | Var. 2 | Var. 58 | Var. 114 | Var. 170 | Var. 226 | Var. 282 | Var. 338 | Var. 394 |
| 5.5-6.0 | Var. 3 | Var. 59 | Var. 115 | Var. 171 | Var. 227 | Var. 283 | Var. 339 | Var. 395 |
| 6.0-7.0 | Var. 4 | Var. 60 | Var. 116 | Var. 172 | Var. 228 | Var. 284 | Var. 340 | Var. 396 |
| 6.0-6.5 | Var. 5 | Var. 61 | Var. 117 | Var. 173 | Var. 229 | Var. 285 | Var. 341 | Var. 397 |
| 6.1 ± 0.5 | Var. 6 | Var. 62 | Var. 118 | Var. 174 | Var. 230 | Var. 286 | Var. 342 | Var. 398 |
| 6.1 ± 0.4 | Var. 7 | Var. 63 | Var. 119 | Var. 175 | Var. 231 | Var. 287 | Var. 343 | Var. 399 |
| 6.1 ± 0.3 | Var. 8 | Var. 64 | Var. 120 | Var. 176 | Var. 232 | Var. 288 | Var. 344 | Var. 400 |
| 6.1 ± 0.2 | Var. 9 | Var. 65 | Var. 121 | Var. 177 | Var. 233 | Var. 289 | Var. 345 | Var. 401 |
| 6.1 ± 0.1 | Var. 10 | Var. 66 | Var. 122 | Var. 178 | Var. 234 | Var. 290 | Var. 346 | Var. 402 |

TABLE 1-continued

Particular combinations of histidine concentration and pH useful for the formulation of immunoglobulins.

| pH | Histidine (mM) | | | | | | | |
|---|---|---|---|---|---|---|---|---|
| | 5-500 | 100-400 | 200-300 | 225-275 | 250 ± 10 | 250 | 50 ± 5 | 100 ± 10 |
| 6.1 | Var. 11 | Var. 67 | Var. 123 | Var. 179 | Var. 235 | Var. 291 | Var. 347 | Var. 403 |
| 5.5 ± 0.2 | Var. 12 | Var. 68 | Var. 124 | Var. 180 | Var. 236 | Var. 292 | Var. 348 | Var. 404 |
| 5.6 ± 0.2 | Var. 13 | Var. 69 | Var. 125 | Var. 181 | Var. 237 | Var. 293 | Var. 349 | Var. 405 |
| 5.7 ± 0.2 | Var. 14 | Var. 70 | Var. 126 | Var. 182 | Var. 238 | Var. 294 | Var. 350 | Var. 406 |
| 5.8 ± 0.2 | Var. 15 | Var. 71 | Var. 127 | Var. 183 | Var. 239 | Var. 295 | Var. 351 | Var. 407 |
| 5.9 ± 0.2 | Var. 16 | Var. 72 | Var. 128 | Var. 184 | Var. 240 | Var. 296 | Var. 352 | Var. 408 |
| 6.0 ± 0.2 | Var. 17 | Var. 73 | Var. 129 | Var. 185 | Var. 241 | Var. 297 | Var. 353 | Var. 409 |
| 6.2 ± 0.2 | Var. 18 | Var. 74 | Var. 130 | Var. 186 | Var. 242 | Var. 298 | Var. 354 | Var. 410 |
| 6.3 ± 0.2 | Var. 19 | Var. 75 | Var. 131 | Var. 187 | Var. 243 | Var. 299 | Var. 355 | Var. 411 |
| 6.4 ± 0.2 | Var. 20 | Var. 76 | Var. 132 | Var. 188 | Var. 244 | Var. 300 | Var. 356 | Var. 412 |
| 6.5 ± 0.2 | Var. 21 | Var. 77 | Var. 133 | Var. 189 | Var. 245 | Var. 301 | Var. 357 | Var. 413 |
| 6.6 ± 0.2 | Var. 22 | Var. 78 | Var. 134 | Var. 190 | Var. 246 | Var. 302 | Var. 358 | Var. 414 |
| 6.7 ± 0.2 | Var. 23 | Var. 79 | Var. 135 | Var. 191 | Var. 247 | Var. 303 | Var. 359 | Var. 415 |
| 6.8 ± 0.2 | Var. 24 | Var. 80 | Var. 136 | Var. 192 | Var. 248 | Var. 304 | Var. 360 | Var. 416 |
| 6.9 ± 0.2 | Var. 25 | Var. 81 | Var. 137 | Var. 193 | Var. 249 | Var. 305 | Var. 361 | Var. 417 |
| 7.0 ± 0.2 | Var. 26 | Var. 82 | Var. 138 | Var. 194 | Var. 250 | Var. 306 | Var. 362 | Var. 418 |
| 5.5 ± 0.1 | Var. 27 | Var. 83 | Var. 139 | Var. 195 | Var. 251 | Var. 307 | Var. 363 | Var. 419 |
| 5.6 ± 0.1 | Var. 28 | Var. 84 | Var. 140 | Var. 196 | Var. 252 | Var. 308 | Var. 364 | Var. 420 |
| 5.7 ± 0.1 | Var. 29 | Var. 85 | Var. 141 | Var. 197 | Var. 253 | Var. 309 | Var. 365 | Var. 421 |
| 5.8 ± 0.1 | Var. 30 | Var. 86 | Var. 142 | Var. 198 | Var. 254 | Var. 310 | Var. 366 | Var. 422 |
| 5.9 ± 0.1 | Var. 31 | Var. 87 | Var. 143 | Var. 199 | Var. 255 | Var. 311 | Var. 367 | Var. 423 |
| 6.0 ± 0.1 | Var. 32 | Var. 88 | Var. 144 | Var. 200 | Var. 256 | Var. 312 | Var. 368 | Var. 424 |
| 6.2 ± 0.1 | Var. 33 | Var. 89 | Var. 145 | Var. 201 | Var. 257 | Var. 313 | Var. 369 | Var. 425 |
| 6.3 ± 0.1 | Var. 34 | Var. 90 | Var. 146 | Var. 202 | Var. 258 | Var. 314 | Var. 370 | Var. 426 |
| 6.4 ± 0.1 | Var. 35 | Var. 91 | Var. 147 | Var. 203 | Var. 259 | Var. 315 | Var. 371 | Var. 427 |
| 6.5 ± 0.1 | Var. 36 | Var. 92 | Var. 148 | Var. 204 | Var. 260 | Var. 316 | Var. 372 | Var. 428 |
| 6.6 ± 0.1 | Var. 37 | Var. 93 | Var. 149 | Var. 205 | Var. 261 | Var. 317 | Var. 373 | Var. 429 |
| 6.7 ± 0.1 | Var. 38 | Var. 94 | Var. 150 | Var. 206 | Var. 262 | Var. 318 | Var. 374 | Var. 430 |
| 6.8 ± 0.1 | Var. 39 | Var. 95 | Var. 151 | Var. 207 | Var. 263 | Var. 319 | Var. 375 | Var. 431 |
| 6.9 ± 0.1 | Var. 40 | Var. 96 | Var. 152 | Var. 208 | Var. 264 | Var. 320 | Var. 376 | Var. 432 |
| 7.0 ± 0.1 | Var. 41 | Var. 97 | Var. 153 | Var. 209 | Var. 265 | Var. 321 | Var. 377 | Var. 433 |
| 5.5 | Var. 42 | Var. 98 | Var. 154 | Var. 210 | Var. 266 | Var. 322 | Var. 378 | Var. 434 |
| 5.6 | Var. 43 | Var. 99 | Var. 155 | Var. 211 | Var. 267 | Var. 323 | Var. 379 | Var. 435 |
| 5.7 | Var. 44 | Var. 100 | Var. 156 | Var. 212 | Var. 268 | Var. 324 | Var. 380 | Var. 436 |
| 5.8 | Var. 45 | Var. 101 | Var. 157 | Var. 213 | Var. 269 | Var. 325 | Var. 381 | Var. 437 |
| 5.9 | Var. 46 | Var. 102 | Var. 158 | Var. 214 | Var. 270 | Var. 326 | Var. 382 | Var. 438 |
| 6 | Var. 47 | Var. 103 | Var. 159 | Var. 215 | Var. 271 | Var. 327 | Var. 383 | Var. 439 |
| 6.2 | Var. 48 | Var. 104 | Var. 160 | Var. 216 | Var. 272 | Var. 328 | Var. 384 | Var. 440 |
| 6.3 | Var. 49 | Var. 105 | Var. 161 | Var. 217 | Var. 273 | Var. 329 | Var. 385 | Var. 441 |
| 6.4 | Var. 50 | Var. 106 | Var. 162 | Var. 218 | Var. 274 | Var. 330 | Var. 386 | Var. 442 |
| 6.5 | Var. 51 | Var. 107 | Var. 163 | Var. 219 | Var. 275 | Var. 331 | Var. 387 | Var. 443 |
| 6.6 | Var. 52 | Var. 108 | Var. 164 | Var. 220 | Var. 276 | Var. 332 | Var. 388 | Var. 444 |
| 6.7 | Var. 53 | Var. 109 | Var. 165 | Var. 221 | Var. 277 | Var. 333 | Var. 389 | Var. 445 |
| 6.8 | Var. 54 | Var. 110 | Var. 166 | Var. 222 | Var. 278 | Var. 334 | Var. 390 | Var. 446 |
| 6.9 | Var. 55 | Var. 111 | Var. 167 | Var. 223 | Var. 279 | Var. 335 | Var. 391 | Var. 447 |
| 7 | Var. 56 | Var. 112 | Var. 168 | Var. 224 | Var. 280 | Var. 336 | Var. 392 | Var. 448 |

TABLE 2

Particular combinations of histidine concentration and pH useful for the formulation of immunoglobulins.

| pH | Histidine [mM] | | | | | | | |
|---|---|---|---|---|---|---|---|---|
| | 150 ± 15 | 175 ± 17.5 | 200 ± 20 | 225 ± 22.5 | 275 ± 27.5 | 300 ± 30 | 350 ± 35 | 400 ± 40 | 500 ± 50 |
| 5.5-7.0 | Var. 449 | Var. 505 | Var. 561 | Var. 617 | Var. 673 | Var. 729 | Var. 785 | Var. 841 | Var. 897 |
| 5.5-6.5 | Var. 450 | Var. 506 | Var. 562 | Var. 618 | Var. 674 | Var. 730 | Var. 786 | Var. 842 | Var. 898 |
| 5.5-6.0 | Var. 451 | Var. 507 | Var. 563 | Var. 619 | Var. 675 | Var. 731 | Var. 787 | Var. 843 | Var. 899 |
| 6.0-7.0 | Var. 452 | Var. 508 | Var. 564 | Var. 620 | Var. 676 | Var. 732 | Var. 788 | Var. 844 | Var. 900 |
| 6.0-6.5 | Var. 453 | Var. 509 | Var. 565 | Var. 621 | Var. 677 | Var. 733 | Var. 789 | Var. 845 | Var. 901 |
| 6.1 ± 0.5 | Var. 454 | Var. 510 | Var. 566 | Var. 622 | Var. 678 | Var. 734 | Var. 790 | Var. 846 | Var. 902 |
| 6.1 ± 0.4 | Var. 455 | Var. 511 | Var. 567 | Var. 623 | Var. 679 | Var. 735 | Var. 791 | Var. 847 | Var. 903 |

TABLE 2-continued

Particular combinations of histidine concentration and pH useful for the formulation of immunoglobulins.

| | Histidine [mM] | | | | | | | | |
|---|---|---|---|---|---|---|---|---|---|
| pH | 150 ± 15 | 175 ± 17.5 | 200 ± 20 | 225 ± 22.5 | 275 ± 27.5 | 300 ± 30 | 350 ± 35 | 400 ± 40 | 500 ± 50 |
| 6.1 ± 0.3 | Var. 456 | Var. 512 | Var. 568 | Var. 624 | Var. 680 | Var. 736 | Var. 792 | Var. 848 | Var. 904 |
| 6.1 ± 0.2 | Var. 457 | Var. 513 | Var. 569 | Var. 625 | Var. 681 | Var. 737 | Var. 793 | Var. 849 | Var. 905 |
| 6.1 ± 0.1 | Var. 458 | Var. 514 | Var. 570 | Var. 626 | Var. 682 | Var. 738 | Var. 794 | Var. 850 | Var. 906 |
| 6.1 | Var. 459 | Var. 515 | Var. 571 | Var. 627 | Var. 683 | Var. 739 | Var. 795 | Var. 851 | Var. 907 |
| 5.5 ± 0.2 | Var. 460 | Var. 516 | Var. 572 | Var. 628 | Var. 684 | Var. 740 | Var. 796 | Var. 852 | Var. 908 |
| 5.6 ± 0.2 | Var. 461 | Var. 517 | Var. 573 | Var. 629 | Var. 685 | Var. 741 | Var. 797 | Var. 853 | Var. 909 |
| 5.7 ± 0.2 | Var. 462 | Var. 518 | Var. 574 | Var. 630 | Var. 686 | Var. 742 | Var. 798 | Var. 854 | Var. 910 |
| 5.8 ± 0.2 | Var. 463 | Var. 519 | Var. 575 | Var. 631 | Var. 687 | Var. 743 | Var. 799 | Var. 855 | Var. 911 |
| 5.9 ± 0.2 | Var. 464 | Var. 520 | Var. 576 | Var. 632 | Var. 688 | Var. 744 | Var. 800 | Var. 856 | Var. 912 |
| 6.0 ± 0.2 | Var. 465 | Var. 521 | Var. 577 | Var. 633 | Var. 689 | Var. 745 | Var. 801 | Var. 857 | Var. 913 |
| 6.2 ± 0.2 | Var. 466 | Var. 522 | Var. 578 | Var. 634 | Var. 690 | Var. 746 | Var. 802 | Var. 858 | Var. 914 |
| 6.3 ± 0.2 | Var. 467 | Var. 523 | Var. 579 | Var. 635 | Var. 691 | Var. 747 | Var. 803 | Var. 859 | Var. 915 |
| 6.4 ± 0.2 | Var. 468 | Var. 524 | Var. 580 | Var. 636 | Var. 692 | Var. 748 | Var. 804 | Var. 860 | Var. 916 |
| 6.5 ± 0.2 | Var. 469 | Var. 525 | Var. 581 | Var. 637 | Var. 693 | Var. 749 | Var. 805 | Var. 861 | Var. 917 |
| 6.6 ± 0.2 | Var. 470 | Var. 526 | Var. 582 | Var. 638 | Var. 694 | Var. 750 | Var. 806 | Var. 862 | Var. 918 |
| 6.7 ± 0.2 | Var. 471 | Var. 527 | Var. 583 | Var. 639 | Var. 695 | Var. 751 | Var. 807 | Var. 863 | Var. 919 |
| 6.8 ± 0.2 | Var. 472 | Var. 528 | Var. 584 | Var. 640 | Var. 696 | Var. 752 | Var. 808 | Var. 864 | Var. 920 |
| 6.9 ± 0.2 | Var. 473 | Var. 529 | Var. 585 | Var. 641 | Var. 697 | Var. 753 | Var. 809 | Var. 865 | Var. 921 |
| 7.0 ± 0.2 | Var. 474 | Var. 530 | Var. 586 | Var. 642 | Var. 698 | Var. 754 | Var. 810 | Var. 866 | Var. 922 |
| 5.5 ± 0.1 | Var. 475 | Var. 531 | Var. 587 | Var. 643 | Var. 699 | Var. 755 | Var. 811 | Var. 867 | Var. 923 |
| 5.6 ± 0.1 | Var. 476 | Var. 532 | Var. 588 | Var. 644 | Var. 700 | Var. 756 | Var. 812 | Var. 868 | Var. 924 |
| 5.7 ± 0.1 | Var. 477 | Var. 533 | Var. 589 | Var. 645 | Var. 701 | Var. 757 | Var. 813 | Var. 869 | Var. 925 |
| 5.8 ± 0.1 | Var. 478 | Var. 534 | Var. 590 | Var. 646 | Var. 702 | Var. 758 | Var. 814 | Var. 870 | Var. 926 |
| 5.9 ± 0.1 | Var. 479 | Var. 535 | Var. 591 | Var. 647 | Var. 703 | Var. 759 | Var. 815 | Var. 871 | Var. 927 |
| 6.0 ± 0.1 | Var. 480 | Var. 536 | Var. 592 | Var. 648 | Var. 704 | Var. 760 | Var. 816 | Var. 872 | Var. 928 |
| 6.2 ± 0.1 | Var. 481 | Var. 537 | Var. 593 | Var. 649 | Var. 705 | Var. 761 | Var. 817 | Var. 873 | Var. 929 |
| 6.3 ± 0.1 | Var. 482 | Var. 538 | Var. 594 | Var. 650 | Var. 706 | Var. 762 | Var. 818 | Var. 874 | Var. 930 |
| 6.4 ± 0.1 | Var. 483 | Var. 539 | Var. 595 | Var. 651 | Var. 707 | Var. 763 | Var. 819 | Var. 875 | Var. 931 |
| 6.5 ± 0.1 | Var. 484 | Var. 540 | Var. 596 | Var. 652 | Var. 708 | Var. 764 | Var. 820 | Var. 876 | Var. 932 |
| 6.6 ± 0.1 | Var. 485 | Var. 541 | Var. 597 | Var. 653 | Var. 709 | Var. 765 | Var. 821 | Var. 877 | Var. 933 |
| 6.7 ± 0.1 | Var. 486 | Var. 542 | Var. 598 | Var. 654 | Var. 710 | Var. 766 | Var. 822 | Var. 878 | Var. 934 |
| 6.8 ± 0.1 | Var. 487 | Var. 543 | Var. 599 | Var. 655 | Var. 711 | Var. 767 | Var. 823 | Var. 879 | Var. 935 |
| 6.9 ± 0.1 | Var. 488 | Var. 544 | Var. 600 | Var. 656 | Var. 712 | Var. 768 | Var. 824 | Var. 880 | Var. 936 |
| 7.0 ± 0.1 | Var. 489 | Var. 545 | Var. 601 | Var. 657 | Var. 713 | Var. 769 | Var. 825 | Var. 881 | Var. 937 |
| 5.5 | Var. 490 | Var. 546 | Var. 602 | Var. 658 | Var. 714 | Var. 770 | Var. 826 | Var. 882 | Var. 938 |
| 5.6 | Var. 491 | Var. 547 | Var. 603 | Var. 659 | Var. 715 | Var. 771 | Var. 827 | Var. 883 | Var. 939 |

TABLE 2-continued

Particular combinations of histidine concentration and pH useful for the formulation of immunoglobulins.

| | Histidine [mM] | | | | | | | | |
|---|---|---|---|---|---|---|---|---|---|
| pH | 150 ± 15 | 175 ± 17.5 | 200 ± 20 | 225 ± 22.5 | 275 ± 27.5 | 300 ± 30 | 350 ± 35 | 400 ± 40 | 500 ± 50 |
| 5.7 | Var. 492 | Var. 548 | Var. 604 | Var. 660 | Var. 716 | Var. 772 | Var. 828 | Var. 884 | Var. 940 |
| 5.8 | Var. 493 | Var. 549 | Var. 605 | Var. 661 | Var. 717 | Var. 773 | Var. 829 | Var. 885 | Var. 941 |
| 5.9 | Var. 494 | Var. 550 | Var. 606 | Var. 662 | Var. 718 | Var. 774 | Var. 830 | Var. 886 | Var. 942 |
| 6 | Var. 495 | Var. 551 | Var. 607 | Var. 663 | Var. 719 | Var. 775 | Var. 831 | Var. 887 | Var. 943 |
| 6.2 | Var. 496 | Var. 552 | Var. 608 | Var. 664 | Var. 720 | Var. 776 | Var. 832 | Var. 888 | Var. 944 |
| 6.3 | Var. 497 | Var. 553 | Var. 609 | Var. 665 | Var. 721 | Var. 777 | Var. 833 | Var. 889 | Var. 945 |
| 6.4 | Var. 498 | Var. 554 | Var. 610 | Var. 666 | Var. 722 | Var. 778 | Var. 834 | Var. 890 | Var. 946 |
| 6.5 | Var. 499 | Var. 555 | Var. 611 | Var. 667 | Var. 723 | Var. 779 | Var. 835 | Var. 891 | Var. 947 |
| 6.6 | Var. 500 | Var. 556 | Var. 612 | Var. 668 | Var. 724 | Var. 780 | Var. 836 | Var. 892 | Var. 948 |
| 6.7 | Var. 501 | Var. 557 | Var. 613 | Var. 669 | Var. 725 | Var. 781 | Var. 837 | Var. 893 | Var. 949 |
| 6.8 | Var. 502 | Var. 558 | Var. 614 | Var. 670 | Var. 726 | Var. 782 | Var. 838 | Var. 894 | Var. 950 |
| 6.9 | Var. 503 | Var. 559 | Var. 615 | Var. 671 | Var. 727 | Var. 783 | Var. 839 | Var. 895 | Var. 951 |
| 7 | Var. 504 | Var. 560 | Var. 616 | Var. 672 | Var. 728 | Var. 784 | Var. 840 | Var. 896 | Var. 952 |

3. Counter Ions

Generally, the storage stable immunoglobulin compositions provided herein will also contain counter ions, both anions and cations, contributed from pH modifying reagents such as hydrochloric acid, glacial acetic acid, and sodium hydroxide. Accordingly, in certain embodiments, the storage stable immunoglobulin compositions provided herein will further comprise chloride or acetate anions contributed from their respective acids used to pH the solution. In one embodiment, the immunoglobulin composition with comprise between 10 mM and 400 mM chloride ions.

The amount of counter ions present in a storage stable immunoglobulin composition provided herein will depend on the amount of pH modifying agent (e.g., hydrochloric acid (HCl), acetic acid, sodium hydroxide, etc.) used to formulate the immunoglobulin composition at a desired pH. Factors that may contribute to variability in the amount of a pH modifying agent used for this purpose include the identity and concentration of the immunoglobulins being formulated, the desired pH (i.e., the lower the desired pH, the more acid will be needed for formulation), and the concentration of histidine in the formulation. For instance, it was found that the amount of HCl needed to formulate the 20% IgG immunoglobulin compositions described in the Examples below with 250 mM histidine at pH 6.1 resulted in a final immunoglobulin composition containing about 155 mM chloride ions. In certain instances where the pH of the composition is being adjusted with an acid, the use of sodium hydroxide may be necessary if the pH drops below the desired pH (i.e., back titration of pH using sodium hydroxide).

Accordingly, in one embodiment, the storage stable immunoglobulin composition will contain no more than 500 mM chloride ions. In another embodiment, the composition will contain no more than 400 mM chloride ions. In another embodiment, the composition will contain no more than 300 mM chloride ions. In another embodiment, the composition will contain no more than 200 mM chloride ions. In yet another embodiment, the composition will contain no more than 100 mM chloride ions. In one embodiment, the concentration of chloride ions in a storage stable aqueous immunoglobulin composition provided herein is between 1 mM and 400 mM. In another embodiment, the concentration of chloride ions is between 10 mM and 400 mM. In another embodiment, the concentration of chloride ions is between 10 mM and 300 mM. In another embodiment, the concentration of chloride ions is between 10 mM and 200 mM. In another embodiment, the concentration of chloride ions is between 10 mM and 100 mM. In one embodiment, the concentration of chloride ions is between 50 mM and 400 mM. In another embodiment, the concentration of chloride ions is between 50 mM and 300 mM. In another embodiment, the concentration of chloride ions is between 50 mM and 200 mM. In one embodiment, the concentration of chloride ions is between 100 mM and 400 mM. In another embodiment, the concentration of chloride ions is between 100 mM and 300 mM. In another embodiment, the concentration of chloride ions is between 100 mM and 200 mM. In yet other embodiments, the concentration of chloride ions is 10±1 mM, 20±2 mM, 30±3 mM, 40±4 mM, 50±5 mM, 60±6 mM, 70±7 mM, 80±8 mM, 90±9 mM, 100±10 mM, 125±12.5 mM, 150±15 mM, 175±17.5 mM, 200±20 mM, 225±22.5 mM, 250±25 mM, 300±30 mM, 350±35 mM, 400±40 mM, 450±45 mM, or 500±50 mM.

In one embodiment, the present invention provides a storage stable immunoglobulin composition comprising: an immunoglobulin; between 50 mM and 500 mM histidine; no more than 10 mM of an alkali metal cation; between 10 mM and 400 mM chloride ions; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a specific embodiment, the present invention provides a storage stable immunoglobulin composition consisting essentially of: an immunoglobulin; between 50 mM and 500 mM histidine; between 10 mM and 400 mM chloride ions; and a pH between 5.5 and 7.0. In a particular embodiment, the composition contains no more than 10 mM of an alkali metal cation. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a more specific embodiment, the present invention provides a storage stable immunoglobulin composition consisting of: an immunoglobulin; between 50 mM and 500 mM histidine; no more than 10 mM of an alkali metal cation; between 10 mM and 400 mM chloride ions; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In one embodiment, the present invention provides a storage stable immunoglobulin composition comprising: an immunoglobulin; between 50 mM and 500 mM histidine; no more than 10 mM of an alkali metal cation; between 100 mM and 200 mM chloride ions; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a specific embodiment, the present invention provides a storage stable immunoglobulin composition consisting essentially of: an immunoglobulin; between 50 mM and 500 mM histidine; between 100 mM and 200 mM chloride ions; and a pH between 5.5 and 7.0. In a particular embodiment, the composition contains no more than 10 mM of an alkali metal cation. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a more specific embodiment, the present invention provides a storage stable immunoglobulin composition consisting of: an immunoglobulin; between 50 mM and 500 mM histidine; no more than 10 mM of an alkali metal cation; between 100 mM and 200 mM chloride ions; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In one embodiment, the present invention provides a storage stable immunoglobulin composition comprising: an immunoglobulin; no more than 10 mM of an alkali metal cation; a histidine/pH combination selected from the group consisting of variations 1 to 952, as provided in Table 1 and Table 2; and between 10 mM and 400 mM chloride ions. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a specific embodiment, the present invention provides a storage stable immunoglobulin composition consisting essentially of: an immunoglobulin; a histidine/pH combination selected from the group consisting of variations 1 to 952, as provided in Table 1 and Table 2; and between 101 mM and 400 mM chloride ions. In a particular embodiment, the composition contains no more than 10 mM of an alkali metal cation. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a more specific embodiment, the present invention provides a storage stable immunoglobulin composition consisting of: an immunoglobulin; no more than 10 mM of an alkali metal cation; a histidine/pH combination selected from the group consisting of variations 1 to 952, as provided in Table 1 and Table 2; and between 10 mM and 400 mM chloride ions. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In one embodiment, the present invention provides a storage stable immunoglobulin composition comprising: an immunoglobulin; no more than 10 mM of an alkali metal cation; a histidine/pH combination selected from the group consisting of variations 1 to 952, as provided in Table 1 and Table 2; and between 100 mM and 200 mM chloride ions. In a specific embodiment, the composition, contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a specific embodiment, the present invention provides a storage stable immunoglobulin composition consisting essentially of: an immunoglobulin; a histidine/pH combination selected from the group consisting of variations 1 to 952, as provided in Table 1 and Table 2; and between 100 mM and 200 mM chloride ions. In a particular embodiment, the composition contains no more than 10 mM of an alkali metal cation. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a more specific embodiment, the present invention provides a storage stable immunoglobulin composition consisting of: an immunoglobulin; no more than 10 mM of an alkali metal cation; a histidine/pH combination selected from the group consisting of variations 1 to 952, as provided in Table 1 and Table 2; and between 100 mM and 200 mM chloride ions. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

4. Immunoglobulin Concentration

Generally, the histidine formulations provided herein are useful for stabilizing immunoglobulin compositions having a wide range of protein concentrations. For example, the histidine formulations provided herein are well suited to stabilize: low immunoglobulin concentrations that are used in the pharmaceutical formulation of monoclonal antibodies (e.g., 10-40 g/L or lower); moderate immunoglobulin concentrations that are used in the pharmaceutical formulation of intravenous immunoglobulins (e.g., 40-150 g/L); and high immunoglobulin concentration that are used in the pharmaceutical formulation of immunoglobulins administered subcutaneously or intramuscularly (e.g., 150-250 g/L or higher) Generally, the upper limit of immunoglobulin concentrations that may be stabilized by the methods and formulations provided herein is only limited by the solubility limit of the immunoglobulins being formulated or the maximum concentration that can be achieved by the particular manufacturing process being employed. Accordingly, in one embodiment, the immunoglobulin concentration of a storage stable aqueous solution provided herein is between 1 g/L and 250 g/L.

a. Low Immunoglobulin Concentration

In one embodiment, the present invention provides a storage stable, low concentration immunoglobulin aqueous composition comprising: less than 40 g/L of an immunoglobulin; between 50 mM and 500 mM histidine; no more than 10 mM of an alkali metal cation; and a pH between 5.5 and 7.0. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a particular embodiment, the present invention provides a storage stable, low concentration immunoglobulin aqueous composition comprising: less than 40 g/L of an immunoglobulin; no more than 10 mM of an alkali metal cation; and a histidine/pH combination selected from the group consisting of variations 1 to 952, as provided in Table 1 and Table 2. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a specific embodiment, the present invention provides a storage stable, low concentration immunoglobulin aqueous composition consisting essentially of: less than 40 g/L of an immunoglobulin and a histidine/pH combination selected from the group consisting of variations 1 to 952, as provided in Table 1 and Table 2. In one embodiment, the composition contains no more than 10 mM of an alkali metal cation. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a more specific embodiment, the present invention provides a storage stable, low concentration immunoglobulin aqueous composition consisting of: less than 40 g/L of an immunoglobulin; no more than 10 mM of an alkali metal cation; and a histidine/pH combination selected from the group consisting of variations 1 to 952, as provided in Table 1 and Table 2. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a specific embodiment, the concentration of the immunoglobulin in the storage stable, low concentration immunoglobulin aqueous composition is between 10 g/L and 40 g/L. In another embodiment, the concentration of the immunoglobulin is between 20 g/L and 30 g/L. In one embodiment, the concentration of the immunoglobulin is less than 40 g/L. In one embodiment, the concentration of the immunoglobulin is no more than 40 g/L. In another embodiment, the concentration of the immunoglobulin is no more than 30 g/L. In another embodiment, the concentration of the immunoglobulin is no more than 20 g/L. In another embodiment, the concentration of the immunoglobulin is no more than 10 g/L. In a specific embodiment, the concentration of the immunoglobulin is 10±1 g/L, 15±1.5 g/L, 20±2 g/L, 25±2.5 g/L, 30±3 g/L, 35±3.5 g/L, or 40±4 g/L. In yet other embodiments, the concentration of the immunoglobulin is 1 g/L, 2 g/L, 3 g/L, 4 g/L, 5 g/L, 6 g/L, 7 g/L, 8 g/L, 9 g/L, 10 g/L. 11 g/L. 12 g/L. 13 g/L. 14 g/L. 15 g/L. 16 g/L. 17 g/L. 18 g/L. 19 g/L. 20 g/L. 21 g/L. 22 g/L. 23 g/L. 24 g/L. 25 g/L. 26 g/L. 27 g/L. 28 g/L. 29 g/L. 30 g/L, 31 g/L, 32 g/L, 33 g/L, 34 g/L, 35 g/L, 36 g/L, 37 g/L, 38 g/L, 39 g/L, or 40 g/L.

b. Moderate Immunoglobulin Concentration

In another embodiment, the present invention provides a storage stable immunoglobulin aqueous composition comprising: between 40 g/L and 150 g/L of an immunoglobulin; between 50 mM and 500 mM histidine; no more than 10 mM of an alkali metal cation; and a pH between 5.5 and 7.0. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. Ina specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a particular embodiment, the present invention provides a storage stable immunoglobulin aqueous composition comprising: between 40 g/L and 150 g/L of an immunoglobulin; no more than 10 mM of an alkali metal cation; and a histidine/pH combination selected from the group consisting of variations 1 to 952, as provided in Table 1 and Table 2. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a specific embodiment, the present invention provides a storage stable immunoglobulin aqueous composition consisting essentially of: between 40 g/L and 150 g/L of an immunoglobulin and a histidine/pH combination selected from the group consisting of variations 1 to 952, as provided in Table 1 and Table 2. In one embodiment, the composition contains no more than 10 mM of an alkali metal cation. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a more specific embodiment, the present invention provides a storage stable immunoglobulin aqueous composition consisting of: between 40 g/L and 150 g/L of an immunoglobulin; no more than 10 mM of an alkali metal cation; and a histidine/pH combination selected from the group consisting of variations 1 to 952, as provided in Table 1 and Table 2. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a specific embodiment the concentration of the immunoglobulin in the storage stable immunoglobulin aqueous composition is between 40 g/L and 60 g/L. In another specific embodiment, the concentration of the immunoglobulin is between 90 g/L and 110 g/L. In certain embodiments, the concentration of the immunoglobulin is 45±4.5 g/L, 50±5 g/L, 55±5.5 g/L, 60±6 g/L, 65±6.5 g/L, 70±7 g/L, 75±7.5 g/L, 80±8 g/L, 85±8.5 g/L, 90±9 g/L, 95±9.5 g/L, 100±10 g/L, 110±11 g/L, 120±12 g/L, 130±13 g/L, 140±14 g/L, or 150±15 g/L. In yet other embodiments, the concentration of the immunoglobulin is 40 g/L, 45 g/L, 50 g/L, 55 g/L, 60 g/L, 65 g/L, 70 g/L, 75 g/L, 80 g/L, 85 g/L, 90 g/L, 95 g/L, 100 g/L, 105 g/L, 110 g/L, 115 g/L, 120 g/L, 125 g/L, 130 g/L, 135 g/L, 140 g/L, 145 g/L, or 150 g/L.

c. High Immunoglobulin Concentration

In one embodiment, the present invention provides a storage stable, high concentration immunoglobulin aqueous composition comprising: more than 150 g/L of an immunoglobulin; between 50 mM and 500 mM histidine; no more than 10 mM of an alkali metal cation; and a pH between 5.5 and 7.0. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a particular embodiment, the present invention provides a storage stable, high concentration immunoglobulin aqueous composition comprising: more than 150 g/L of an immunoglobulin; no more than 10 mM of an alkali metal cation; and a histidine/pH combination selected from the group consisting of variations 1 to 952, as provided in Table 1 and Table 2. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a specific embodiment, the present invention provides a storage stable, high concentration immunoglobulin aqueous composition consisting essentially of: more than 150 g/L of an immunoglobulin and a histidine/pH combination selected from the group consisting of variations 1 to 952, as provided in Table 1 and Table 2. In one embodiment, the composition contains no more than 10 mM of an alkali metal cation. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a more specific embodiment, the present invention provides a storage stable, high concentration immunoglobulin aqueous composition consisting of: more than 150 g/L of an immunoglobulin; no more than 10 mM of an alkali metal cation; and a histidine/pH combination selected from the group consisting of variations 1 to 952, as provided in Table 1 and Table 2. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In one embodiment, the concentration of the immunoglobulin in the storage stable, high concentration immunoglobulin aqueous composition is at least 150 g/L. In a specific embodiment, the concentration of immunoglobulin is at least 175 g/L. In another specific embodiment, the concentration of immunoglobulin is at least 200 g/L. In another specific embodiment, the concentration of immunoglobulin is at least 225 g/L. In one embodiment, the concentration of the immunoglobulin is between 150 g/L and 250 g/L. In another embodiment, the concentration of the immunoglobulin is between 175 g/L and 225 g/L In certain embodiments, the concentration of immunoglobulin is 150±15 g/L, 160±16 g/L, 170±17 g/L, 180±18 g/L, 190±19 g/L, 200±20 g/L, 210±21 g/L, 220±22 g/L, 230±23 g/L, 240±24 g/L, or 250±25 g/L. In yet other embodiments, the concentration of the immunoglobulin is 150 g/L, 160 g/L, 170 g/L, 180 g/L, 190 g/L, 200 g/L, 210 g/L, 220 g/L, 230 g/L, 240 g/L, 250 g/L, or higher.

5. Administration

In certain embodiments, the storage stable compositions provided herein will be formulated for parenteral administration including, but not limited to, intradermal, subcutaneous, transdermal implant, intracavernous, intravitreal, transscleral, intracerebral, intrathecal, epidural, intravenous, intracardiac, intramuscular, intraosseous, intraperitoneal, and nanocell injection administration. In one preferred embodiment, the compositions provided herein will be formulated for intravenous administration. In another preferred embodiment, the compositions provided herein will be formulated for subcutaneous administration. In yet another preferred embodiment, the compositions provided herein will be formulated for intramuscular administration. In yet another embodiment, the formulation is suitable for intravenous administration as well as either or both subcutaneous and intramuscular administration.

6. Excipients

In certain embodiments, the storage stable immunoglobulin aqueous compositions provided herein further comprise one or more excipients. Non-limiting examples of excipients that can be included in the formulations provided herein include non-ionic surfactants, bulking agents (e.g., sugars and sugar alcohols), antioxidants, polysaccharides, and pharmaceutically acceptable water-soluble polymers (e.g., poly (acrylic acid), poly(ethylene oxide), poly(ethylene glycol), poly(vinyl pyrrolidone), hydroxyethyl cellulose, hydroxypropyl cellulose, and starch).

In one embodiment, the excipient is an agent for adjusting the osmolarity of the composition. Non-limiting examples of osmolarity agents include mannitol, sorbitol, glycerol, sucrose, glucose, dextrose, levulose, fructose, lactose, polyethylene glycols, phosphates, calcium chloride, calcium gluconoglucoheptonate, dimethyl sulfone, and the like.

In one embodiment, the present invention provides a storage stable immunoglobulin aqueous composition comprising: an immunoglobulin; between 50 mM and 500 mM histidine; no more than 10 mM of an alkali metal cation; an antioxidant; and a pH between 5.5 and 7.0. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a particular embodiment, the present invention provides a storage stable immunoglobulin aqueous composition comprising: an immunoglobulin; no more than 10 mM of an alkali metal cation; an antioxidant; and a histidine/pH combination selected from the group consisting of variations 1 to 952, as provided in Table 1 and Table 2. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a specific embodiment, the present invention provides a storage stable, low concentration immunoglobulin aqueous composition consisting essentially of: an immunoglobulin; an antioxidant; and a histidine/pH combination selected from the group consisting of variations 1 to 952, as provided in Table 1 and Table 2. In a specific embodiment, the composition contains no more than 10 mM of an alkali metal cation. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In a more specific embodiment, the present invention provides a storage stable immunoglobulin aqueous composition consisting of: an immunoglobulin; no more than 10 mM of an alkali metal cation; an antioxidant; and a histidine/pH combination selected from the group consisting of variations 1 to 952, as provided in Table 1 and Table 2. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a specific embodiment, the final composition does not contain a surfactant or sugar.

In one embodiment, the present invention provides a storage stable immunoglobulin aqueous composition comprising: an immunoglobulin; between 50 mM and 500 mM histidine; no more than 10 mM of an alkali metal cation; a sugar and/or sugar alcohol, and a pH between 5.5 and 7.0. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide.

In a particular embodiment, the present invention provides a storage stable immunoglobulin aqueous composition comprising: an immunoglobulin; no more than 10 mM of an alkali metal cation; a sugar and/or sugar alcohol; and a histidine/pH combination selected from the group consisting of variations 1 to 952, as provided in Table 1 and Table 2. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide.

In a specific embodiment, the present invention provides a storage stable, low concentration immunoglobulin aqueous composition consisting essentially of: an immunoglobulin; a sugar and/or sugar alcohol; and a histidine/pH combination selected from the group consisting of variations 1 to 952, as provided in Table 1 and Table 2. In a specific embodiment, the composition contains no more than 10 mM of an alkali metal cation. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide.

In a more specific embodiment, the present invention provides a storage stable immunoglobulin aqueous composition consisting of: an immunoglobulin; no more than 10 mM of an alkali metal cation; a sugar and/or sugar alcohol; and a histidine/pH combination selected from the group consisting of variations 1 to 952, as provided in Table 1 and Table 2. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide.

B. Plasma-Derived Immunoglobulins

Preparations of concentrated immunoglobulins (especially IgG) isolated from pooled human plasma are used for treating a variety of medical conditions, including immune deficiencies, inflammatory and autoimmune diseases, and acute infections. One IgG product, intravenous immunoglobulin or IVIG, is formulated for intravenous administration, for example, at a concentration of at or about 10% IgG. Concentrated immunoglobulins may also be formulated for subcutaneous or intramuscular administration, for example, at a concentration at or about 20% IgG.

Generally, plasma-derived immunoglobulin preparations formulated according to the present invention can be prepared from any suitable starting materials, for example, recovered plasma or source plasma. In a typical example, blood or plasma is collected from healthy donors. Immunoglobulins are isolated from the blood or plasma by suitable procedures, such as, for example, precipitation (alcohol fractionation or polyethylene glycol fractionation), chromatographic methods (ion exchange chromatography, affinity chromatography, immunoaffinity chromatography, etc.) ultracentrifugation, and electro-phoretic preparation, and the like. (See, e.g., Cohn et al., J. Am. Chem. Soc. 68:459-75 (1946); Oncley et al., J. Am. Chem. Soc. 71:541-50 (1949); Barandun et al., Vox Sang. 7:157-74 (1962); Koblet et al., Vox Sang. 13:93-102 (1967); U.S. Pat. Nos. 5,122,373 and 5,177,194; PCT/US10/36470; and WO 2010/138736 the disclosures of which are hereby incorporated by reference in their entireties for all purposes).

In many cases, immunoglobulins are prepared from gamma globulin-containing compositions produced by alcohol fractionation and/or ion exchange and affinity chromatography methods well known to those skilled in the art. For example, purified Cohn Fraction II is commonly used as a starting point for the further purification of immunoglobulins. The starting Cohn Fraction II paste is typically about 95 percent IgG and is comprised of the four IgG subtypes. The different subtypes are present in Fraction II in approximately the same ratio as they are found in the pooled human plasma from which they are obtained. The Fraction II is further purified before formulation into an administrable product. For example, the Fraction II paste can be dissolved in a cold purified aqueous alcohol solution and impurities removed via precipitation and filtration. Following the final filtration, the immunoglobulin suspension can be dialyzed or diafiltered (e.g., using ultrafiltration membranes having a nominal molecular weight limit of less than or equal to 100,000 daltons) to remove the alcohol. The solution can be concentrated or diluted to obtain the desired protein concentration and can be further purified by techniques well known to those skilled in the art.

Furthermore, additional preparative steps can be used to enrich a particular isotype or subtype of immunoglobulin. For example, protein A, protein G or protein H sepharose chromatography can be used to enrich a mixture of immunoglobulins for IgG, or for specific IgG subtypes. See generally, Harlow and Lane, *Using Antibodies*, Cold Spring Harbor Laboratory Press (1999); Harlow and Lane, *Antibodies, A Laboratory Manual*, Cold Spring Harbor Laboratory Press (1988); and U.S. Pat. No. 5,180,810, the disclosures of which are hereby incorporated by reference in their entireties for all purposes.

As will be recognized by one of skill in the art, immunoglobulin compositions isolated from pooled plasma contain impurities carried over from the starting plasma. Typically, pharmaceutically acceptable plasma-derived immunoglobulin compositions will contain at least 90% immunoglobulins, preferably at least 95% immunoglobulins, more preferably at least 98% immunoglobulins; most preferably at least 99% immunoglobulins, expressed as a function of total protein content. For example, GAMMAGARD® LIQUID (Baxter International; Deerfield, Ill.) is a plasma-derived immunoglobulin composition formulated at 100 g/L protein. According to the specifications, at least 98% of the protein is immune globulin, the average immunoglobulin A (IgA) concentration is 37 μg/mL, and immunoglobulin M is present in trace amounts (GAMMAGARD® LIQUID Prescribing Information). Accordingly, unless otherwise specified, an immunoglobulin composition provided herein comprising; consisting essentially of; or consisting of "a plasma-derived immunoglobulin" may contain up to 10% plasma protein impurities carried through during the manufacturing process.

In a particular embodiment, the immunoglobulin composition isolated from pooled plasma comprises at least 90% IgG immunoglobulins. In a specific embodiment, the immunoglobulin composition isolated from pooled plasma comprises at least 95% IgG immunoglobulins. In a more specific embodiment, the immunoglobulin composition isolated from pooled plasma comprises at least 98% IgG immunoglobulins. In a yet more specific embodiment, the immunoglobulin composition isolated from pooled plasma comprises at least 99% IgG immunoglobulins. In certain embodiments, the IgG immunoglobulin composition isolated from pooled plasma further comprises IgA and/or IgM immunoglobulins.

In another embodiment, the immunoglobulin composition isolated from pooled plasma comprises at least 10% IgA. In a specific embodiment, the immunoglobulin composition isolated from pooled plasma comprises at least 25% IgA. In a more specific embodiment, immunoglobulin composition isolated from pooled plasma comprises at least 50% IgA. In yet other embodiments, the immunoglobulin composition isolated from pooled plasma comprises at least 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or more IgA. In certain embodiments, the IgA immunoglobulin composition isolated from pooled plasma further comprises IgG and/or IgM immunoglobulins.

In another embodiment, the immunoglobulin composition isolated from pooled plasma comprises at least 10% IgM. In a specific embodiment, the immunoglobulin composition isolated from pooled plasma comprises at least 25% IgM. In a more specific embodiment, immunoglobulin composition isolated from pooled plasma comprises at least 50% IgM. In yet other embodiments, the immunoglobulin composition isolated from pooled plasma comprises at least 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or more IgM. In certain embodiments, the IgM immunoglobulin composition isolated from pooled plasma further comprises IgG and/or IgA immunoglobulins.

In another embodiment, the storage stable, plasma derived immunoglobulin composition is a hyper-immune immunoglobulin preparation. For example, in certain embodiments, the hyper-immune preparation may be an anti-tetanus, anti-D, anti-varicella, anti-rabies, anti-CMV, anti-hepatitis A, or anti-hepatitis B immunoglobulin preparation.

Accordingly, in one embodiment, the present invention provides storage stable, aqueous immunoglobulin composition comprising: a plasma-derived immunoglobulin; between 50 mM and 500 mM histidine; no more than 10 mM of an alkali metal cation; and a pH between 5.5 and 7.0. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition.

In a particular embodiment, the storage stable, aqueous immunoglobulin composition comprises: a plasma-derived immunoglobulin; between 50 mM and 500 mM histidine; no more than 1 mM of an alkali metal cation; and a pH between 5.5 and 7.0. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

Advantageously, it has been found that the formulation of plasma-derived immunoglobulins with moderate concentrations of histidine (e.g., 50 mM to 500 mM) at mildly acidic to neutral pH stabilizes the immunoglobulin composition in the absence of traditional stabilizing and bulking agents, such as surfactants (e.g., non-ionic surfactants), sugars, and sugar alcohols.

Accordingly, in a specific embodiment, the present invention provides a storage stable, aqueous immunoglobulin composition comprising a plasma-derived immunoglobulin; between 50 mM and 500 mM histidine; no more than 1 mM of an alkali metal cation; no more than 0.01% of a surfactant; no more than 1 mM of a sugar; no more than 1 mM of a sugar alcohol; and a pH between 5.5 and 7.0. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In another specific embodiment, the present invention provides a storage stable, aqueous immunoglobulin composition consisting essentially of: a plasma-derived immunoglobulin; between 50 mM and 500 mM histidine; and a pH between 5.5 and 7.0. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

The storage stable plasma derived IgG aqueous compositions provided herein are stable at room temperature (i.e., 20° C. to 25° C.) for an extended period of time. For example, in one embodiment, the storage stable, aqueous IgG composition is stable for at least about 2 months. In another embodiment, the composition will be stable for at least about 3 months. In yet other embodiment, the composition will be stable for at least 1 about month, or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more months. In a preferred embodiment, the composition will be stable for at least about 6 months. In a more preferred embodiment, the composition will be stable for at least about 1 year. In a more preferred embodiment, the composition will be stable for at least about 2 years.

1. Histidine

In one embodiment, the concentration of histidine in a storage stable plasma-derived immunoglobulin composition provided herein is between 50 mM and 500 mM. In another embodiment, the concentration of histidine in the formulation will be between 100 mM and 400 mM. In another embodiment, the concentration of histidine in the formulation will be between 200 mM and 300 mM. In another embodiment, the concentration of histidine in the formulation will be between 225 mM and 275 mM. In another embodiment, the concentration of histidine in the formulation will be between 240 mM and 260 mM. In a particular embodiment, the concentration of histidine will be 250 mM. In certain other embodiments, the concentration of histidine in the formulation will be 50±5 mM, 75±7.5 mM, 100±10 mM, 125±12.5 mM, 150±15 mM, 175±17.5 mM, 200±20 mM, 225±22.5 mM, 250±25 mM, 275±27.5 mM, 300±30 mM, 325±32.5 mM, 350±35 mM, 375±37.5 mM, 400±40 mM, 425±42.5 mM, 450±45 mM, 475±47.5 mM, 500±50 mM or higher. In yet other embodiments, the concentration of histidine in the formulation will be 50 mM, 75 mM, 100 mM, 125 mM, 150 mM, 175 mM, 200 mM, 225 mM, 250 mM, 275 mM, 300 mM, 325 mM, 350 mM, 375 mM, 400 mM, 425 mM, 450 mM, 475 mM, 500 mM or higher.

Accordingly, in one embodiment, the present invention provides a storage stable, aqueous immunoglobulin composition comprising: a plasma-derived immunoglobulin; between 100 mM and 400 mM histidine; no more than 10 mM of an alkali metal cation; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a specific embodiment, the present invention provides a storage stable, aqueous immunoglobulin composition consisting essentially of: a plasma-derived immunoglobulin; between 100 mM and 400 mM histidine; and a pH between 5.5 and 7.0. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a more specific embodiment, the present invention provides a storage stable, aqueous immunoglobulin composition consisting of: a plasma-derived immunoglobulin; between 100 mM and 400 mM histidine; no more than 10 mM of an alkali metal cation; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In one embodiment, the present invention provides a storage stable, aqueous immunoglobulin composition comprising: a plasma derived immunoglobulin; between 200 mM and 300 mM histidine; no more than 10 mM of an alkali metal cation; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a specific embodiment, the present invention provides a storage stable, aqueous immunoglobulin composition consisting essentially of: a plasma-derived immunoglobulin; between 200 mM and 300 mM histidine; and a pH between 5.5 and 7.0. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a more specific embodiment, the present invention provides a storage stable, aqueous immunoglobulin composition consisting of: a plasma-derived immunoglobulin; between 200 mM and 300 mM histidine; no more than 10 mM of an alkali metal cation; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In one embodiment, the present invention provides a storage stable, aqueous immunoglobulin composition comprising: a plasma-derived immunoglobulin; between 225 mM and 275 mM histidine; no more than 10 mM of an alkali metal cation; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a specific embodiment, the present invention provides a storage stable, aqueous immunoglobulin composition consisting essentially of: a plasma-derived immunoglobulin; between 225 mM and 275 mM histidine; and a pH between 5.5 and 7.0. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a more specific embodiment, the present invention provides a storage stable, aqueous immunoglobulin composition consisting of: a plasma-derived immunoglobulin; between 225 mM and 275 mM histidine; no more than 10 mM of an alkali metal cation; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In one embodiment, the present invention provides a storage stable, aqueous immunoglobulin composition comprising: a plasma-derived immunoglobulin; between 240 mM and 260 mM histidine; no more than 10 mM of an alkali metal cation; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a specific embodiment, the present invention provides a storage stable, aqueous immunoglobulin composition consisting essentially of: a plasma-derived immunoglobulin; between 240 mM and 260 mM histidine; and a pH between 5.5 and 7.0. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a more specific embodiment, the present invention provides a storage stable, aqueous immunoglobulin composition consisting of: a plasma-derived immunoglobulin; between 240 mM and 260 mM histidine; no more than 10 mM of an alkali metal cation; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In one embodiment, the present invention provides a storage stable, aqueous immunoglobulin composition comprising: a plasma-derived immunoglobulin; 250 mM histidine; no more than 10 mM of an alkali metal cation; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a specific embodiment, the present invention provides a storage stable, aqueous immunoglobulin composition consisting essentially of: a plasma-derived immunoglobulin; 250 mM histidine; and a pH between 5.5 and 7.0. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a more specific embodiment, the present invention provides a storage stable, aqueous immunoglobulin composition consisting of: a plasma-derived immunoglobulin; 250 mM histidine; no more than 10 mM of an alkali metal cation; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

2. pH

In one embodiment, the present invention provides a storage stable, aqueous immunoglobulin composition comprising: a plasma-derived immunoglobulin; between 50 mM and 500 mM histidine; no more than 10 mM of an alkali metal cation; and a pH between 5.5 and 6.5. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a specific embodiment, the present invention provides a storage stable, aqueous immunoglobulin composition consisting essentially of: a plasma-derived immunoglobulin; between 50 mM and 500 mM histidine; and a pH between 5.5 and 6.5. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a more specific embodiment, the present invention provides a storage stable, aqueous immunoglobulin composition consisting of: a plasma-derived immunoglobulin; between 50 mM and 500 mM histidine; no more than 10 mM of an alkali metal cation; and a pH between 5.5 and 6.5. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In one embodiment, the present invention provides a storage stable, aqueous immunoglobulin composition comprising: a plasma-derived immunoglobulin; between 200 mM and 300 mM histidine; no more than 10 mM of an alkali metal cation; and a pH between 5.5 and 6.5. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a specific embodiment, the present invention provides a storage stable, aqueous immunoglobulin composition consisting essentially of: a plasma-derived immunoglobulin; between 200 mM and 300 mM histidine; and a pH between 5.5 and 6.5. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a more specific embodiment, the present invention provides a storage stable, aqueous immunoglobulin composition consisting of: a plasma-derived immunoglobulin; between 200 mM and 300 mM histidine; no more than 10 mM of an alkali metal cation; and a pH between 5.5 and 6.5. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In one embodiment, the present invention provides a storage stable, aqueous immunoglobulin composition comprising: a plasma-derived immunoglobulin; between 200 mM and 300 mM histidine; no more than 10 mM of an alkali metal cation; and a pH of 6.1±0.4. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a specific embodiment, the present invention provides a storage stable, aqueous immunoglobulin composition consisting essentially of: a plasma-derived immunoglobulin; between 200 mM and 300 mM histidine; and a pH of 6.1±0.4. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a more specific embodiment, the present invention provides a storage stable, aqueous immunoglobulin composition consisting of: a plasma-derived immunoglobulin; between 200 mM and 300 mM histidine; no more than 10 mM of an alkali metal cation; and a pH of 6.1±0.4. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In one embodiment, the present invention provides a storage stable, aqueous immunoglobulin composition comprising: a plasma-derived immunoglobulin; between 200 mM and 300 mM histidine; no more than 10 mM of an alkali metal cation; and a pH of 6.1±0.3. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a specific embodiment, the present invention provides a storage stable, aqueous immunoglobulin composition consisting essentially of: a plasma-derived immunoglobulin; between 200 mM and 300 mM histidine; and a pH of 6.1±0.3. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a more specific embodiment, the present invention provides a storage stable, aqueous immunoglobulin composition consisting of: a plasma-derived immunoglobulin; between 200 mM and 300 mM histidine; no more than 10 mM of an alkali metal cation; and a pH of 6.1±0.3. In a specific embodiment, the composition contains no more than 1 mM of an alkali metal cation. In one embodiment, the immunoglobulin composition is contained in an air-tight containment vessel under inert gas. In a specific embodiment, the composition is stored under-nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In one embodiment, the present invention provides a storage stable, aqueous immunoglobulin composition comprising: a plasma-derived immunoglobulin; between 200 mM and 300 mM histidine; no more than 10 mM of an alkali metal cation; and a pH of 6.1±0.2. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a specific embodiment, the present invention provides a storage stable, aqueous immunoglobulin composition consisting essentially of: a plasma-derived immunoglobulin; between 200 mM and 300 mM histidine; and a pH of 6.1±0.2. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a more specific embodiment, the present invention provides a storage stable, aqueous immunoglobulin composition consisting of: a plasma-derived immunoglobulin; between 200 mM and 300 mM histidine; no more than 10 mM of an alkali metal cation; and a pH of 6.1±0.2. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In one embodiment, the present invention provides a storage stable, aqueous immunoglobulin composition comprising: a plasma-derived immunoglobulin; between 200 mM and 300 mM histidine; no more than 10 mM of an alkali metal cation; and a pH of 6.1±0.1. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a specific embodiment, the present invention provides a storage stable, aqueous immunoglobulin composition consisting essentially of: a plasma-derived immunoglobulin; between 200 mM and 300 mM histidine; and a pH of 6.1±0.1. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a more specific embodiment, the present invention provides a storage stable, aqueous immunoglobulin composition consisting of: a plasma-derived immunoglobulin; between 200 mM and 300 mM histidine; no more than 10 mM of an alkali metal cation; and a pH of 6.1±0.1. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In one embodiment, the present invention provides a storage stable, aqueous immunoglobulin composition comprising: a plasma-derived immunoglobulin; between 200 mM and 300 mM histidine; no more than 10 mM of an alkali metal cation; and a pH of 6.1. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin Composition. In a specific embodiment, the final composition does not contain a surfactant or sugar.

In a specific embodiment, the present invention provides a storage stable, aqueous immunoglobulin composition consisting essentially of: a plasma-derived immunoglobulin; between 200 mM and 300 mM histidine; and a pH of 6.1. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a more specific embodiment, the present invention provides a storage stable, aqueous immunoglobulin composition consisting of: a plasma-derived immunoglobulin; between 200 mM and 300 mM histidine; no more than 10 mM of an alkali metal cation; and a pH of 6.1. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In one embodiment, the present invention provides a storage stable, aqueous immunoglobulin composition comprising: a plasma-derived immunoglobulin; no more than 10 mM of an alkali metal cation; and a histidine/pH combination selected from the group consisting of variations 1 to 952, as provided in Table 1 and Table 2. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a specific embodiment, the present invention provides a storage stable, aqueous immunoglobulin composition consisting essentially of: a plasma-derived immunoglobulin and a histidine/pH combination selected from the group consisting of variations 1 to 952, as provided in Table 1 and Table 2. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a more specific embodiment, the present invention provides a storage stable, aqueous immunoglobulin composition consisting of: a plasma-derived immunoglobulin; no more than 10 mM of an alkali metal cation; and a histidine/pH combination selected from the group consisting of variations 1 to 952, as provided in Table 1 and Table 2. In a particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

3. Counter Anions

In one embodiment, the present invention provides a storage stable immunoglobulin composition comprising: a plasma-derived immunoglobulin; between 50 mM and 500 mM histidine; no more than 10 mM of an alkali metal Cation; between 10 mM and 400 mM chloride ions; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a specific embodiment, the present invention provides a storage stable immunoglobulin composition consisting essentially of: a plasma-derived immunoglobulin; between 50 mM and 500 mM histidine; between 10 mM and 400 mM chloride ions; and a pH between 5.5 and 7.0. In a particular embodiment, the composition contains no more than 10 mM of an alkali metal cation. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a more specific embodiment, the present invention provides a storage stable immunoglobulin composition consisting of: a plasma-derived immunoglobulin; between 50 mM and 500 mM histidine; no more than 10 mM of an alkali metal cation; between 10 mM and 400 mM chloride ions; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In one embodiment, the present invention provides a storage stable immunoglobulin composition comprising: a plasma-derived immunoglobulin; between 50 mM and 500 mM histidine; no more than 10 mM of an alkali metal cation; between 100 mM and 200 mM chloride ions; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a specific embodiment, the present invention provides a storage stable immunoglobulin composition consisting essentially of: a plasma-derived immunoglobulin; between 50 mM and 500 mM histidine; between 100 mM and 200 mM chloride ions; and a pH between 5.5 and 7.0. In a particular embodiment, the composition contains no more than 10 mM of an alkali metal cation. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a more specific embodiment, the present invention provides a storage stable immunoglobulin composition consisting of: a plasma-derived immunoglobulin; between 50 mM and 500 mM histidine; no more than 10 mM of an alkali metal cation; between 100 mM and 200 mM chloride ions; and a pH between 5.5 and 7.0. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In one embodiment, the present invention provides a storage stable immunoglobulin composition comprising: a plasma-derived immunoglobulin; no more than 10 mM of an alkali metal cation; a histidine/pH combination selected from the group consisting of variations 1 to 952, as provided in Table 1 and Table 2; and between 10 mM and 400 mM chloride ions. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a specific embodiment, the present invention provides a storage stable immunoglobulin composition consisting essentially of: a plasma-derived immunoglobulin; a histidine/pH combination selected from the group consisting of variations 1 to 952, as provided in Table 1 and Table 2; and between 10 mM and 400 mM chloride ions. In a particular embodiment, the composition contains no more than 10 mM of an alkali metal cation. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a more specific embodiment, the present invention provides a storage stable immunoglobulin composition consisting of: a plasma-derived immunoglobulin; no more than 10 mM of an alkali metal cation; a histidine/pH combination selected from the group consisting of variations 1 to 952, as provided in Table 1 and Table 2; and between 10 mM and 400 mM chloride ions. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In one embodiment, the present invention provides a storage stable immunoglobulin composition comprising: a plasma-derived immunoglobulin; no more than 10 mM of an alkali metal cation; a histidine/pH combination selected from the group consisting of variations 1 to 952, as provided in Table 1 and Table 2; and between 100 mM and 200 mM chloride ions. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a specific embodiment, the present invention provides a storage stable immunoglobulin composition consisting essentially of: a plasma-derived immunoglobulin; a histidine/pH combination selected from the group consisting of variations 1 to 952, as provided in Table 1 and Table 2; and between 100 mM and 200 mM chloride ions. In a particular embodiment, the composition contains no more than 10 mM of an alkali metal cation. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a more specific embodiment, the present invention provides a storage stable immunoglobulin composition consisting of: a plasma-derived immunoglobulin; no more than 10 mM of an alkali metal cation; a histidine/pH combination selected from the group consisting of variations 1 to 952, as provided in Table 1 and Table 2; and between 100 mM and 200 mM chloride ions. In a specific embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

4. Immunoglobulin Concentration

Generally, the histidine formulations provided herein are useful for stabilizing plasma-derived immunoglobulin compositions having a wide range of protein concentrations. For example, the histidine formulations provided herein are well suited to stabilize: low immunoglobulin concentrations e.g., 10-40 g/L or lower); moderate immunoglobulin concentrations that are used in the pharmaceutical formulation of intravenous immunoglobulins (e.g., 40-150 g/L); and high immunoglobulin concentration that are used in the pharmaceutical formulation of immunoglobulins administered subcutaneously or intramuscularly (e.g., 150-250 g/L or higher). Generally, the upper limit of immunoglobulin concentrations that may be stabilized by the methods and formulations provided herein is only limited by the solubility limit of the immunoglobulins being formulated or the maximum concentration that can be achieved by the particular manufacturing process being employed. Accordingly, in one embodiment, the immunoglobulin concentration of a storage stable aqueous solution provided herein is between 1 g/L and 250 g/L. Immunoglobulin concentrations may be referred to in terms of g/L or percentage, with an immunoglobulin concentration of 10 g/L corresponding to a protein concentration of 1%.

a. Low Immunoglobulin Concentration

In one embodiment, the present invention provides a storage stable, low concentration immunoglobulin aqueous composition comprising: less than 40 g/L of a plasma-derived immunoglobulin; between 50 mM and 500 mM histidine; no more than 10 mM of an alkali metal cation; and a pH between 5.5 and 7.0. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a particular embodiment, the present invention provides a storage stable, low concentration immunoglobulin aqueous composition comprising: less than 40 g/L of a plasma-derived immunoglobulin; no more than 10 mM of an alkali metal cation; and a histidine/pH combination selected from the group consisting of variations 1 to 952, as provided in Table 1 and Table 2. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a specific embodiment, the present invention provides a storage stable, low concentration immunoglobulin aqueous composition consisting essentially of: less than 40 g/L of a plasma-derived immunoglobulin and a histidine/pH combination selected from the group consisting of variations 1 to 952, as provided in Table 1 and Table 2. In one embodiment, the composition contains no more than 10 mM of an alkali metal cation. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a more specific embodiment, the present invention provides a storage stable, low concentration immunoglobulin aqueous composition consisting of: less than 40 g/L of a plasma-derived immunoglobulin; no more than 10 mM of an alkali metal cation; and a histidine/pH combination selected from the group consisting of variations 1 to 952, as provided in Table 1 and Table 2. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

b. Moderate Immunoglobulin Concentration

In another embodiment, the present invention provides a storage stable immunoglobulin aqueous composition comprising: between 40 g/L and 150 g/L of a plasma-derived immunoglobulin; between 50 mM and 500 mM histidine; no more than 10 mM of an alkali metal cation; and a pH between 5.5 and 7.0. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a particular embodiment, the present invention provides a storage stable immunoglobulin aqueous composition comprising: between 40 g/L and 150 g/L of a plasma-derived immunoglobulin; no more than 10 mM of an alkali metal cation; and a histidine/pH combination selected from the group consisting of variations 1 to 952, as provided in Table 1 and Table 2. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a specific embodiment, the present invention provides a storage stable immunoglobulin aqueous composition consisting essentially of: between 40 g/L and 150 g/L of a plasma-derived immunoglobulin and a histidine/pH combination selected from the group consisting of variations 1 to 952, as provided in Table 1 and Table 2. In one embodiment, the composition contains no more than 10 mM of an alkali metal cation. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a more specific embodiment, the present invention provides a storage stable immunoglobulin aqueous composition consisting of: between 40 g/L and 150 g/L of a plasma-derived immunoglobulin; no more than 10 mM of an alkali metal cation; and a histidine/pH combination selected from the group consisting of variations 1 to 952, as provided in Table 1 and Table 2. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

c. High Immunoglobulin Concentration

In one embodiment, the present invention provides a storage stable, high concentration immunoglobulin aqueous composition comprising: more than 150 g/L of a plasma-derived immunoglobulin; between 50 mM and 500 mM histidine; no more than 10 mM of an alkali metal cation; and a pH between 5.5 and 7.0. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a particular embodiment, the present invention provides a storage stable, high concentration immunoglobulin aqueous composition comprising: more than 150 g/L of a plasma-derived immunoglobulin; no more than 10 mM of an alkali metal cation; and a histidine/pH combination selected from the group consisting of variations 1 to 952, as provided in Table 1 and Table 2. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a specific embodiment, the present invention provides a storage stable, high concentration immunoglobulin aqueous composition consisting essentially of: more than 150 g/L of a plasma-derived immunoglobulin and a histidine/pH combination selected from the group consisting of variations 1 to 952, as provided in Table 1 and Table 2. In one embodiment, the composition contains no more than 10 mM of an alkali metal cation. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

In a more specific embodiment, the present invention provides a storage stable, high concentration immunoglobulin aqueous composition consisting of: more than 150 g/L of a plasma-derived immunoglobulin; no more than 10 mM of an alkali metal cation; and a histidine/pH combination selected from the group consisting of variations 1 to 952, as provided in Table 1 and Table 2. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the plasma-derived immunoglobulin is an IgG-containing immunoglobulin composition. In a specific embodiment, the final composition does not contain a surfactant or sugar.

C. Recombinant Immunoglobulins

In one aspect, the present invention provides storage stable, recombinant immunoglobulin preparations. Methods for obtaining recombinant antibodies, such as recombinant human antibodies are well known in the art. For example, a desired human antibody having a binding activity for a desired antigen can be obtained by in vitro immunizing human lymphocytes with the desired antigen or a cell expressing the desired antigen and fusing the immunized lymphocytes to human myeloma cells. A desired human antibody can also be obtained by immunizing a transgenic animal having all human antibody gene repertoires with an antigen (see, International Publications Nos. WO 93/12227, WO 92/03918, WO 94/02602, WO 94/25585, WO 96/34096, WO 96/33735). Methods for obtaining a human antibody by panning using a human antibody library are also known. For example, phages binding to an antigen can be selected by expressing the variable regions of a human antibody as single chain antibody fragments (scFv) on phage surfaces by a phage display method. The DNA sequences encoding the variable regions of the human antibody binding to the antigen can be determined by analyzing the genes of the selected phages. A whole human antibody can be obtained by preparing a suitable expression vector containing the determined DNA sequences of the scFv fragments binding to the antigen. These methods have already been well known from WO 92/01047, WO 92/20791, WO 93/06213, WO 93/11236, WO 93/19172, WO 95/01438, and WO 95/15388.

Methods for the expression of recombinant immunoglobulins are also well known in the art. For example, recombinant antibodies can be expressed in tissue or cell culture after transforming a recombinant gene for the construct into a suitable host. Suitable eukaryotic cells for use as hosts include animal, plant and fungal cells. Known animal cells include (I) mammalian cells such as CHO, COS, myeloma, BHK (baby hamster kidney), HeLa and Vero cells; (2) amphibian cells such as *Xenopus oocytes*; or (3) insect sells such as sf9, sf21 and Tn5. Known plant cells include cells of *Nicotiana* such as *Nicotiana tabacum*, which can be used as callus cultures. Known fungi include yeasts such as *Saccharomyces* spp., e.g. *Saccharomyces serevisiae* and filamentous fungi such as *Aspergillus* spp., e.g. *Aspergillus niger*. Prokaryotic cells can be used as producing systems using bacterial cells. Known bacterial cells include *E. coli* and

*Bacillus subtilis.* Antibodies can be obtained by transforming these cells with an antibody gene of interest and culturing the transformed cells in vitro.

In one embodiment of the present invention, the media used to express a recombinant protein can be animal protein-free and chemically defined. Methods of preparing animal protein-free and chemically defined culture mediums are known in the art, for example in US 2008/0009040 and US 2007/0212770, which are both incorporated herein for all purposes. "Protein free" and related terms refers to protein that is from a source exogenous to or other than the cells in the culture, which naturally shed proteins during growth. In another embodiment, the culture medium is polypeptide free. In another embodiment, the culture medium is serum free. In another embodiment the culture medium is animal protein free. In another embodiment the culture medium is animal component free. In another embodiment, the culture medium contains protein, e.g., animal protein from serum such as fetal calf serum. In another embodiment, the culture has recombinant proteins exogenously added. In another embodiment, the proteins are from a certified pathogen free animal. The term "chemically defined" as used herein shall mean, that the medium does not comprise any undefined supplements, such as, for example, extracts of animal components, organs, glands, plants, or yeast. Accordingly, each component of a chemically defined medium is accurately defined. In a preferred embodiment, the media are animal-component free and protein free.

Typically a recombinant antibody formulated as provided herein is specific for a polypeptide associated with a disease or disorder. Non-limiting examples of such polypeptides include macrophage migration inhibitory factor (MIF), tissue factor pathway inhibitor (TFPI); alpha-1-antitrypsin; insulin A-chain; insulin B-chain; proinsulin; follicle stimulating hormone; calcitonin; luteinizing hormone; glucagon; clotting factors such as, Factor II (prothrombin), Factor III (platelet tissue factor), Factor V, Factor VII, Factor VIII, Factor IX, Factor X, Factor XI, Factor XII, Factor XIII, and von Willebrand factor; anti-clotting factors such as Antithrombin III (ATIII), Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-b; platelet-derived growth factor (PDGF); fibroblast growth factor such as aFGF and bFGF; epidermal growth factor (EGF); transforming growth factor (TGF) such as TGF-alpha and TGF-beta, including TGF-b1, TGF-b2, TGF-b3, TGF-b4, or TGF-b5; a tumor necrosis factor (TNF) such as TNF-alpha or TNF-beta; insulin-like growth factor-I and -II (IGF-I and IGF-II); des(1-3)-IGF-I (brain IGF-I), insulin-like growth factor binding proteins; CD proteins such as CD3, CD4, CD8, CD19, CD20, CD22 and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1, IL-2, IL-3, IL-4, IL-5, IL-6, IL-7, IL-8, IL-9 and IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

In one embodiment, the present invention provides storage stable, aqueous immunoglobulin composition comprising: a recombinant immunoglobulin; between 50 mM and 500 mM histidine; no more than 10 mM of an alkali metal cation; and a pH between 5.5 and 7.0. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the antibody is a recombinant anti-MIF antibody. In a specific embodiment, the final composition does not contain a surfactant or sugar.

In a particular embodiment, the storage stable, aqueous immunoglobulin composition comprises: a recombinant immunoglobulin; between 50 mM and 500 mM histidine; no more than 1 mM of an alkali metal cation; and a pH between 5.5 and 7.0. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the antibody is a recombinant anti-MIF antibody. In a specific embodiment, the final composition does not contain a surfactant or sugar.

In a specific embodiment, the present invention provides a storage stable, aqueous immunoglobulin composition comprising a recombinant immunoglobulin; between 50 mM and 500 mM histidine; no more than 1 mM of an alkali metal cation; no more than 0.01% of a surfactant; no more than 1 mM of a sugar; no more than 1 mM of a sugar alcohol; and a pH between 5.5 and 7.0. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the antibody is a recombinant anti-MIF antibody. In a specific embodiment, the final composition does not contain a surfactant or sugar.

In another specific embodiment, the present invention provides a storage stable, aqueous immunoglobulin composition consisting essentially of: a recombinant immunoglobulin; between 50 mM and 500 mM histidine; and a pH between 5.5 and 7.0. In a particular embodiment, the composition contains no more than 10 mM of an alkali metal cation. In another particular embodiment, the composition contains no more than 1 mM of an alkali metal cation. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the antibody is a recombinant anti-MIF antibody. In a specific embodiment, the final composition does not contain a surfactant or sugar.

In a more specific embodiment, the present invention provides a storage stable, aqueous immunoglobulin composition consisting of a recombinant immunoglobulin; between 50 mM and 500 mM histidine; no more than 1 mM of an alkali metal cation; no more than 0.01% of a surfactant; no more than 1 mM of a sugar; no more than 1 mM of a sugar alcohol; and a pH between 5.5 and 7.0. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the antibody is a recombinant anti-MIF antibody. In a specific embodiment, the final composition does not contain a surfactant or sugar.

In a particular embodiment, the present invention provides a storage stable immunoglobulin aqueous composition comprising: a recombinant immunoglobulin; no more than 10 mM of an alkali metal cation; and a histidine/pH combination selected from the group consisting of variations 1 to 952, as provided in Table 1 and Table 2. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the antibody is a recombinant anti-MIF antibody. In a specific embodiment, the final composition does not contain a surfactant or sugar.

In a specific embodiment, the present invention provides a storage stable immunoglobulin aqueous composition consisting essentially of: a recombinant immunoglobulin and a histidine/pH combination selected from the group consisting of variations 1 to 952, as provided in Table 1 and Table 2. In one embodiment, the composition contains no more than 10 mM of an alkali metal cation. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the antibody is a recombinant anti-MIF antibody. In a specific embodiment, the final composition does not contain a surfactant or sugar.

In a more specific embodiment, the present invention provides a storage stable immunoglobulin aqueous composition consisting of: a recombinant immunoglobulin; no more than 10 mM of an alkali metal cation; and a histidine/pH combination selected from the group consisting of variations 1 to 952, as provided in Table 1 and Table 2. In a specific embodiment, the composition contains no more than 1 mM of an alkali metal cation. In another specific embodiment, the composition further comprises between 10 mM and 400 mM chloride ions. In one embodiment, the immunoglobulin composition is contained in an air-tight containment vessel under inert gas. In a specific embodiment, the composition is stored under nitrogen. In another specific embodiment, the composition is stored under argon. In yet another specific embodiment, the composition is stored under carbon dioxide. In a particular embodiment, the antibody is a recombinant anti-MIF antibody. In a specific embodiment, the final composition does not contain a surfactant or sugar.

IV. Methods for Stabilizing Immunoglobulin Compositions

Among other aspects, the present invention provides methods for stabilizing immunoglobulin compositions for therapeutic administration. The following embodiments are based in part on the unexpected discovery that the formulation of immunoglobulins with histidine at mildly acidic to neutral pH stabilizes the immunoglobulins that are otherwise labile at these pH values, and/or labile when formulated with histidine at an acidic pH, and/or labile when formulated in the presence of alkali metal cations.

Any immunoglobulin may be stabilized by the methods provided herein. Non-limiting examples of immunoglobulin preparations that may be stabilized include, plasma-derived immunoglobulin preparations, recombinant polyclonal or monoclonal preparations, minibodies, diabodies, triabodies, antibody fragments such as Fv, Fab and F(ab)2 or fragmented antibodies such as monovalent or multivalent single chain Fvs (scFv, sc(Fv)2, minibodies, diabodies, and triabodies such as scFv dimers) in which the variable regions of an antibody are joined together via a linker such as a peptide linker, and the like. Recombinant antibodies include murine antibodies, rodent antibodies, human antibodies, chimeric human antibodies (e.g., human/murine chimeras), humanized antibodies (e.g., humanized murine antibodies), and the like. In preferred embodiments, the recombinant antibody is a human, chimeric human, or humanized antibody suitable for administration to a human. In a preferred embodiment, the immunoglobulin in a full length, or near full length immunoglobulin, which will generally be more labile then engineered fragments thereof.

Generally, the methods provided herein stabilize immunoglobulin formulations at room temperature (i.e., between 20° C. and 25° C.) for an extended period of time. For example, in one embodiment, the methods stabilize an immunoglobulin composition stored at room temperature for at least about 2 months. In another embodiment, the methods stabilize an immunoglobulin composition stored at room temperature for at least about 3 months. In yet other embodiment, the methods stabilize an immunoglobulin composition stored at room temperature for at least 1 about month, or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more months. In a preferred embodiment, the methods stabilize an immunoglobulin composition stored at room temperature for at least about 6 months. In a more preferred embodiment, methods stabilize an immunoglobulin composition stored at room temperature for at least about 1 year. In a more preferred embodiment, methods stabilize an immunoglobulin composition stored at room temperature for at least about 2 years.

In one embodiment, the methods stabilize an immunoglobulin composition for at least six months when stored at a temperature between about 28° C. and about 32° C. In a specific embodiment, the methods stabilize an immunoglobulin composition for at least one year when stored at a temperature between about 28° C. and about 32° C. In a more specific embodiment, the methods stabilize an immunoglobulin composition for at least two years when stored at a temperature between about 28° C. and about 32° C. In another embodiment, the methods stabilize an immunoglobulin composition for at least six months when stored at a temperature between about 38° C. and about 42° C. In a specific embodiment, the methods stabilize an immunoglobulin composition for at least one year when stored at a temperature between about 38° C. and about 42° C. In a more specific embodiment, the methods stabilize an immunoglobulin composition for at least two years when stored at a temperature between about 38° C. and about 42° C.

In certain embodiments, the methods provided herein further comprise dispensing the composition into a sterile containment vessel and sealing the vessel air-tight, for example, using a rubber stopper. Immunoglobulin compositions in the air-tight vessels are preferably protected from ambient light by storage in a dark place, the use of a tinted vessel material (typically glass or plastic), and/or covering the surface of the vessel with an opaque substance.

In certain embodiments, the methods further comprise filling the headspace in the containment vessel with an inert gas (i.e., replacing the headspace air in the containment vessel with an inert gas). The inert gas helps to maintain an inert atmosphere above the liquid composition. When an immunoglobulin composition is stored in a vessel in which the headspace air has been replaced with an inert gas, the composition is said to be "stored under inert gas." Accordingly, in one embodiment, the methods provided herein comprise a step of storing the storage stable immunoglobulin composition under inert gas. Non-limiting examples of inert gasses than may be used in conjunction with the methods of the present invention include, nitrogen, argon, and carbon dioxide. In one particular embodiment, the inert gas is nitrogen. In another particular embodiment, the inert gas is argon. In yet another particular embodiment, the inert gas is carbon dioxide.

A. General Immunoglobulin Formulations

In one embodiment, the present invention provides a method for stabilizing an aqueous immunoglobulin composition, the method comprising formulating an immunoglobulin composition with between 50 mM and 500 mM histidine; no more than 10 mM of an alkali metal cation; and a pH between 5.5 and 7.0. In one embodiment, method further comprises storing the immunoglobulin composition in an air-tight containment vessel under an inert gas. In a specific embodiment, the inert gas is nitrogen. In another specific embodiment, the inert gas is argon. In yet another specific embodiment, the inert gas is carbon dioxide. In a specific embodiment, the final formulation does not contain a surfactant or sugar.

In a particular embodiment, the present invention provides a method for stabilizing an aqueous immunoglobulin composition, the method comprising formulating an immunoglobulin composition with: between 50 mM and 500 mM histidine; no more than 1 mM of an alkali metal cation; and a pH between 5.5 and 7.0. In one embodiment, method further comprises storing the immunoglobulin composition in an air-tight containment vessel under inert gas. In a specific embodiment, the inert gas is nitrogen. In another specific embodiment, the inert gas is argon. In yet another specific embodiment, the inert gas is carbon dioxide. In a specific embodiment, the final formulation does not contain a surfactant or sugar.

In a specific embodiment, the final formulation comprises: an immunoglobulin; between 50 mM and 500 mM histidine; no more than 1 mM of an alkali metal cation; no more than 0.01% of a surfactant; no more than 1 mM of a sugar; no more than 1 mM of a sugar alcohol; and a pH between 5.5 and 7.0. In a specific embodiment, the final formulation does not contain a surfactant or sugar.

In another specific embodiment, the final formulation consists essentially of: an immunoglobulin; between 50 mM and 500 mM histidine; and a pH between 5.5 and 7.0. In a particular embodiment, the composition contains no more than 10 mM of an alkali metal cation. In another particular embodiment, the formulation contains no more than 1 mM of an alkali metal cation. In a specific embodiment, the final formulation does not contain a surfactant or sugar.

In a more specific embodiment, the present invention provides a method for stabilizing an aqueous immunoglobulin composition, the method comprising formulating an immunoglobulin composition with: between 50 mM and 500 mM histidine; no more than 1 mM of an alkali metal cation; no more than 0.01% of a surfactant; no more than 1 mM of a sugar; no more than 1 mM of a sugar alcohol; and a pH between 5.5 and 7.0. In one embodiment, method further comprises storing the immunoglobulin composition in an air-tight containment vessel under inert gas. In a specific embodiment, the inert gas is nitrogen. In another specific embodiment, the inert gas is argon. In yet another specific embodiment, the inert gas is carbon dioxide. In a specific embodiment, the final formulation does not contain a surfactant or sugar.

The methods provided by the present invention may be used to stabilize any immunoglobulin composition, including but not limited to: immunoglobulin compositions isolated from pooled plasma (e.g., human pooled plasma); immunoglobulin compositions isolated from mammary secretions; immunoglobulin compositions isolated from avian sources (e.g., IgY containing compositions isolated from the yolk of chicken eggs); and recombinant immunoglobulins (e.g., monoclonal or polyclonal antibodies).

1. Histidine

Accordingly, in one embodiment, the present invention provides a method for stabilizing an aqueous immunoglobulin composition, the method comprising formulating an immunoglobulin composition with: between 100 mM and 400 mM histidine; no more than 10 mM of an alkali metal cation; and a pH between 5.5 and 7.0. In a specific embodiment, the final formulation contains no more than 1 mM of an alkali metal cation. In one embodiment, method further comprises storing the immunoglobulin composition in an air-tight containment vessel under inert gas. In a specific embodiment, the inert gas is nitrogen. In another specific embodiment, the inert gas is argon. In yet another specific embodiment, the inert gas is carbon dioxide. In a specific embodiment, the final formulation does not contain a surfactant or sugar.

In a specific embodiment, the final formulation consists essentially of: an immunoglobulin; between 100 mM and 400 mM histidine; and a pH between 5.5 and 7.0. In a particular embodiment, the final formulation contains no more than 10 mM of an alkali metal cation. In another particular embodiment, the final formulation contains no more than 1 mM of an alkali metal cation. In a specific embodiment, the final formulation does not contain a surfactant or sugar.

In a more specific embodiment, the final formulation consists of: an immunoglobulin; between 100 mM and 400 mM histidine; no more than 10 mM of an alkali metal cation; and a pH between 5.5 and 7.0. In a specific embodiment, the final formulation contains no more than 1 mM of an alkali metal cation. In a specific embodiment, the final formulation does not contain a surfactant or sugar.

In one embodiment, the final formulation comprises: an immunoglobulin; between 200 mM and 300 mM histidine; no more than 10 mM of an alkali metal cation; and a pH between 5.5 and 7.0. In a specific embodiment, the final formulation contains no more than 1 mM of an alkali metal cation. In a specific embodiment, the final formulation does not contain a surfactant or sugar.

In a specific embodiment, the final formulation consists essentially of: an immunoglobulin; between 200 mM and 300 mM histidine; and a pH between 5.5 and 7.0. In a particular embodiment, the final formulation contains no more than 10 mM of an alkali metal cation. In another particular embodiment, the final formulation contains no more than 1 mM of an alkali metal cation. In a specific embodiment, the final formulation does not contain a surfactant or sugar.

In a more specific embodiment, the final formulation consists of: an immunoglobulin; between 200 mM and 300 mM histidine; no more than 10 mM of an alkali metal cation; and a pH between 5.5 and 7.0. In a specific embodiment, the final formulation contains no more than 1 mM of an alkali metal cation. In a specific embodiment, the final formulation does not contain a surfactant or sugar.

In one embodiment, the final formulation comprises: an immunoglobulin; between 225 mM and 275 mM histidine; no more than 10 mM of an alkali metal cation; and a pH between 5.5 and 7.0. In a specific embodiment, the final formulation contains no more than 1 mM of an alkali metal cation. In a specific embodiment, the final formulation does not contain a surfactant or sugar.

In a specific embodiment, the final formulation consists essentially of: an immunoglobulin; between 225 mM and 275 mM histidine; and a pH between 5.5 and 7.0. In a particular embodiment, the final formulation contains no more than 10 mM of an alkali metal cation. In another particular embodiment, the final formulation contains no more than 1 mM of an alkali metal cation. In a specific embodiment, the final formulation does not contain a surfactant or sugar.

In a more specific embodiment, the final formulation consists of: an immunoglobulin; between 225 mM and 275 mM histidine; no more than 10 mM of an alkali metal cation; and a pH between 5.5 and 7.0. In a specific embodiment, the final formulation contains no more than 1 mM of an alkali metal cation. In a specific embodiment, the final formulation does not contain a surfactant or sugar.

In one embodiment, the final formulation comprises: an immunoglobulin; between 240 mM and 260 mM histidine; no more than 10 mM of an alkali metal cation; and a pH between 5.5 and 7.0. In a specific embodiment, the final formulation contains no more than 1 mM of an alkali metal cation.

In a specific embodiment, the final formulation consists essentially of: an immunoglobulin; between 240 mM and 260 mM histidine; and a pH between 5.5 and 7.0. In a particular embodiment, the final formulation contains no more than 10 mM of an alkali metal cation. In another particular embodiment, the final formulation contains no more than 1 mM of an alkali metal cation. In a specific embodiment, the final formulation does not contain a surfactant or sugar.

In a more specific embodiment, the final formulation consists of: an immunoglobulin; between 240 mM and 260 mM histidine; no more than 10 mM of an alkali metal cation; and a pH between 5.5 and 7.0. In a specific embodiment, the final formulation contains no more than 1 mM of an alkali metal cation. In a specific embodiment, the final formulation does not contain a surfactant or sugar.

In one embodiment, the final formulation comprises: an immunoglobulin; 250 mM histidine; no more than 10 mM of an alkali metal cation; and a pH between 5.5 and 7.0. In a specific embodiment, the final formulation contains no more than 1 mM of an alkali metal cation. In a specific embodiment, the final formulation does not contain a surfactant or sugar.

In a specific embodiment, the final formulation consists essentially of: an immunoglobulin; 250 mM histidine; and a pH between 5.5 and 7.0. In a particular embodiment, the final formulation contains no more than 10 mM of an alkali metal cation. In another particular embodiment, the final formulation contains no more than 1 mM of an alkali metal cation. In a specific embodiment, the final formulation does not contain a surfactant or sugar.

In a more specific embodiment, the final formulation consists of: an immunoglobulin; 250 mM histidine; no more than 10 mM of an alkali metal cation; and a pH between 5.5 and 7.0. In a specific embodiment, the final formulation contains no more than 1 mM of an alkali metal cation. In a specific embodiment, the final formulation does not contain a surfactant or sugar.

2. pH

The storage stable immunoglobulin compositions provided by the present invention are formulated at mildly acidic to neutral pH. Generally, this includes pH values between 5.5 and 7.0. In a preferred embodiment, the pH value is between 5.5 and 6.5. However, the range of pH values at which any individual immunoglobulin composition is stabilized by the inclusion of histidine in the formulation may vary, dependent upon the properties of the particular immunoglobulin.

For example, in one embodiment, the methods comprise formulating immunoglobulins at a pH between 5.5 and 7.0. In another embodiment, the methods comprise formulating immunoglobulins at a pH between 5.5 and 6.5. In other embodiments, the methods comprise formulating immunoglobulins at a pH between 6.0 and 7.0. In another embodiment, the methods comprise formulating immunoglobulins at a pH between 5.5 and 6.0. In one embodiment, the methods comprise formulating immunoglobulins at a pH between 6.0 and 6.5. In another embodiment, the methods comprise formulating immunoglobulins at a pH between 6.5 and 7.0. In another embodiment, the methods comprise formulating immunoglobulins at a pH of 6.0±4. In another embodiment, the methods comprise formulating immunoglobulins at a pH of 6.0±3. In another embodiment, the methods comprise formulating immunoglobulins at a pH of 6.0±2. In another embodiment, the methods comprise formulating immunoglobulins at a pH of 6.0±1. In another embodiment, the methods comprise formulating immunoglobulins at a pH of 6.1±5. In another embodiment, the methods comprise formulating immunoglobulins at a pH of 6.1±4. In another embodiment, the methods comprise formulating immunoglobulins at a pH of 6.1±3. In another embodiment, the methods comprise formulating immunoglobulins at a pH of 6.1±2. In another embodiment, the methods comprise formulating immunoglobulins at a pH of 6.1±1. In other embodiments, the methods comprise formulating immunoglobulins at a pH of 5.5±0.2, 5.6±0.2, 5.7±0.2, 5.8±0.2, 5.9±0.2, 6.0±0.2, 6.1±0.2, 6.2±0.2, 6.3±0.2, 6.4±0.2, 6.5±0.2, 6.6±0.2, 6.7±0.2, 6.8±0.2, 6.9±0.2, or 7.0±0.2. In other embodiments, the methods comprise formulating immunoglobulins at a pH of 5.5±0.1, or 5.6±0.1, 5.7±0.1, 5.8±0.1, 5.9±0.1, 6.0±0.1, 6.1±0.1, 6.2±0.1, 6.3±0.1, 6.4±0.1, 6.5±0.1, 6.6±0.1, 6.7±0.1, 6.8±0.1, 6.9±0.1, or 7.0±0.1. In yet other embodiments, the methods comprise formulating immunoglobulins at a pH of 5.5, or 5.6, 5.7, 5.8, 5.9, 6.0, 6.1, 6.2, 6.3, 6.4, 6.5, 6.6, 6.7, 6.8, 6.9, or 7.0.

Accordingly, in one embodiment, the present invention provides a method for stabilizing an aqueous immunoglobulin composition, the method comprising formulating an immunoglobulin composition with: between 50 mM and 500 mM histidine; no more than 10 mM of an alkali metal cation; and a pH between 5.5 and 6.5. In a specific embodiment, the final formulation contains no more than 1 mM of an alkali metal cation. In one embodiment, method further comprises storing the immunoglobulin composition in an air-tight containment vessel under inert gas. In a specific embodiment, the inert gas is nitrogen. In another specific embodiment, the inert gas is argon. In yet another specific embodiment, the inert gas is carbon dioxide. In a specific embodiment, the final formulation does not contain a surfactant or sugar.

In a specific embodiment, the final formulation consists essentially of: an immunoglobulin; between 50 mM and 500 mM histidine; and a pH between 5.5 and 6.5. In a particular embodiment, the final formulation contains no more than 10 mM of an alkali metal cation. In another particular embodiment, the final formulation contains no more than 1 mM of an alkali metal cation. In a specific embodiment, the final formulation does not contain a surfactant or sugar.

In a more specific embodiment, the final formulation consists of: an immunoglobulin; between 50 mM and 500 mM histidine; no more than 10 mM of an alkali metal cation; and a pH between 5.5 and 6.5. In a specific embodiment, the final formulation contains no more than 1 mM of an alkali metal cation. In a specific embodiment, the final formulation does not contain a surfactant or sugar.

In one embodiment, the final formulation comprises: an immunoglobulin; between 200 mM and 300 mM histidine; no more than 10 mM of an alkali metal cation; and a pH between 5.5 and 6.5. In a specific embodiment, the final formulation contains no more than 1 mM of an alkali metal cation. In a specific embodiment, the final formulation does not contain a surfactant or sugar.

In a specific embodiment, the final formulation consists essentially of: an immunoglobulin; between 200 mM and 300 mM histidine; and a pH between 5.5 and 6.5. In a particular embodiment, the final formulation contains no more than 10 mM of an alkali metal cation. In a specific embodiment, the final formulation does not contain a surfactant or sugar.

In a more specific embodiment, the final formulation consists of: an immunoglobulin; between 200 mM and 300 mM histidine; no more than 10 mM of an alkali metal cation; and a pH between 5.5 and 6.5. In a specific embodiment, the final formulation contains no more than 1 mM of an alkali metal cation. In a specific embodiment, the final formulation does not contain a surfactant or sugar.

In one embodiment, the final formulation comprises: an immunoglobulin; between 200 mM and 300 mM histidine; no more than 10 mM of an alkali metal cation; and a pH of 6.1±0.4. In a specific embodiment, the final formulation contains no more than 1 mM of an alkali metal cation. In a specific embodiment, the final formulation does not contain a surfactant or sugar.

In a specific embodiment, the final formulation consists essentially of: an immunoglobulin; between 200 mM and 300 mM histidine; and a pH of 6.1±0.4. In a particular embodiment, the final formulation contains no more than 10 mM of an alkali metal cation. In another particular embodiment, the final formulation contains no more than 1 mM of an alkali metal cation. In a specific embodiment, the final formulation does not contain a surfactant or sugar.

In a more specific embodiment, the final formulation consists of: an immunoglobulin; between 200 mM and 300 mM histidine; no more than 10 mM of an alkali metal cation; and a pH of 6.1±0.4. In a specific embodiment, the final formulation contains no more than 1 mM of an alkali metal cation. In a specific embodiment, the final formulation does not contain a surfactant or sugar.

In one embodiment, the final formulation comprises: an immunoglobulin; between 200 mM and 300 mM histidine; no more than 10 mM of an alkali metal cation; and a pH of 6.1±0.3. In a specific embodiment, the final formulation contains no more than 1 mM of an alkali metal cation. In a specific embodiment, the final formulation does not contain a surfactant or sugar.

In a specific embodiment, the final formulation consists essentially of: an immunoglobulin; between 200 mM and 300 mM histidine; and a pH of 6.1±0.3. In a particular embodiment, the final formulation contains no more than 10 mM of an alkali metal cation. In another particular embodiment, the final formulation contains no more than 1 mM of an alkali metal cation. In a specific embodiment, the final formulation does not contain a surfactant or sugar.

In a more specific embodiment, the final formulation consists of: an immunoglobulin; between 200 mM and 300 mM histidine; no more than 10 mM of an alkali metal cation; and a pH of 6.1±0.3. In a specific embodiment, the final formulation contains no more than 1 mM of an alkali metal cation. In a specific embodiment, the final formulation does not contain a surfactant or sugar.

In one embodiment, the final formulation comprises: an immunoglobulin; between 200 mM and 300 mM histidine; no more than 10 mM of an alkali metal cation; and a pH of 6.1±0.2. In a specific embodiment, the final formulation contains no more than 1 mM of an alkali metal cation. In a specific embodiment, the final formulation does not contain a surfactant or sugar.

In a specific embodiment, the final formulation consists essentially of: an immunoglobulin; between 200 mM and 300 mM histidine; and a pH of 6.1±0.2. In a particular embodiment, the final formulation contains no more than 10 mM of an alkali metal cation. In another particular embodiment, the final formulation contains no more than 1 mM of an alkali metal cation. In a specific embodiment, the final formulation does not contain a surfactant or sugar.

In a more specific embodiment, the final formulation consists of: an immunoglobulin; between 200 mM and 300 mM histidine; no more than 10 mM of an alkali metal cation; and a pH of 6.1±0.2. In a specific embodiment, the final formulation contains no more than 1 mM of an alkali metal cation. In a specific embodiment, the final formulation does not contain a surfactant or sugar.

In one embodiment, the final formulation comprises: an immunoglobulin; between 200 mM and 300 mM histidine; no more than 10 mM of an alkali metal cation; and a pH of 6.1±0.1. In a specific embodiment, the final formulation contains no more than 1 mM of an alkali metal cation. In a specific embodiment, the final formulation does not contain a surfactant or sugar.

In a specific embodiment, the final formulation consists essentially of: an -immunoglobulin; between 200 mM and 300 mM histidine; and a pH of 6.1±0.1. In a particular embodiment, the final formulation contains no more than 10 mM of an alkali metal cation. In another particular embodiment, the final formulation contains no more than 1 mM of an alkali metal cation. In a specific embodiment, the final formulation does not contain a surfactant or sugar.

In a more specific embodiment, the final formulation consists of: an immunoglobulin; between 200 mM and 300 mM histidine; no more than 10 mM of an alkali metal cation; and a pH of 6.1±0.1. In a specific embodiment, the final formulation contains no more than 1 mM of an alkali metal cation. In a specific embodiment, the final formulation does not contain a surfactant or sugar.

In one embodiment, the final formulation comprises: an immunoglobulin; between 200 mM and 300 mM histidine; no more than 10 mM of an alkali metal cation; and a pH of 6.1. In a specific embodiment, the final formulation contains no more than 1 mM of an alkali metal cation. In a specific embodiment, the final formulation does not contain a surfactant or sugar.

In a specific embodiment, the final formulation consists essentially of: an immunoglobulin; between 200 mM and 300 mM histidine; and a pH of 6.1. In a particular embodiment, the final formulation contains no more than 10 mM of an alkali metal cation. In another particular embodiment, the final formulation contains no more than 1 mM of an alkali metal cation. In a specific embodiment, the final formulation does not contain a surfactant or sugar.

In a more specific embodiment, the final formulation consists of: an immunoglobulin; between 200 mM and 300 mM histidine; no more than 10 mM of an alkali metal cation; and a pH of 6.1. In a specific embodiment, the final formulation contains no more than 1 mM of an alkali metal cation. In a specific embodiment, the final formulation does not contain a surfactant or sugar.

In certain embodiments, the method comprises formulating an immunoglobulin composition with a combination of histidine concentration and pH selected from any one of variations (Var.) 1 to 952, as provided in Table 1 and Table 2.

Accordingly, in one embodiment, the present invention provides a method for stabilizing an aqueous immunoglobulin composition, the method comprising formulating an immunoglobulin composition with: no more than 10 mM of an alkali metal cation; and a histidine/pH combination selected from the group consisting of variations 1 to 952, as provided in Table 1 and Table 2. In a specific embodiment, the final formulation contains no more than 1 mM of an alkali metal cation. In one embodiment, method further comprises storing the immunoglobulin composition in an air-tight containment vessel under inert gas. In a specific embodiment, the inert gas is nitrogen. In another specific embodiment, the inert gas is argon. In yet another specific embodiment, the inert gas is carbon dioxide. In a specific embodiment, the final formulation does not contain a surfactant or sugar.

In a specific embodiment, the final formulation consists essentially of: an immunoglobulin and a histidine/pH combination selected from the group consisting of variations 1 to 952, as provided in Table 1 and Table 2. In a particular embodiment, the final formulation contains no more than 10 mM of an alkali metal cation. In another particular embodiment, the final formulation contains no more than 1 mM of an alkali metal cation. In a specific embodiment, the final formulation does not contain a surfactant or sugar.

In a more specific embodiment, the final formulation consists of: an immunoglobulin; no more than 10 mM of an alkali metal cation; and a histidine/pH combination selected from the) group consisting of variations 1 to 952, as provided in Table 1 and Table 2. In a particular embodiment, the final formulation contains no more than 1 mM of an alkali metal cation. In a specific embodiment, the final formulation does not contain a surfactant or sugar.

3. Counter Anions

In one embodiment, the present invention provides a method for stabilizing an aqueous immunoglobulin composition, the method comprising formulating an immunoglobulin composition with: between 50 mM and 500 mM histidine; no more than 10 mM of an alkali metal cation; between 10 mM and 400 mM chloride ions; and a pH between 5.5 and 7.0. In a specific embodiment, the final formulation contains no more than 1 mM of an alkali metal cation. In one embodiment, method further comprises storing the immunoglobulin composition in an air-tight containment vessel under inert gas. In a specific embodiment, the inert gas is nitrogen. In another specific embodiment, the inert gas is argon. In yet another specific embodiment, the inert gas is carbon dioxide. In a specific embodiment, the final formulation does not contain a surfactant or sugar.

In a specific embodiment, the final formulation consists essentially of: an immunoglobulin; between 50 mM and 500 mM histidine; between 10 mM and 400 mM chloride ions; and a pH between 5.5 and 7.0. In a particular embodiment, the composition contains no more than 10 mM of an alkali metal cation. In a specific embodiment, the final formulation contains no more than 1 mM of an alkali metal cation. In a specific embodiment, the final formulation does not contain a surfactant or sugar.

In a more specific embodiment, the final formulation consists of: an immunoglobulin; between 50 mM and 500 mM histidine; no more than 10 mM of an alkali metal cation; between 10 mM and 400 mM chloride ions; and a pH between 5.5 and 7.0. In a specific embodiment, the final formulation contains no more than 1 mM of an alkali metal cation. In a specific embodiment, the final formulation does not contain a surfactant or sugar.

In one embodiment, the final formulation comprises: an immunoglobulin; between 50 mM and 500 mM histidine; no more than 10 mM of an alkali metal cation; between 100 mM and 200 mM chloride ions; and a pH between 5.5 and 7.0. In a specific embodiment, the final formulation contains no more than 1 mM of an alkali metal cation. In a specific embodiment, the final formulation does not contain a surfactant or sugar.

In a specific embodiment, the final formulation consists essentially of: an immunoglobulin; between 50 mM and 500 mM histidine; between 100 mM and 200 mM chloride ions; and a pH between 5.5 and 7.0. In a particular embodiment, the final formulation contains no more than 10 mM of an alkali metal cation. In a specific embodiment, the final formulation contains no more than 1 mM of an alkali metal cation. In a specific embodiment, the final formulation does not contain a surfactant or sugar.

In a more specific embodiment, the final formulation consists of: an immunoglobulin; between 50 mM and 500 mM histidine; no more than 10 mM of an alkali metal cation; between 100 mM and 200 mM chloride ions; and a pH between 5.5 and 7.0. In a specific embodiment, the final formulation contains no more than 1 mM of an alkali metal cation. In a specific embodiment, the final formulation does not contain a surfactant or sugar.

In one embodiment, the final formulation comprises: an immunoglobulin; no more than 10 mM of an alkali metal cation; a histidine/pH combination selected from the group consisting of variations 1 to 952, as provided in Table 1 and Table 2; and between 10 mM and 400 mM chloride ions. In a specific embodiment, the final formulation contains no more than 1 mM of an alkali metal cation. In a specific embodiment, the final formulation does not contain a surfactant or sugar.

In a specific embodiment, the final formulation consists essentially of: an immunoglobulin; a histidine/pH combination selected from the group consisting of variations 1 to 952, as provided in Table 1 and Table 2; and between 10 mM and 400 mM chloride ions. In a particular embodiment, the final formulation contains no more than 10 mM of an alkali metal cation. In a specific embodiment, the final formulation contains no more than 1 mM of an alkali metal cation. In a specific embodiment, the final formulation does not contain a surfactant or sugar.

In a more specific embodiment, the final formulation consists of: an immunoglobulin; no more than 10 mM of an alkali metal cation; a histidine/pH combination selected from the group consisting of variations 1 to 952, as provided in Table 1 and Table 2; and between 10 mM and 400 mM chloride ions. In a specific embodiment, the final formulation contains no more than 1 mM of an alkali metal cation. In a specific embodiment, the final formulation does not contain a surfactant or sugar.

In one embodiment, the final formulation comprises: an immunoglobulin; no more than 10 mM of an alkali metal cation; a histidine/pH combination selected from the group consisting of variations 1 to 952, as provided in Table 1 and Table 2; and between 100 mM and 200 mM chloride ions. In a specific embodiment, the final formulation contains no more than 1 mM of an alkali metal cation. In a specific embodiment, the final formulation does not contain a surfactant or sugar.

In a specific embodiment, the final formulation consists essentially of: an immunoglobulin; a histidine/pH combination selected from the group consisting of variations 1 to 952, as provided in Table 1 and Table 2; and between 100 mM and 200 mM chloride ions. In a particular embodiment, the final formulation contains no more than 10 mM of an alkali metal cation. In a specific embodiment, the final formulation contains no more than 1 mM of an alkali metal cation. In a specific embodiment, the final formulation does not contain a surfactant or sugar.

In a more specific embodiment, the final formulation consists of: an immunoglobulin; no more than 10 mM of an alkali metal cation; a histidine/pH combination selected from the group consisting of variations 1 to 952, as provided in Table 1 and Table 2; and between 100 mM and 200 mM chloride ions. In a specific embodiment, the final formulation contains no more than 1 mM of an alkali metal cation. In a specific embodiment, the final formulation does not contain a surfactant or sugar.

4. Immunoglobulin Concentration

Generally, the methods provided herein are useful for stabilizing immunoglobulin compositions having a wide range of protein concentrations. For example, the methods provided herein are well suited to stabilize: low immunoglobulin concentrations that are used in the pharmaceutical formulation of monoclonal antibodies (e.g., 10-40 g/L or lower); moderate immunoglobulin concentrations that are used in the pharmaceutical formulation of intravenous immunoglobulins (e.g., 40-150 g/L); and high immunoglobulin concentration that are used in the pharmaceutical formulation of immunoglobulins administered subcutaneously or intramuscularly (e.g., 150-250 g/L or higher). Generally, the upper limit of immunoglobulin concentrations that may be stabilized by the methods and formulations provided herein is only limited by the solubility limit of the immunoglobulins being formulated or the maximum concentration that can be achieved by the particular manufacturing process being employed. Accordingly, in one embodiment, the immunoglobulin concentration of a storage stable aqueous solution provided herein is between 1 g/L and 250 g/L.

a. Low Immunoglobulin Concentration

In one embodiment, the present invention provides a method for stabilizing an aqueous immunoglobulin composition, the method comprising formulating a composition comprising less than 40 g/L immunoglobulin with: between 50 mM and 500 mM histidine; no more than 10 mM of an alkali metal cation; and a pH between 5.5 and 7.0. In a specific embodiment, the final formulation contains no more than 1 mM of an alkali metal cation. In another specific embodiment, the final formulation further comprises between 10 mM and 400 mM chloride ions. In one embodiment, method further comprises storing the immunoglobulin composition in an air-tight containment vessel under inert gas. In a specific embodiment, the inert gas is nitrogen. In another specific embodiment, the inert gas is argon. In yet another specific embodiment, the inert gas is carbon dioxide. In a specific embodiment, the final formulation does not contain a surfactant or sugar.

In a particular embodiment, the final formulation comprises: less than 40 g/L of an immunoglobulin; no more than 10 mM of an alkali metal cation; and a histidine/pH combination selected from the group consisting of variations 1 to 952, as provided in Table 1 and Table 2. In a specific embodiment, the final formulation contains no more than 1 mM of an alkali metal cation. In another specific embodiment, the final formulation further comprises between 10 mM and 400 mM chloride ions. In a specific embodiment, the final formulation does not contain a surfactant or sugar.

In a specific embodiment, the final formulation consists essentially of: less than 40 g/L of an immunoglobulin and a histidine/pH combination selected from the group consisting of variations 1 to 952, as provided in Table 1 and Table 2. In one embodiment, the final formulation contains no more than 10 mM of an alkali metal cation. In a specific embodiment, the final formulation contains no more than 1 mM of an alkali metal cation. In another specific embodiment, the final formulation further comprises between 10 mM and 400 mM chloride ions.

In a more specific embodiment, the final formulation consists of: less than 40 g/L of an immunoglobulin; no more than 10 mM of an alkali metal cation; and a histidine/pH combination selected from the group consisting of variations 1 to 952, as provided in Table 1 and Table 2. In a specific embodiment, the final formulation contains no more than 1 mM of an alkali metal cation. In another specific embodiment, the final formulation further comprises between 10 mM and 400 mM chloride ions. In a specific embodiment, the final formulation does not contain a surfactant or sugar.

In a specific embodiment, the method comprises formulating the immunoglobulin at a concentration between 10 g/L and 40 g/L. In another embodiment, the concentration of the immunoglobulin is between 20 g/L and 30 g/L. In one embodiment, the concentration of the immunoglobulin is less than 40 g/L. In one embodiment, the concentration of the immunoglobulin is no more than 40 g/L. In another embodiment, the concentration of the immunoglobulin is no more than 30 g/L. In another embodiment, the concentration of the immunoglobulin is no more than 20 g/L. In another embodiment, the concentration of the immunoglobulin is no more than 10 g/L. In a specific embodiment, the concentration of the immunoglobulin is $10\pm1$ g/L, $15\pm1.5$ g/L, $20\pm2$ g/L, $25\pm2.5$ g/L, $30\pm3$ g/L, $35\pm3.5$ g/L, or $40\pm4$ g/L. In yet other embodiments, the concentration of the immunoglobulin is 1 g/L, 2 g/L, 3 g/L, 4 g/L, 5 g/L, 6 g/L, 7 g/L, 8 g/L, 9 g/L, 10 g/L. 11 g/L. 12 g/L. 13 g/L. 14 g/L. 15 g/L. 16 g/L. 17 g/L. 18 g/L. 19 g/L. 20 g/L. 21 g/L. 22 g/L. 23 g/L. 24 g/L. 25 g/L. 26 g/L. 27 g/L. 28 g/L. 29 g/L. 30 g/L, 31 g/L, 32 g/L, 33 g/L, 34 g/L, 35 g/L, 36 g/L, 37 g/L, 38 g/L, 39 g/L, or 40 g/L.

b. Moderate Immunoglobulin Concentration

In another embodiment, the present invention provides a method for stabilizing an aqueous immunoglobulin composition, the method comprising formulating a composition comprising between 40 g/L and 150 g/L immunoglobulin with: between 50 mM and 500 mM histidine; no more than 10 mM of an alkali metal cation; and a pH between 5.5 and 7.0. In a specific embodiment, the final formulation contains no more than 1 mM of an alkali metal cation. In another specific embodiment, the final formulation further comprises between 10 mM and 400 mM chloride ions. In one embodiment, method further comprises storing the immunoglobulin composition in an air-tight containment vessel under inert gas. In a specific embodiment, the inert gas is nitrogen. In another specific embodiment, the inert gas is argon. In yet another specific embodiment, the inert gas is carbon dioxide. In a specific embodiment, the final formulation does not contain a surfactant or sugar.

In a particular embodiment, the final formulation comprises: between 40 g/L and 150 g/L of an immunoglobulin; no more than 10 mM of an alkali metal cation; and a histidine/pH combination selected from the group consisting of variations 1 to 952, as provided in Table 1 and Table 2. In a specific embodiment, the final formulation contains no more than 1 mM of an alkali metal cation. In another specific embodiment, the final formulation further comprises between 10 mM and 400 mM chloride ions. In a specific embodiment, the final formulation does not contain a surfactant or sugar.

In a specific embodiment, the final formulation consists essentially of: between 40 g/L and 150 g/L of an immunoglobulin and a histidine/pH combination selected from the group consisting of variations 1 to 952, as provided in Table 1 and Table 2. In one embodiment, the final formulation contains no more than 10 mM of an alkali metal cation. In a specific embodiment, the final formulation contains no more than 1 mM of an alkali metal cation. In another specific embodiment, the final formulation further comprises between 10 mM and 400 mM chloride ions. In a specific embodiment, the final formulation does not contain a surfactant or sugar.

In a more specific embodiment, the final formulation consists of: between 40 g/L and 150 g/L of an immunoglobulin; no more than 10 mM of an alkali metal cation; and a histidine/pH combination selected from the group consisting of variations 1 to 952, as provided in Table 1 and Table 2. In a specific embodiment, the final formulation contains no more than 1 mM of an alkali metal cation. In another specific embodiment, the final formulation further comprises between 10 mM and 400 mM chloride ions. In a specific embodiment, the final formulation does not contain a surfactant or sugar.

In a specific embodiment, the method comprises formulating the immunoglobulin at a concentration between 40 g/L and 60 g/L. In another specific embodiment, the concentration of the immunoglobulin is between 90 g/L and 110 g/L. In certain embodiments, the concentration of the immunoglobulin is 45±4.5 g/L, 50±5 g/L, 55±5.5 g/L, 60±6 g/L, 65±6.5 g/L, 70±7 g/L, 75±7.5 g/L, 80±8 µg/L, 85±8.5 g/L, 90±9 g/L, 95±9.5 g/L, 100±10 g/L, 110±11 g/L, 120±12 g/L, 130±13 g/L, 140±14 g/L, or 150±15 g/L. In yet other embodiments, the concentration of the immunoglobulin is 40 g/L, 45 g/L, 50 g/L, 55 g/L, 60 g/L, 65 g/L, 70 g/L, 75 g/L, 80 g/L, 85 g/L, 90 g/L, 95 g/L, 100 g/L, 105 g/L, 110 g/L, 115 g/L, 120 g/L, 125 g/L, 130 g/L, 135 g/L, 140 g/L, 145 g/L, or 150 g/L.

c. High Immunoglobulin Concentration

In one embodiment, present invention provides a method for stabilizing an aqueous immunoglobulin composition, the method comprising formulating a composition comprising more than 150 g/L of an immunoglobulin with: between 50 mM and 500 mM histidine; no more than 10 mM of an alkali metal cation; and a pH between 5.5 and 7.0. In a specific embodiment, the final formulation contains no more than 1 mM of an alkali metal cation. In another specific embodiment, the final formulation further comprises between 10 mM and 400 mM chloride ions. In one embodiment, method further comprises storing the immunoglobulin composition in an air-tight containment vessel under inert gas. In a specific embodiment, the inert gas is nitrogen. In another specific embodiment, the inert gas is argon. In yet another specific embodiment, the inert gas is carbon dioxide. In a specific embodiment, the final formulation does not contain a surfactant or sugar.

In a particular embodiment, the final formulation comprises: more than 150 g/L of an immunoglobulin; no more than 10 mM of an alkali metal cation; and a histidine/pH combination selected from the group consisting of variations 1 to 952, as provided in Table 1 and Table 2. In a specific embodiment, the final formulation contains no more than 1 mM of an alkali metal cation. In another specific embodiment, the final formulation further comprises between 10 mM and 400 mM chloride ions. In a specific embodiment, the final formulation does not contain a surfactant or sugar.

In a specific embodiment, the final formulation consists essentially of: more than 150 g/L of an immunoglobulin and a histidine/pH combination selected from the group consisting of variations 1 to 952, as provided in Table 1 and Table 2. In one embodiment, the final formulation contains no more than 10 mM of an alkali metal cation. In a specific embodiment, the final formulation contains no more than 1 mM of an alkali metal cation. In another specific embodiment, the final formulation further comprises between 10 mM and 400 mM chloride ions. In a specific embodiment, the final formulation does not contain a surfactant or sugar.

In a more specific embodiment, the final formulation consists of: more than 150 g/L of an immunoglobulin; no more than 10 mM of an alkali metal cation; and a histidine/pH combination selected from the group consisting of variations 1 to 952, as provided in Table 1 and Table 2. In a specific embodiment, the final formulation contains no more than 1 mM of an alkali metal cation. In another specific embodiment, the final formulation further comprises between 10 mM and 400 mM chloride ions. In a specific embodiment, the final formulation does not contain a surfactant or sugar.

In a specific embodiment, the method comprises formulating the immunoglobulin at a concentration of at least 150 g/L. In a specific embodiment, the concentration of immunoglobulin is at least 175 g/L. In another specific embodiment, the concentration of immunoglobulin is at least 200 g/L. In another specific embodiment, the concentration of immunoglobulin is at least 225 g/L. In one embodiment, the concentration of the immunoglobulin is between 150 g/L and 250 g/L. In another embodiment, the concentration of the immunoglobulin is between 175 g/L and 225 g/L In certain embodiments, the concentration of the immunoglobulin is 150±15 g/L, 160±16 g/L, 170±17 g/L, 180±18 g/L, 190±19 g/L, 200±20 g/L, 210±21 g/L, 220±22 g/L, 230±23 g/L, 240±24 g/L, or 250±25 g/L. In yet other embodiments, the concentration of the immunoglobulin is 150 g/L, 160 g/L, 170 g/L, 180 g/L, 190 g/L, 200 g/L, 210 g/L, 220 g/L, 230 g/L, 240 g/L, 250 g/L, or higher.

5. Administration

In certain embodiments, the storage stable compositions provided herein will be formulated for parenteral administration including, but not limited to, intradermal, subcutaneous, transdermal implant, intracavernous, intravitreal, transscleral, intracerebral, intrathecal, epidural, intravenous, intracardiac, intramuscular, intraosseous, intraperitoneal, and nanocell injection administration. In one preferred embodiment, the compositions provided herein will be formulated for intravenous administration. In another preferred embodiment, the compositions provided herein will be formulated for subcutaneous administration. In yet another preferred embodiment, the compositions provided herein will be formulated for intramuscular administration. In yet another embodiment, the formulation is suitable for intravenous administration as well as either or both subcutaneous and intramuscular administration.

6. Excipients

In certain embodiments, the methods provided herein further comprise a formulation step of adding one or more excipients to the immunoglobulin composition. Non-limiting examples of excipients that can be included in the formulations provided herein include non-ionic surfactants, bulking agents (e.g., sugars and sugar alcohols), antioxidants, polysaccharides, and pharmaceutically acceptable water-soluble polymers (e.g., poly(acrylic acid), poly(ethylene oxide), poly(ethylene glycol), poly(vinyl pyrrolidone), hydroxyethyl cellulose, hydroxypropyl cellulose, and starch).

In one embodiment, the excipient is an agent for adjusting the osmolarity of the composition. Non-limiting examples of osmolarity agents include mannitol, sorbitol, glycerol, sucrose, glucose, dextrose, levulose, fructose, lactose, polyethylene glycols, phosphates, calcium chloride, calcium gluconoglucoheptonate, dimethyl sulfone, and the like.

In one embodiment, the present invention provides a method for stabilizing an aqueous immunoglobulin composition, the method comprising formulating an immunoglobulin composition with: between 50 mM and 500 mM histidine; no more than 10 mM of an alkali metal cation; an antioxidant; and a pH between 5.5 and 7.0. In a specific embodiment, the final formulation contains no more than 1 mM of an alkali metal cation. In another specific embodiment, the final formulation further comprises between 10 mM and 400 mM chloride ions. In one embodiment, method further comprises storing the immunoglobulin composition in an air-tight containment vessel under inert gas. In a specific embodiment, the inert gas is nitrogen. In another specific embodiment, the inert gas is argon. In yet another specific embodiment, the inert gas is carbon dioxide. In a specific embodiment, the final formulation does not contain a surfactant or sugar.

In a particular embodiment, the final formulation comprises: an immunoglobulin; no more than 10 mM of an alkali metal cation; an antioxidant; and a histidine/pH combination selected from the group consisting of variations 1 to 952, as provided in Table 1 and Table 2. In a specific embodiment, the final formulation contains no more than 1 mM of an alkali metal cation. In another specific embodiment, the final formulation further comprises between 10 mM and 400 mM chloride ions. In a specific embodiment, the final formulation does not contain a surfactant or sugar.

In a specific embodiment, the final formulation consists essentially of: an immunoglobulin; an antioxidant; and a histidine/pH combination selected from the group consisting of variations 1 to 952, as provided in Table 1 and Table 2. In a specific embodiment, the final formulation contains no more than 10 mM of an alkali metal cation. In a specific embodiment, the final formulation contains no more than 1 mM of an alkali metal cation. In another specific embodiment, the final formulation further comprises between 10 mM and 400 mM chloride ions. In a specific embodiment, the final formulation does not contain a surfactant or sugar.

In a more specific embodiment, the final formulation consists of: an immunoglobulin; no more than 10 mM of an alkali metal cation; an antioxidant; and a histidine/pH combination selected from the group consisting of variations 1 to 952, as provided in Table 1 and Table 2. In a specific embodiment, the final formulation contains no more than 1 mM of an alkali metal cation. In another specific embodiment, the final formulation further comprises between 10 mM and 400 mM chloride ions. In a specific embodiment, the final formulation does not contain a surfactant or sugar.

In one embodiment, the present invention provides a method for stabilizing an aqueous immunoglobulin composition, the method comprising formulating an immunoglobulin composition with: between 50 mM and 500 mM histidine; no more than 10 mM of an alkali metal cation; a sugar and/or sugar alcohol, and a pH between 5.5 and 7.0. In a specific embodiment, the final formulation contains no more than 1 mM of an alkali metal cation. In another specific embodiment, the final formulation further comprises between 10 mM and 400 mM chloride ions. In one embodiment, method further comprises storing the immunoglobulin composition in an air-tight containment vessel under inert gas. In a specific embodiment, the inert gas is nitrogen. In another specific embodiment, the inert gas is argon. In yet another specific embodiment, the inert gas is carbon dioxide.

In a particular embodiment, the final formulation comprises: an immunoglobulin; no more than 10 mM of an alkali metal cation; a sugar and/or sugar alcohol; and a histidine/pH combination selected from the group consisting of variations 1 to 952, as provided in Table 1 and Table 2. In a specific embodiment, the final formulation contains no more than 1 mM of an alkali metal cation. In another specific embodiment, the final formulation further comprises between 10 mM and 400 mM chloride ions.

In a specific embodiment, the final formulation consists essentially of: an immunoglobulin; a sugar and/or sugar alcohol; and a histidine/pH combination selected from the group consisting of variations 1 to 952, as provided in Table 1 and Table 2. In a specific embodiment, the final formulation contains no more than 10 mM of an alkali metal cation. In a specific embodiment, the final formulation contains no more than 1 mM of an alkali metal cation. In another specific embodiment, the final formulation further comprises between 10 mM and 400 mM chloride ions.

In a more specific embodiment, the final formulation consists of: an immunoglobulin; no more than 10 mM of an alkali metal cation; a sugar and/or sugar alcohol; and a histidine/pH combination selected from the group consisting of variations 1 to 952, as provided in Table 1 and Table 2. In a specific embodiment, the final formulation contains no more than 1 mM of an alkali metal cation. In another specific embodiment, the final formulation further comprises between 10 mM and 400 mM chloride ions.

V. Examples

Example 1

To determine the role pH and salt concentration have on a plasma-derived 20% IgG composition, a two year stability study was conducted. This study revealed that the inclusion of sodium chloride and/or the formulation at neutral to mildly acid pH imparted a stabilizing effect on the 20% IgG composition.

Briefly, two IgG compositions prepared from pooled plasma according to the Gammagard Liquid process outlined in Teschner et al. (Vox Sang. 2007 January; 92(1):42-55) were concentrated to a final protein concentration of 20%. These preparations were then divided into several samples which were differentially formulated at a pH of 6.5, 7.0, or 7.5 with and without approximately 50 mM sodium chloride. The aqueous formulations were then stored at between 28° C. and 32° C. for 24 months. After the two year incubation period, the molecular size distribution of the IgG in the various formulations was investigated by high performance size exclusion chromatography (HP-SEC), the results of which are provided in Table 3.

TABLE 3

Molecular size distribution of 20% IgG (IGSC61 and IGSC63) formulations after two years storage at 28° C. to 32° C.

| Sample | T (° C.) | | Polymers | Oligo/Dimers | Monomers | Fragments |
|---|---|---|---|---|---|---|
| | | IGSC61 | | | | |
| pH 6.5 | 24 months | 28-32 | 3.57 | 20.68 | 68.92 | 6.83 |
| pH 7.0 | 24 months | 28-32 | 10.32 | 19.78 | 60.96 | 8.94 |
| pH 7.5 | 24 months | 28-32 | 11.76 | 20.01 | 57.70 | 10.53 |
| pH 6.5 3 g/L NaCl | 24 months | 28-32 | 3.16 | 20.52 | 69.75 | 6.57 |
| pH 7.0 3 g/L NaCl | 24 months | 28-32 | 9.53 | 19.68 | 61.69 | 9.11 |
| pH 7.5 3 g/L NaCl | 24 months | 28-32 | 10.26 | 20.25 | 58.97 | 10.53 |
| | | IGSC63 | | | | |
| pH 6.5 | 24 months | 28-32 | 2.34 | 20.99 | 68.84 | 7.83 |
| pH 7.0 | 24 months | 28-32 | 3.48 | 20.95 | 64.37 | 11.20 |
| pH 7.5 | 24 months | 28-32 | 6.00 | 23.23 | 58.39 | 12.39 |
| pH 6.5 3 g/L NaCl | 24 months | 28-32 | 1.92 | 19.33 | 70.36 | 8.40 |
| pH 7.0 3 g/L NaCl | 24 months | 28-32 | 2.63 | 21.10 | 64.98 | 11.29 |
| pH 7.5 3 g/L NaCl | 24 months | 28-32 | 5.51 | 23.13 | 59.24 | 12.12 |

The results shown in Table 3 indicate that, within the pH range of 6.5 to 7.5, increases in pH result in increased aggregation of the IgG preparation, as shown by the increasing percentage of IgG polymers in the formulations at pH 7.0 and 7.5 compared to the formulations at pH 6.5. Inclusion of 50 mM sodium chloride in each formulation stabilizes the lower molecular weight IgG species, resulting in a nearly 14% reduction in the level of IgG polymers in the samples. This is in contrast to IgG compositions formulated as low pH (4.4 to 4.9), which are destabilized by the addition of sodium chloride.

Example 2

To further characterize the stabilizing effect that sodium chloride has on IgG compositions formulated at mildly acid to neutral pH, an accelerated stability study was performed. For the accelerated study, elevated temperatures (38° C. to 42° C.) were used to simulate longer time periods at room temperature (20° C. to 25° C.). Briefly, a 20% IgG composition, prepared as in Example 1, was divided into samples that were formulated with increasing salt concentrations (0 mM, 50 mM, 100 mM, and 150 mM) at mildly acid to neutral pHs (pH 5.5, 6.0, 6.5, 7.0, and 7.5). The aqueous formulations were then stored at between 38° C. and 42° C. for 6 months. After the 6 month incubation period, the molecular size distribution of IgG in the various formulations were investigated by high performance size exclusion chromatography (HP-SEC). The percentage of IgG aggregates present in the various formulations is shown in FIG. 1.

As seen in FIG. 1, the stability of the immunoglobulin preparation is dependent upon both the pH and the salt concentration of the formulation. Addition of 100 mM or 150 mM sodium chloride in the formulation provided additional stability, as compared to the protective effects seen for 50 mM sodium chloride in Example 1, at pHs between 6.0 and 7.5.

Significantly, inclusion of 150 mM sodium chloride in of IgG compositions formulates at pHs between 6.0 and 7.5 reduced IgG aggregation by more than 50% on average. Optimal stabilization was seen in formulations containing 150 mM sodium chloride at pH 6.5, in which aggregate formation was reduced more than 50% as compared to formulations with 50 mM sodium chloride and about 60% as compared to formulations with no sodium chloride. Consistent with previous observations, the addition of sodium chloride in IgG formulations at lower pH (5.5) results in a destabilizing effect.

Example 3

Preparation of Samples for Study IGSC73

Hizentra® (20% Immune Globulin Subcutaneous (Human); CSL Behring) is a 20% immunoglobulin preparation for subcutaneous administration. This product is formulated at low pH (pH 4.8) employing proline as a stabilizer. Several reports have indicated that the use of proline as a stabilizer for immunoglobulin solutions is superior to the use of glycine or histidine (Maeder et al., Biologicals. 2011 January; 39(1):43-9; Bolli et al., Biologicals. 2010 January; 38(1):150-7).

The purpose of this study is to compare the stability of 20% immunoglobulin formulations using 0.25 M glycine, 0.25 M proline, or 0.25 M histidine. The liquid formulations were incubated at 28° C. to 32° C. and 38° C. to 42° C. for up to one year under air, nitrogen, or argon atmosphere.

In the first experiment (IGSC73) three Gammagard Liquid final containers (prepared from pooled plasma according to the Gammagard Liquid process outlined in Teschner et al. (Vox Sang. 2007 January; 92(1):42-55)) with lot numbers P00809NG, P00909NG, and P01009NG were pooled and the pH adjusted to 4.5 to 4.8. The composition of the starting material lots is provided in Table 4. The parameters of lot P00409NG are also shown in this table as this lot was used in other experiments described below.

TABLE 4

Compositions of starting IgG immunoglobulin lots.

| | P00409NG FC | P00809NG FC | P00909NG FC | P01009NG FC |
|---|---|---|---|---|
| Protein (g/l) | 10.6196 | 10.6431 | 11.8626 | 11.1902 |
| IgA (%) | 0.0029 | 0.0027 | 0.0032 | 0.003 |

TABLE 4-continued

Compositions of starting IgG immunoglobulin lots.

|  |  | P00409NG FC | P00809NG FC | P00909NG FC | P01009NG FC |
|---|---|---|---|---|---|
| MSD (HPLC) | Aggregates | 0.0499 | 0.0938 | 0.0413 | 0.0385 |
| (% area) | Oligo/Dimers | 8.8804 | 7.9121 | 8.2818 | 8.4671 |
|  | Monomers | 90.9821 | 91.9354 | 91.6040 | 91.4253 |
|  | Fragments | 0.0876 | 0.1052 | 0.0730 | 0.0691 |
| Amidolytic Activity (nmol/ml · min) |  | <10 | <10 | <10 | <10 |

The pool was then split into three parts of 500 mL each to formulate the preparation at 20% protein in glycine, histidine, or proline. For the formulation containing glycine, the immunoglobulin pool was just concentrated to 20% using an ultra-/diafiltration device equipped with a 0.2 m² polyethersulfone membrane (Pellicon Mini 30K B-30V). To prepare the proline and histidine formulations, the pool aliquots were diafiltered ten times at a protein concentration of 5% against either 0.25 M proline (pH 4.8) or 0.25 M histidine (pH 6.0) prior to concentrating the samples to 20% protein using an ultra-/diafiltration device equipped with a 0.2 m² polyethersulfone membrane (Pellicon Mini 30K B-30V). The molecular size distribution (MSD) of the 20% formulations after ultra-/diafiltration is provided in Table 5. The data demonstrate that the ultra-/diafiltration steps do not drastically alter the molecular size distribution of the immunoglobulin preparations. Use of proline as a stabilizer appears to have an aggregation enhancing effect. All of the formulations were then sterile filtered using a Millipak 20 (Millipore), aliquoted into vials under and air atmosphere, and closed with stoppers suitable for lyophilization. A total of 18 vials were prepared as described in Table 6 and Table 7.

TABLE 5

Molecular size distribution of the three amino acid formulations (IGSC73) after buffer exchange and concentration to 20%.

|  |  | Proline | Histidine | Glycine |
|---|---|---|---|---|
| MSD (HPLC) | Aggregates | 0.48 | 0.11 | 0.15 |
| (% area) | Oligo/Dimers | 8.96 | 10.82 | 9.04 |
|  | Monomers | 90.25 | 88.80 | 90.52 |
|  | Fragments | 0.31 | 0.27 | 0.29 |

TABLE 6

Variation of amino acid and pH in each formulation.

|  | Sample Identification | | |
|---|---|---|---|
|  | 1F | 2F | 3F |
| Amino Acid | Proline | Histidine | Glycine |
| pH | 4.8 | 6.1 | 4.8 |

TABLE 6-continued

Variation of amino acid and pH in each formulation.

|  | Sample Identification | | |
|---|---|---|---|
|  | 1F | 2F | 3F |
| Tween 80 concentration (mg/L) | 0 | 0 | 0 |
| Atmosphere | Air | Air | Air |

TABLE 7

Variation of atmosphere used for storage.

|  | Sample Identification | | | | | |
|---|---|---|---|---|---|---|
|  | 4F | 5F | 6F | 7F | 8F | 9F |
| Amino acid | Proline | Histidine | Glycine | Proline | Histidine | Glycine |
| pH | 4.8 | 6.1 | 4.8 | 4.8 | 6.1 | 4.8 |
| Tween 80 concentration (mg/L) | 0 | 0 | 0 | 0 | 0 | 0 |
| Atmosphere | N2 | N2 | N2 | Argon | Argon | Argon |

*Samples with the identification numbers 10F through 18F correspond to the formulations 1F to 9F, but are stored under light exposure at 38° C. to 42° C.

Example 4
Study IGSC73—Normal Atmosphere; 28° C. to 32° C.

To determine the stabilizing effect of each amino acid formulation, samples 1F, 2F, and 3F, formulated without polysorbate 80 and stored under air, were stored between 28° C. to 32° C. protected from light for up to one year. The molecular size distribution of the samples were determined after 1, 3, 6, and 12 months. As seen in Table 8, the level of immunoglobulin aggregates in samples formulated with histidine at pH 6.1 was significantly depressed as compared to the proline and glycine formulations. Slightly lower levels of immunoglobulin fragmentation were observed in the histidine formulations as compared to the other two samples.

TABLE 8

Mass size distribution of formulations (IGSC73) stored under normal atmosphere at 28° C. to 32° C.

|  |  |  |  |  | MSD (HPLC) | | | |
|---|---|---|---|---|---|---|---|---|
|  |  | Sample Code | T (° C.) |  | Aggregates % area | Oligo/Dimers % area | Monomers % area | Fragments % area |
| Proline | Air | 1F | Start | 2-8 | 0.48 | 8.96 | 90.25 | 0.31 |
| pH 4.8 |  | 1F | 1 M | 28-32 | 0.56 | 9.78 | 89.17 | 0.49 |

TABLE 8-continued

Mass size distribution of formulations (IGSC73) stored under normal atmosphere at 28° C. to 32° C.

| | | | | MSD (HPLC) | | | |
|---|---|---|---|---|---|---|---|
| | Sample Code | T (° C.) | | Aggregates % area | Oligo/Dimers % area | Monomers % area | Fragments % area |
| | 1F | 3 M | 28-32 | 0.62 | 9.83 | 88.85 | 0.70 |
| | 1F | 6 M | 28-32 | 1.01 | 11.58 | 85.88 | 1.53 |
| | 1F | 12 M | 28-32 | 1.45 | 11.62 | 84.84 | 2.10 |
| Histidine | 2F | Start | 2-8 | 0.11 | 10.82 | 88.8 | 0.27 |
| pH 6.1 | 2F | 1 M | 28-32 | 0.20 | 12.44 | 86.96 | 0.41 |
| | 2F | 3 M | 28-32 | 0.26 | 12.58 | 86.44 | 0.72 |
| | 2F | 6 M | 28-32 | 0.45 | 13.79 | 84.36 | 1.39 |
| | 2F | 12 M | 28-32 | 0.96 | 13.10 | 83.99 | 1.95 |
| Glycine | 3F | Start | 2-8 | 0.15 | 9.04 | 90.51 | 0.29 |
| pH 4.8 | 3F | 1 M | 28-32 | 0.22 | 10.54 | 88.77 | 0.47 |
| | 3F | 3 M | 28-32 | 0.39 | 10.61 | 88.19 | 0.81 |
| | 3F | 6 M | 28-32 | 0.75 | 12.61 | 85.15 | 1.48 |
| | 3F | 12 M | 28-32 | 1.41 | 12.58 | 83.88 | 2.14 |

Example 5

Study IGSC73—Nitrogen Atmosphere; 28° C. to 32° C.

To determine the stabilizing effect of each amino acid formulation, samples 4F, 5F, and 6F, formulated without polysorbate 80 and stored under nitrogen, were stored between 28° C. to 32° C. protected from light for up to one year. The molecular size distribution of the samples were determined after 1, 3, 6, and 12 months. As seen in Table 9, storage of the samples under nitrogen reduced the level of immunoglobulin aggregation in the proline and glycine formulated samples by 14% and 28%, respectively, as compared to samples 1F and 3F stored under normal atmosphere for 12 months. Notably, storage of the histidine formulation under nitrogen reduced the level of immunoglobulin aggregation by nearly 50% as compared to sample 2F stored under normal atmosphere for 12 months. Significantly, the level of immunoglobulin aggregation in the histidine-formulated sample stored under nitrogen (5F) was less than half of the levels of aggregation for the similarly stored proline and glycine formulations (4F and 6F, respectively) Even more interestingly, the level of immunoglobulin fragmentation in the histidine formulation stored under nitrogen was lowered as compared to the histidine formulated sample stored under air. The fragmentation levels of the proline and glycine formulations were not affected by storage under nitrogen.

TABLE 9

Mass size distribution of formulations (IGSC73) stored under nitrogen at 28° C. to 32° C.

| | | | | | MSD (HPLC) | | | |
|---|---|---|---|---|---|---|---|---|
| | | Sample Code | | T (° C.) | Aggregates % area | Oligo/Dimers % area | Monomers % area | Fragments % area |
| Proline | Nitrogen | 4F | Start | 2-8 | 0.48 | 9.04 | 90.15 | 0.33 |
| pH 4.8 | | 4F | 1 M | 28-32 | 0.56 | 10.00 | 88.96 | 0.49 |
| | | 4F | 3 M | 28-32 | 0.63 | 10.05 | 88.49 | 0.84 |
| | | 4F | 6 M | 28-32 | 0.87 | 11.71 | 85.9 | 1.52 |
| | | 4F | 12 M | 28-32 | 1.24 | 11.47 | 85.18 | 2.11 |
| Histidine | | 5F | Start | 2-8 | 0.11 | 10.76 | 88.89 | 0.24 |
| pH 6.1 | | 5F | 1 M | 28-32 | 0.20 | 12.40 | 87.06 | 0.35 |
| | | 5F | 3 M | 28-32 | 0.21 | 12.40 | 86.8 | 0.59 |
| | | 5F | 6 M | 28-32 | 0.33 | 14.10 | 84.38 | 1.19 |
| | | 5F | 12 M | 28-32 | 0.49 | 13.28 | 84.55 | 1.67 |
| Glycine | | 6F | Start | 2-8 | 0.17 | 9.36 | 90.2 | 0.27 |
| pH 4.8 | | 6F | 1 M | 28-32 | 0.27 | 10.32 | 88.95 | 0.46 |
| | | 6F | 3 M | 28-32 | 0.35 | 10.71 | 88.13 | 0.82 |
| | | 6F | 6 M | 28-32 | 0.60 | 12.47 | 85.46 | 1.46 |
| | | 6F | 12 M | 28-32 | 1.02 | 11.93 | 84.87 | 2.17 |

Example 6

Study IGSC73—Argon Atmosphere; 28° C. to 32° C.

To determine the stabilizing effect of each amino acid formulation, samples 7F, 8F, and 9F, formulated without polysorbate 80 and stored under argon, were stored between 28° C. to 32° C. protected from light for up to one year. The molecular size distribution of the samples were determined after 1, 3, 6, and 12 months. As seen for the formulations stored under nitrogen, storage of the proline and glycine formulations under argon resulted in a less than 30% reduction in the level of immunoglobulin aggregates, as compared to samples 1F and 3F stored under normal atmosphere for 12 months (Table 10). Likewise, storage of the histidine formulation under argon reduced the level of immunoglobulin aggregation by 50% as compared to sample 2F stored under normal atmosphere for 12 months. Again, the level of immunoglobulin aggregation in the histidine-formulated sample stored under argon (8F) was less than half of the levels of aggregation for the similarly stored proline and glycine formulations (7F and 9F, respectively). Similarly, the level of immunoglobulin fragmentation in the histidine formulation stored under argon was again lowered as compared to the histidine formulated sample stored under air. The fragmentation levels of the proline and glycine formulations were again not affected by storage under argon.

TABLE 10

Mass size distribution of formulations (IGSC73) stored under argon at 28° C. to 32° C.

| | | Sample Code | | T (° C.) | MSD (HPLC) | | | |
|---|---|---|---|---|---|---|---|---|
| | | | | | Aggregates % area | Oligo/Dimers % area | Monomers % area | Fragments % area |
| Proline pH 4.8 | Argon | 7F | Start | 2-8 | 0.48 | 9.12 | 90.09 | 0.31 |
| | | 7F | 1 M | 28-32 | 0.56 | 10.00 | 88.95 | 0.50 |
| | | 7F | 3 M | 28-32 | 0.59 | 10.17 | 88.32 | 0.91 |
| | | 7F | 6 M | 28-32 | 0.90 | 11.96 | 85.60 | 1.54 |
| | | 7F | 12 M | 28-32 | 1.39 | 11.67 | 84.82 | 2.12 |
| Histidine pH 6.1 | | 8F | Start | 2-8 | 0.12 | 10.71 | 88.91 | 0.26 |
| | | 8F | 1 M | 28-32 | 0.20 | 12.43 | 87.04 | 0.33 |
| | | 8F | 3 M | 28-32 | 0.25 | 12.25 | 86.77 | 0.72 |
| | | 8F | 6 M | 28-32 | 0.34 | 13.97 | 84.44 | 1.25 |
| | | 8F | 12 M | 28-32 | 0.48 | 13.09 | 84.79 | 1.63 |
| Glycine pH 4.8 | | 9F | Start | 2-8 | 0.17 | 9.46 | 90.13 | 0.25 |
| | | 9F | 1 M | 28-32 | 0.26 | 10.45 | 88.83 | 0.46 |
| | | 9F | 3 M | 28-32 | 0.35 | 10.78 | 88.01 | 0.85 |
| | | 9F | 6 M | 28-32 | 0.59 | 12.35 | 85.60 | 1.47 |
| | | 9F | 12 M | 28-32 | 1.03 | 11.90 | 84.90 | 2.18 |

Example 7

Study IGSC73—Normal Atmosphere; 38° C. to 42° C.

To determine the stabilizing effect of each amino acid formulation under more stressful conditions, samples 10F, 11F, and 12F, formulated without polysorbate 80 and stored under air, were stored between 38° C. to 42° C. protected from light for up to five weeks. The molecular size distribution of the samples was determined after 1, 2, and 5 weeks. As seen in Table 11, the level of immunoglobulin aggregates in samples formulated with histidine at pH 6.1 was significantly depressed as compared to the proline and glycine formulations. Slightly lower levels of immunoglobulin fragmentation were observed in the histidine formulations as compared to the other two samples.

TABLE 11

Mass size distribution of formulations (IGSC73) stored under normal atmosphere at 38° C. to 42° C.

| | | Sample Code | | T (° C.) | MSD (HPLC) | | | |
|---|---|---|---|---|---|---|---|---|
| | | | | | Aggregates % area | Oligo/Dimers % area | Monomers % area | Fragments % area |
| Proline pH 4.8 | Air | 10F = 1F | Start | 2-8 | 0.48 | 8.96 | 90.25 | 0.31 |
| | | 10F | 1 W | 38-42 | 2.14 | 7.78 | 89.48 | 0.60 |
| | | 10F | 2 W | 38-42 | 3.14 | 7.35 | 88.79 | 0.71 |
| | | 10F | 4 W* | 38-42 | 4.84 | 7.91 | 86.13 | 1.12 |

TABLE 11-continued

Mass size distribution of formulations (IGSC73) stored under normal atmosphere at 38° C. to 42° C.

| | Sample Code | | T (° C.) | MSD (HPLC) | | | |
| --- | --- | --- | --- | --- | --- | --- | --- |
| | | | | Aggregates % area | Oligo/Dimers % area | Monomers % area | Fragments % area |
| Histidine pH 6.1 | 11F = 2F | Start | 2-8 | 0.11 | 10.82 | 88.8 | 0.27 |
| | 11F | 1 W | 38-42 | 0.45 | 10.04 | 89.01 | 0.50 |
| | 11F | 2 W | 38-42 | 0.70 | 8.39 | 90.41 | 0.49 |
| | 11F | 4 W* | 38-42 | 1.42 | 10.18 | 87.41 | 0.99 |
| Glycine pH 4.8 | 12F = 3F | Start | 2-8 | 0.15 | 9.04 | 90.51 | 0.29 |
| | 12F | 1 W | 38-42 | 1.64 | 8.35 | 89.48 | 0.53 |
| | 12F | 2 W | 38-42 | 2.32 | 7.67 | 89.42 | 0.59 |
| | 12F | 4 W* | 38-42 | 4.24 | 8.74 | 85.88 | 1.14 |

*MSD was measured after five weeks of incubation for these samples.

Example 8

Study IGSC73—Nitrogen Atmosphere; 38° C. to 42° C.

To determine the stabilizing effect of each amino acid formulation under more stressful conditions, samples 13F, 14F, and 15F, formulated without polysorbate 80 and stored under nitrogen, were stored between 38° C. to 42° C. protected from light for up to four weeks. The molecular size distributions of the samples were determined after 1, 2, and 4 weeks. As seen in Table 12, storage of the samples under nitrogen reduced the level of immunoglobulin aggregation in the proline and histidine, but not the glycine formulated samples, as compared to samples stored under normal atmosphere (compare Table 11 and Table 12 at 2 weeks). Significantly, the level of immunoglobulin aggregation in the histidine-formulated sample stored under nitrogen (14F) was less than a third of the levels of aggregation for the similarly stored proline and glycine formulations (13F and 15F, respectively) The fragmentation levels of the proline and histidine formulations were not affected by storage under nitrogen, while a slight increase in the amount of immunoglobulin fragmentation was seen in the glycine formulation.

Example 9

Study IGSC73—Argon Atmosphere; 38° C. to 42° C.

To determine the stabilizing effect of each amino acid formulation under more stressful conditions, samples 16F, 17F, and 18F, formulated without polysorbate 80 and stored under argon, were stored between 38° C. to 42° C. protected from light for up to four weeks. The molecular size distribution of the samples were determined after 1, 2, and 4 weeks. As seen in Table 13, storage of all three formulations under argon resulted in a slight reduction in the level of immunoglobulin aggregates, as compared to samples stored under normal atmosphere for 12 months. As seen for the samples stored under nitrogen, the level of immunoglobulin aggregation in the histidine-formulated sample stored under argon (17F) was less than a third of the levels of aggregation for the similarly stored proline and glycine formulations (16F and 18F, respectively). The level of immunoglobulin fragmentation in the histidine formulation stored under argon was again lowered as compared to the histidine formulated sample stored under air. The fragmentation levels of the proline and glycine formulations were slightly increased as compared to those stored under normal atmosphere.

TABLE 12

Mass size distribution of formulations (IGSC73) stored under nitrogen at 38° C. to 42° C.

| | | Sample Code | | T (° C.) | MSD (HPLC) | | | |
| --- | --- | --- | --- | --- | --- | --- | --- | --- |
| | | | | | Aggregates % area | Oligo/Dimers % area | Monomers % area | Fragments % area |
| Proline pH 4.8 | Nitrogen | 13F = 4F | Start | 2-8 | 0.48 | 9.04 | 90.15 | 0.33 |
| | | 13F | 1 W | 38-42 | 2.09 | 7.96 | 89.37 | 0.58 |
| | | 13F | 2 W | 38-42 | 2.80 | 7.30 | 89.17 | 0.73 |
| | | 13F | 4 W | 38-42 | 4.49 | 7.83 | 86.56 | 1.12 |
| Histidine pH 6.1 | | 14F = 5F | Start | 2-8 | 0.11 | 10.76 | 88.89 | 0.24 |
| | | 14F | 1 W | 38-42 | 0.45 | 10.07 | 88.99 | 0.50 |
| | | 14F | 2 W | 38-42 | 0.64 | 8.51 | 90.37 | 0.48 |
| | | 14F | 4 W | 38-42 | 1.20 | 10.27 | 87.81 | 0.72 |
| Glycine pH 4.8 | | 15F = 6F | Start | 2-8 | 0.17 | 9.36 | 90.2 | 0.27 |
| | | 15F | 1 W | 38-42 | 1.53 | 8.35 | 89.65 | 0.47 |
| | | 15F | 2 W | 38-42 | 2.38 | 7.57 | 89.32 | 0.73 |
| | | 15F | 4 W | 38-42 | 3.87 | 8.37 | 86.62 | 1.14 |

TABLE 13

Mass size distribution of formulations (IGSC73) stored under argon at 38° C. to 42° C.

| | | | | MSD (HPLC) | | | |
|---|---|---|---|---|---|---|---|
| | | Sample Code | T (° C.) | Aggregates % area | Oligo/Dimers % area | Monomers % area | Fragments % area |
| Proline pH 4.8 | Argon | 16F = 7F | Start 2-8 | 0.48 | 9.12 | 90.09 | 0.31 |
| | | 16F | 1 W 38-42 | 2.09 | 8.04 | 89.28 | 0.6 |
| | | 16F | 2 W 38-42 | 2.92 | 7.43 | 88.89 | 0.77 |
| | | 16F | 4 W 38-42 | 4.64 | 7.96 | 86.26 | 1.14 |
| Histidine pH 6.1 | | 17F = 8F | Start 2-8 | 0.12 | 10.71 | 88.91 | 0.26 |
| | | 17F | 1 W 38-42 | 0.45 | 10.31 | 88.86 | 0.38 |
| | | 17F | 2 W 38-42 | 0.67 | 8.63 | 90.27 | 0.42 |
| | | 17F | 4 W 38-42 | 1.24 | 10.24 | 87.77 | 0.74 |
| Glycine pH 4.8 | | 18F = 9F | Start 2-8 | 0.17 | 9.46 | 90.13 | 0.25 |
| | | 18F | 1 W 38-42 | 1.68 | 8.57 | 89.26 | 0.49 |
| | | 18F | 2 W 38-42 | 2.45 | 7.58 | 89.36 | 0.62 |
| | | 18F | 4 W 38-42 | 4.06 | 8.44 | 86.38 | 1.12 |

Example 10

Study IGSC73—Optical Density; 38° C. to 42° C.

To determine the effect of each amino acid formulation on the discoloration of the immunoglobulin composition, the optical density (OD) of each sample was monitored at 350 nm for samples stored under normal atmosphere, nitrogen, and argon at 28° C. to 32° C. for up to 12 months. As disclosed in the literature, the OD values for all readings, except those taken at time 0, have been corrected by the OD at 500 nm to account for air trapped in the highly concentrated solution.

Figure 2A:
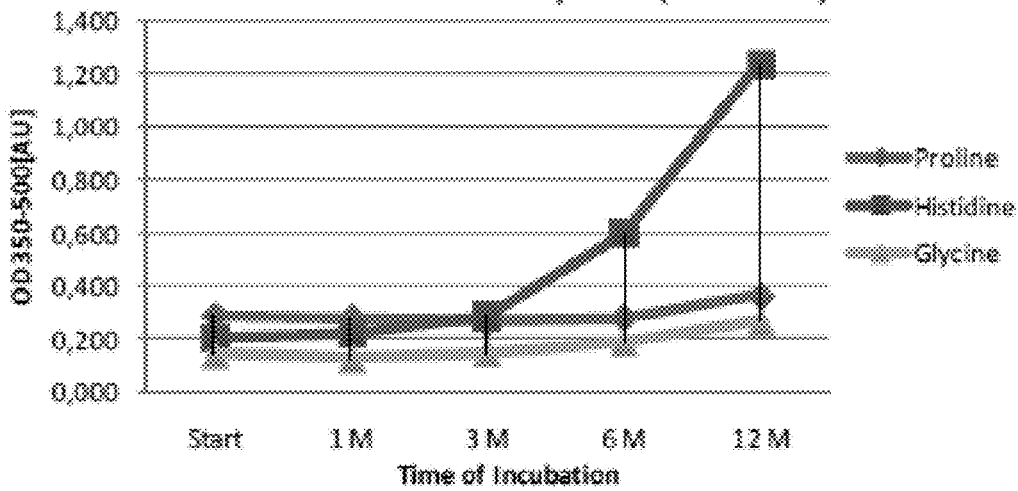
FIG. 2. Discoloration of immunoglobulin compositions from study IGSC73 formulated with proline, histidine (pH 6.1), or glycine and stored at 28° C. to 32° C. under (2A) normal atmosphere, (2B) nitrogen, or (2C) argon for up to 12 months.
Figure 2B:
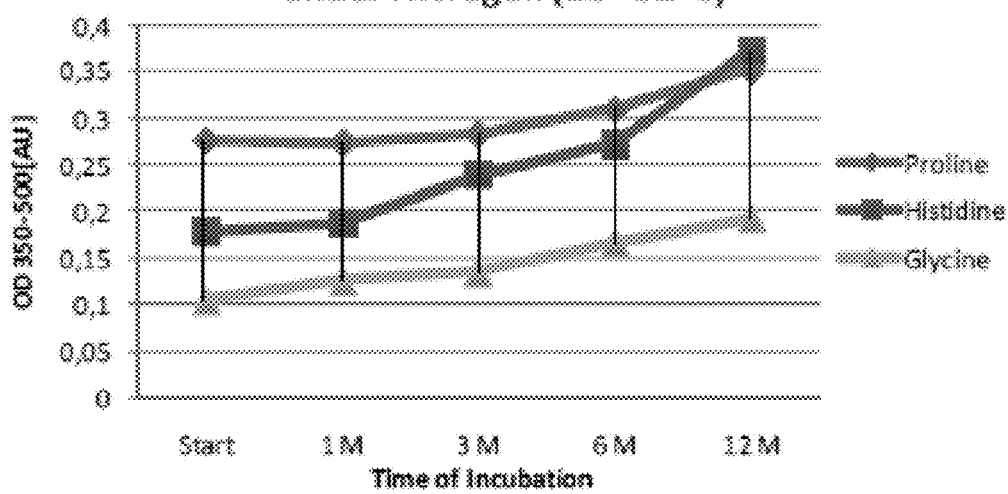
Figure 2C:
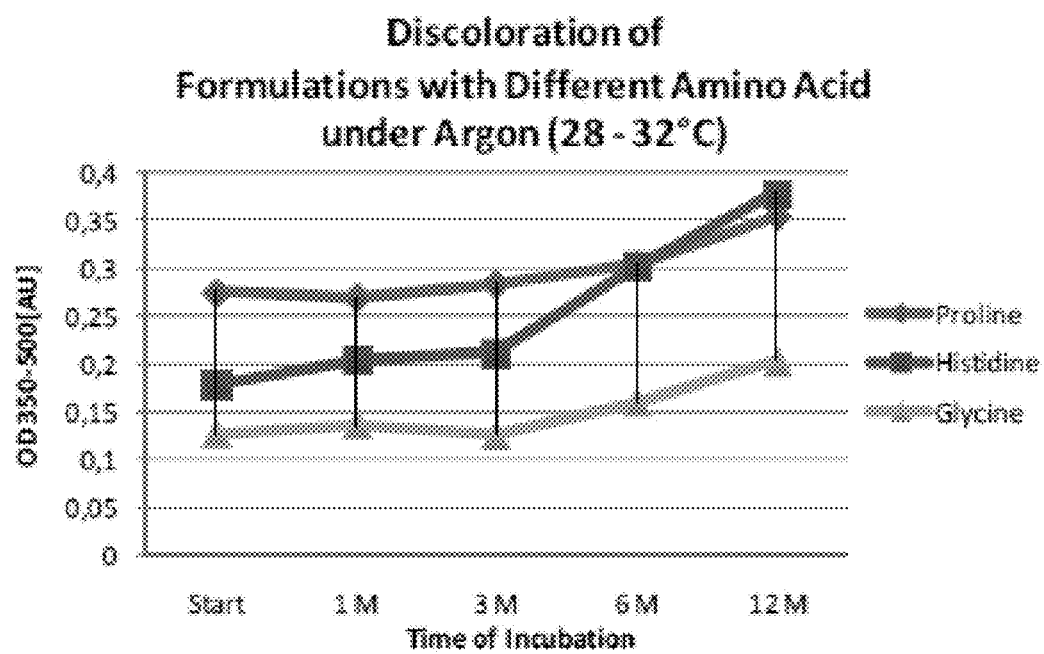

As evidenced in FIGS. 2A, 2B, and 2C, the histidine formulation at pH 6.1 (■) starts to develop a strong discoloration after three months under normal-atmosphere. However, the use of inert gas significantly protects the histidine formulation from this discoloration.

Example 11

Preparation of Samples for Study IGSC74

Sample formulation for study IGSC74 was performed as for study IGSC73, described in Example 3, except for the following changes: i.) four Gammagard Liquid final containers (prepared from pooled plasma according to the Gammagard Liquid process outlined in Teschner et al. (Vox Sang. 2007 January; 92(1):42-55)) with lot numbers P00409NG, P00809NG, P00909NG, and P01009NG were pooled and the pH adjusted to 4.5 to 4.8; and ii.) the sample stabilized with histidine was formulated at pH 4.8, rather than 6.1. Samples were numbered as for study IGSC73 in Example 3 (1F to 18F).

The molecular size distribution (MSD) of the 20% formulations after ultra-/diafiltration is provided in Table 14 The data again demonstrate that the ultra-/diafiltration steps did not drastically alter the molecular size distribution of the immunoglobulin preparations. Similarly, the use of proline as a stabilizer again appeared to have an aggregation enhancing effect.

TABLE 14

Molecular size distribution of the three amino acid formulations (IGSC74) after buffer exchange and concentration to 20%.

| | | Proline | Histidine | Glycine |
|---|---|---|---|---|
| MSD (HPLC) (% area) | Aggregates | 0.46 | 0.10 | 0.11 |
| | Oligo/Dimers | 7.22 | 6.53 | 7.26 |
| | Monomers | 92.02 | 93.14 | 92.33 |
| | Fragments | 0.30 | 0.23 | 0.30 |

Example 12

Study IGSC74—Normal Atmosphere; 28° C. to 32° C.

To determine the stabilizing effect of each amino acid formulation, samples 1F, 2F, and 3F, formulated without polysorbate 80 and stored under air, were stored between 28° C. to 32° C. protected from light for up to one year. The molecular size distributions of the samples were determined after 1, 3, 6, and 12 months. As seen in Table 15, the histidine formulation at pH 4.8 had significantly higher levels of immunoglobulin aggregates and fragments after storage for 12 months, as compared to the proline and glycine formulations. This is in stark contrast to the immunoglobulin compositions formulated with histidine at pH 6.1, which displayed increased stability over time as compared to the proline and glycine formulations. Notably, the level of immunoglobulin aggregation and fragmentation of the proline and glycine formulations was nearly identical for study IGSC73 and IGSC74.

TABLE 15

Mass size distribution of formulations (IGSC74) stored under normal atmosphere at 28° C. to 32° C.

| | | Sample Code | T (° C.) | Aggregates % area | Oligo/Dimers % area | Monomers % area | Fragments % area |
|---|---|---|---|---|---|---|---|
| Proline | Air | 1F Start | 2-8 | 0.46 | 7.22 | 92.02 | 0.30 |
| pH 4.8 | | 1F 1 M | 28-32 | 0.54 | 10.63 | 88.39 | 0.45 |
| | | 1F 3 M | 28-32 | 0.62 | 11.10 | 87.53 | 0.75 |
| | | 1F 6 M | 28-32 | 0.88 | 11.82 | 85.77 | 1.53 |
| | | 1F 12 M | 28-32 | 1.41 | 11.21 | 85.35 | 2.02 |
| Histidine | | 2F Start | 2-8 | 0.10 | 6.53 | 93.14 | 0.23 |
| pH 4.8 | | 2F 1 M | 28-32 | 0.79 | 9.15 | 89.56 | 0.51 |
| | | 2F 3 M | 28-32 | 1.57 | 9.67 | 87.7 | 1.07 |
| | | 2F 6 M | 28-32 | 2.68 | 10.09 | 85.42 | 1.81 |
| | | 2F 12 M | 28-32 | 5.04 | 9.14 | 83.14 | 2.68 |
| Glycine | | 3F Start | 2-8 | 0.11 | 7.26 | 92.33 | 0.30 |
| pH 4.8 | | 3F 1 M | 28-32 | 0.24 | 10.96 | 88.33 | 0.46 |
| | | 3F 3 M | 28-32 | 0.36 | 11.62 | 87.24 | 0.77 |
| | | 3F 6 M | 28-32 | 0.71 | 12.61 | 85.14 | 1.54 |
| | | 3F 12 M | 28-32 | 1.36 | 12.42 | 84.09 | 2.14 |

Example 13

Study IGSC74—Nitrogen Atmosphere; 28° C. to 32° C.

To determine the stabilizing effect of each amino acid formulation, samples 4F, 5F, and 6F, formulated without polysorbate 80 and stored under nitrogen, were stored between 28° C. to 32° C. protected from light for up to one year. The molecular size distributions of the samples were determined after 1, 3, 6, and 12 Months. As for the formulations stored under normal atmosphere, the histidine formulation at pH 4.8 had significantly higher levels of immunoglobulin aggregates and fragments after storage for 12 months, as compared to the proline and glycine formulations (Table 16). The level of immunoglobulin aggregation and fragmentation of the proline and glycine formulations stored under nitrogen was very similar for study IGSC73 and IGSC74.

Example 14

Study IGSC74—Argon Atmosphere; 28° C. to 32° C.

To determine the stabilizing effect of each amino acid formulation, samples 7F, 8F, and 9F, formulated without polysorbate 80 and stored under argon, were stored between 28° C. to 32° C. protected from light for up to one year. The molecular size distributions of the samples were determined after 1, 3, 6, and 12 months. As for the formulations stored under normal atmosphere and nitrogen, the histidine formulation at pH 4.8 had significantly higher levels of immunoglobulin aggregates and fragments after storage for 12 months, as compared to the proline and glycine formulations (Table 17). The level of immunoglobulin aggregation and fragmentation of the proline and glycine formulations stored under argon was similar for study IGSC73 and IGSC74.

TABLE 16

Mass size distribution of formulations (IGSC74) stored under nitrogen at 28° C. to 32° C.

| | | Sample Code | T (° C.) | Aggregates % area | Oligo/Dimers % area | Monomers % area | Fragments % area |
|---|---|---|---|---|---|---|---|
| Proline | Nitrogen | 4F Start | 2-8 | 0.45 | 7.26 | 91.96 | 0.33 |
| pH 4.8 | | 4F 1 M | 28-32 | 0.51 | 10.48 | 88.61 | 0.40 |
| | | 4F 3 M | 28-32 | 0.58 | 10.76 | 87.83 | 0.84 |
| | | 4F 6 M | 28-32 | 0.79 | 11.77 | 86.01 | 1.44 |
| | | 4F 12 M | 28-32 | 1.10 | 11.11 | 85.77 | 2.02 |
| Histidine | | 5F Start | 2-8 | 0.10 | 6.59 | 93.07 | 0.24 |
| pH 4.8 | | 5F 1 M | 28-32 | 0.70 | 8.92 | 89.9 | 0.47 |
| | | 5F 3 M | 28-32 | 1.41 | 9.43 | 88.07 | 1.09 |
| | | 5F 6 M | 28-32 | 2.45 | 10.03 | 85.7 | 1.83 |
| | | 5F 12 M | 28-32 | 4.44 | 9.19 | 83.62 | 2.74 |
| Glycine | | 6F Start | 2-8 | 0.12 | 7.28 | 92.33 | 0.27 |
| pH 4.8 | | 6F 1 M | 28-32 | 0.23 | 10.96 | 88.32 | 0.48 |
| | | 6F 3 M | 28-32 | 0.35 | 11.56 | 87.38 | 0.72 |
| | | 6F 6 M | 28-32 | 0.57 | 12.36 | 85.58 | 1.49 |
| | | 6F 12 M | 28-32 | 0.98 | 11.83 | 85.07 | 2.12 |

TABLE 17

Mass size distribution of formulations (IGSC74) stored under argon at 28° C. to 32° C.

| | | | | MSD (HPLC) | | | |
|---|---|---|---|---|---|---|---|
| | | Sample Code | T (° C.) | Aggregates % area | Oligo/Dimers % area | Monomers % area | Fragments % area |
| Proline pH 4.8 | Argon | 7F | Start | 2-8 | 0.44 | 7.37 | 91.96 | 0.24 |
| | | 7F | 1 M | 28-32 | 0.51 | 10.48 | 88.59 | 0.42 |
| | | 7F | 3 M | 28-32 | 0.57 | 11.07 | 87.73 | 0.63 |
| | | 7F | 6 M | 28-32 | 0.84 | 12.00 | 85.7 | 1.47 |
| | | 7F | 12 M | 28-32 | 1.22 | 11.26 | 85.51 | 2.00 |
| Histidine pH 4.8 | | 8F | Start | 2-8 | 0.10 | 6.76 | 92.92 | 0.21 |
| | | 8F | 1 M | 28-32 | 0.79 | 8.93 | 89.75 | 0.53 |
| | | 8F | 3 M | 28-32 | 1.58 | 9.74 | 87.66 | 1.03 |
| | | 8F | 6 M | 28-32 | 2.57 | 10.13 | 85.49 | 1.82 |
| | | 8F | 12 M | 28-32 | 4.67 | 9.18 | 83.41 | 2.74 |
| Glycine pH 4.8 | | 9F | Start | 2-8 | 0.11 | 7.61 | 92.01 | 0.27 |
| | | 9F | 1 M | 28-32 | 0.25 | 10.86 | 88.41 | 0.47 |
| | | 9F | 3 M | 28-32 | 0.37 | 11.75 | 87.04 | 0.84 |
| | | 9F | 6 M | 28-32 | 0.71 | 12.7 | 85.03 | 1.55 |
| | | 9F | 12 M | 28-32 | 1.23 | 12.09 | 84.56 | 2.12 |

Example 15

Study IGSC74—Normal Atmosphere; 38° C. to 42° C.

To determine the stabilizing effect of each amino acid formulation under more stressful conditions, samples 10F, 11F, and 12F, formulated without polysorbate 80 and stored under air, were stored between 38° C. to 42° C. protected from light for up to four weeks. The molecular size distributions of the samples were determined after 1, 2, and 4 weeks. As seen in Table 18, histidine formulation at pH 4.8 is not stable at all and the analysis was discontinued after two weeks. In comparison with study IGSC73, the preparations stabilized with glycine and proline show less aggregation. Especially the formulation with proline has only 3.8% aggregates at the end of the study, while in IGSC73 the aggregate content rose to 4.8%. Nevertheless, the proline stabilized immunoglobulin tends more to aggregation than the glycine stabilized IgG. Oligo-/dimer contents are slightly lower in the proline formulation.

Example 16

Study IGSC74—Nitrogen Atmosphere; 38° C. to 42° C.

To determine the stabilizing effect of each amino acid formulation under more stressful conditions, samples 13F, 14F, and 15F, formulated without polysorbate 80 and stored under nitrogen, were stored between 38° C. to 42° C. protected from light for up to four weeks. The molecular size distributions of the samples were determined after 1, 2, and 4 weeks. As seen in Table 19, the histidine formulation shows instability at pH 4.8 even under inert gas. When nitrogen is used as inert gas, again glycine formulated IgG is the most stable. In comparison to proline stabilized IgG, it aggregates less. The oligo-/dimer contents are almost at the same level.

TABLE 18

Mass size distribution of formulations (IGSC73) stored under normal atmosphere at 38° C. to 42° C.

| | | | | | MSD (HPLC) | | | |
|---|---|---|---|---|---|---|---|---|
| | | Probenbezeichnung | | T (° C.) | Aggregate % area | Oligo/Dim. % area | Monomer % area | Fragments % area |
| Proline pH 4.8 | Air | 10F = 1F | Start | 2-8 | 0.46 | 7.22 | 92.02 | 0.30 |
| | | 10F | 1 W | 38-42 | 1.73 | 7.52 | 90.39 | 0.36 |
| | | 10F | 2 W | 38-42 | 2.01 | 8.74 | 88.64 | 0.61 |
| | | 10F | 4 W | 38-42 | 3.83 | 8.28 | 86.99 | 0.91 |
| Histidine pH 4.8 | | 11F = 2F | Start | 2-8 | 0.10 | 6.53 | 93.14 | 0.23 |
| | | 11F | 1 W | 38-42 | 14.68 | 5.57 | 79.14 | 0.61 |
| | | 11F | 2 W | 38-42 | 15.58 | 5.68 | 77.91 | 0.82 |
| | | 11F | 4 W | 38-42 | | | | |
| Glycine pH 4.8 | | 12F = 3F | Start | 2-8 | 0.11 | 7.26 | 92.33 | 0.30 |
| | | 12F | 1 W | 38-42 | 1.34 | 7.85 | 90.44 | 0.38 |
| | | 12F | 2 W | 38-42 | 1.84 | 9.27 | 88.22 | 0.67 |
| | | 12F | 4 W | 38-42 | 3.65 | 8.77 | 86.57 | 1.01 |

TABLE 19

Mass size distribution of formulations (IGSC74) stored under nitrogen at 38° C. to 42° C.

| | | | | MSD (HPLC) | | | |
|---|---|---|---|---|---|---|---|
| | | Sample Code | T (° C.) | Aggregates % area | Oligo/Dimers % area | Monomers % area | Fragments % area |
| Proline pH 4.8 | Nitrogen | 13F = 4F | Start 2-8 | 0.45 | 7.26 | 91.96 | 0.33 |
| | | 13F | 1 W 38-42 | 1.70 | 7.69 | 90.20 | 0.41 |
| | | 13F | 2 W 38-42 | 2.05 | 9.03 | 88.28 | 0.64 |
| | | 13F | 4 W 38-42 | 3.56 | 8.24 | 87.29 | 0.91 |
| Histidine pH 4.8 | | 14F = 5F | Start 2-8 | 0.10 | 6.59 | 93.07 | 0.24 |
| | | 14F | 1 W 38-42 | 14.15 | 5.51 | 79.70 | 0.64 |
| | | 14F | 2 W 38-42 | 16.21 | 5.83 | 77.20 | 0.76 |
| | | 14F | 4 W 38-42 | | | | |
| Glycine pH 4.8 | | 15F = 6F | Start 2-8 | 0.12 | 7.28 | 92.33 | 0.27 |
| | | 15F | 1 W 38-42 | 1.28 | 8.09 | 90.23 | 0.40 |
| | | 15F | 2 W 38-42 | 1.76 | 9.46 | 88.11 | 0.67 |
| | | 15F | 4 W 38-42 | 3.07 | 8.64 | 87.35 | 0.94 |

Example 17

Study IGSC74—Argon Atmosphere; 38° C. to 42° C.

To determine the stabilizing effect of each amino acid formulation under more stressful conditions, samples 16F, 17F, and 18F, formulated without polysorbate 80 and stored under argon, were stored between 38° C. to 42° C. protected from light for up to four weeks. The molecular size distributions of the samples were determined after 1, 2, and 4 weeks. As seen in Table 20, the histidine formulation shows instability at pH 4.8 even under inert gas. With an overlay of argon the formulations with glycine or proline give the same molecular size distribution results as under normal atmosphere.

TABLE 20

Mass size distribution of formulations (IGSC74) stored under argon at 38° C. to 42° C.

| | | | | MSD (HPLC) | | | |
|---|---|---|---|---|---|---|---|
| | | Sample Code | T (° C.) | Aggregates % area | Oligo/Dimers % area | Monomers % area | Fragments % area |
| Proline pH 4.8 | Argon | 16F = 7F | Start 2-8 | 0.44 | 7.37 | 91.96 | 0.24 |
| | | 16F | 1 W 38-42 | 1.68 | 7.69 | 90.25 | 0.38 |
| | | 16F | 2 W 38-42 | 2.19 | 9.08 | 88.03 | 0.70 |
| | | 16F | 4 W 38-42 | 3.53 | 8.31 | 87.23 | 0.93 |
| Histidine pH 4.8 | | 17F = 8F | Start 2-8 | 0.10 | 6.76 | 92.92 | 0.21 |
| | | 17F | 1 W 38-42 | 14.81 | 5.56 | 79.11 | 0.51 |
| | | 17F | 2 W 38-42 | 18.92 | 5.62 | 74.76 | 0.70 |
| | | 17F | 4 W 38-42 | | | | |
| Glycine pH 4.8 | | 18F = 9F | Start 2-8 | 0.11 | 7.61 | 92.01 | 0.27 |
| | | 18F | 1 W 38-42 | 1.33 | 8.3 | 89.91 | 0.46 |
| | | 18F | 2 W 38-42 | 2.07 | 9.52 | 87.77 | 0.65 |
| | | 18F | 4 W 38-42 | 3.57 | 8.89 | 86.53 | 1.01 |

Example 18

Study IGSC73—Optical Density; 38° C. to 42° C.

To determine the effect of each amino acid formulation on the discoloration of the immunoglobulin composition, the optical density (OD) of each sample was monitored at 350 nm for samples stored under normal atmosphere, nitrogen, and argon at 28° C. to 32° C. for up to 12 months. As disclosed in the literature, the OD values for all readings, except those taken at time 0, have been corrected by the OD at 500 nm to account for air trapped in the highly concentrated solution.

Figure 3A:
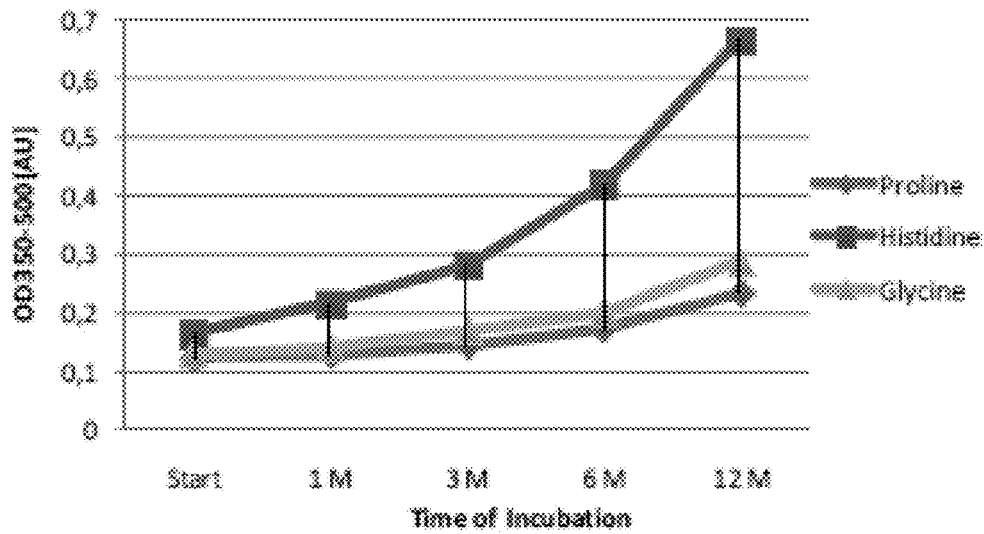
FIG. 3. Discoloration of immunoglobulin compositions from study IGSC74 formulated with proline, histidine (pH 4.8), or glycine and stored at 28° C. to 32° C. under (3A) normal atmosphere, (3B) nitrogen, or (3C) argon for up to 12 months.
Figure 3B:
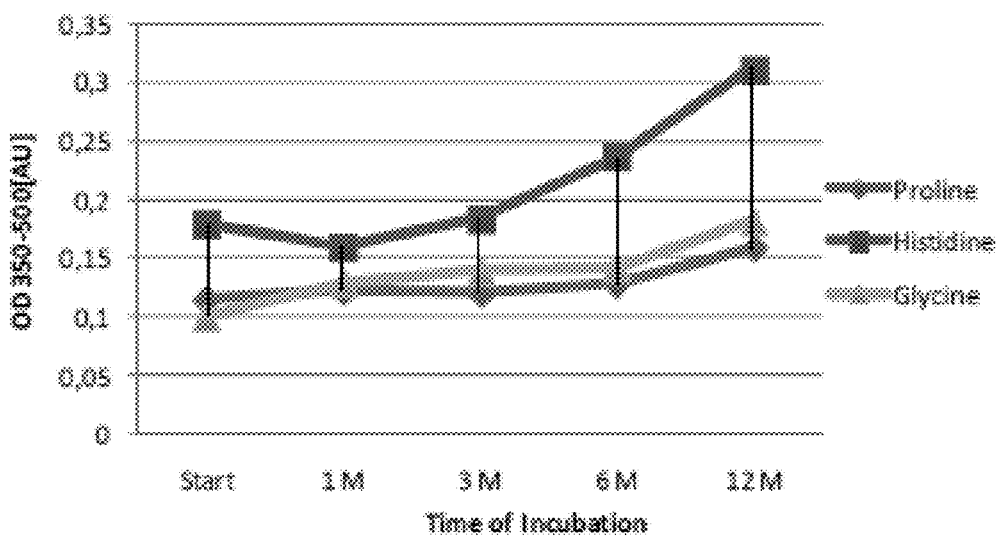
Figure 3C:
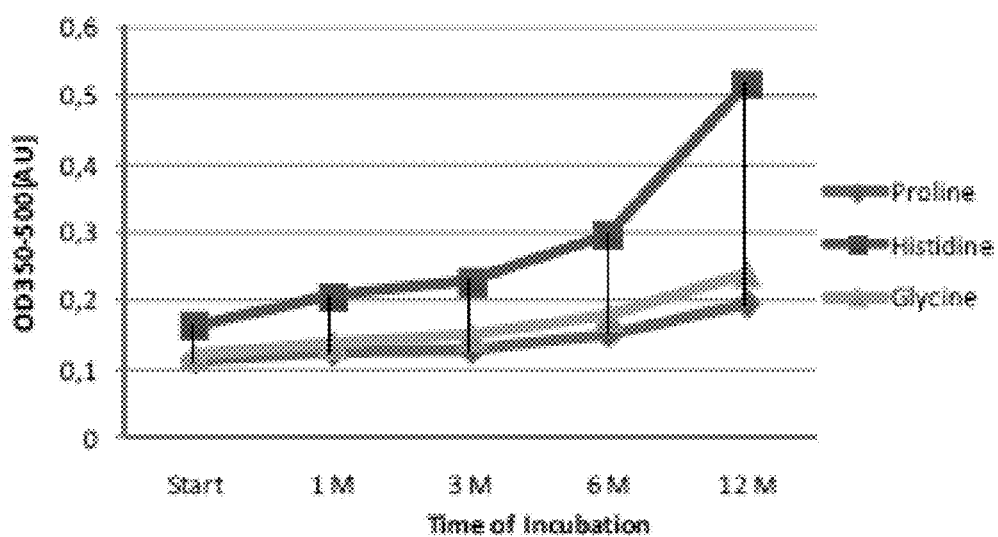

As evidenced in FIGS. 3A, 3B, and 3C, the histidine formulation at pH 4.8 (■) starts to develop a much stronger discoloration after three months under normal atmosphere, but under inert gas the color is only half as intensive. In comparison to the histidine formulation at pH 6.1 the discoloration is less pronounced under normal atmosphere and about the same under inert gas. This confirms the observation that the discoloration is not correlated to the aggregate level. Discoloration under inert gas, especially under nitrogen is also less pronounced for proline and glycine formulated solutions in this study compared to the same formulations under normal atmosphere.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A storage stable, aqueous immunoglobulin composition comprising:
   (a) an immunoglobulin
   (b) from 225 mM to 275 mM histidine;
   (c) from 0 mM to 10 mM of an alkali metal cation; and
   (d) a pH from 5.5 to 7.0,
   wherein the composition is stable for at least 6 months when stored at from 28° C. to 32° C., and wherein the composition is considered stable as long as the percentage of immunoglobulin in the aggregated state remains below 2%, and wherein the composition does not contain a surfactant or sugar.

2. The composition of claim 1, containing from 0 mM to 1 mM of an alkali metal cation.

3. The composition of claim 1, wherein the composition contains from 10 mM to 400 mM chloride ions.

4. The composition of claim 3, containing from 100 mM to 200 mM chloride ions.

5. The composition of claim 1, wherein the pH of the composition is from 5.5 to 6.5.

6. The composition of claim 5, wherein the pH of the composition is 6.1±0.2.

7. The composition of claim 1, wherein the composition further comprises an antioxidant.

8. The composition of claim 1, wherein the composition is stored under an inert gas.

9. The composition of claim 8, wherein the inert gas is selected from the group consisting of nitrogen, argon, carbon dioxide, helium, krypton, and xenon.

10. The composition of claim 8, wherein the inert gas is nitrogen.

11. The composition of claim 8, wherein the inert gas is argon.

12. The composition of claim 1, wherein the immunoglobulin is a polyclonal immunoglobulin.

13. The composition of claim 1, wherein the immunoglobulin is a monoclonal immunoglobulin.

14. The composition of claim 1, wherein the immunoglobulin is an IgG immunoglobulin.

15. The composition of claim 1, wherein the immunoglobulin is enriched from pooled human plasma.

16. The composition of claim 1, wherein the immunoglobulin is a recombinant immunoglobulin.

17. The composition of claim 1, wherein the concentration of the immunoglobulin is 50±5 g/L.

18. The composition of claim 1, wherein the concentration of the immunoglobulin is less than 50 g/L.

19. The composition of claim 1, wherein the concentration of the immunoglobulin is at least 50 g/L.

20. The composition of claim 19, wherein the concentration of the immunoglobulin is from 50 g/L to 150 g/L.

21. The composition of claim 20, wherein the concentration of the immunoglobulin is 100±10 g/L.

22. The composition of claim 19, wherein the concentration of the immunoglobulin is at least 100 g/L.

23. The composition of claim 22, wherein the concentration of the immunoglobulin is 150±15 g/L.

24. The composition of claim 22, wherein the concentration of the immunoglobulin is from 150 g/L to 250 g/L.

25. The composition of claim 24, wherein the concentration of the immunoglobulin is 200±20 g/L.

26. The composition of claim 19, wherein the concentration of the immunoglobulin is at least 200 g/L.

27. The composition of claim 1, wherein the composition is stable for at least 1 month when stored at from 38° C. to 42° C.

28. The composition of claim 27, wherein the composition is stable for at least 3 months when stored at from 38° C. to 42° C.

29. The composition of claim 28, wherein the composition is stable for at least 6 months when stored at from 38° C. to 42° C.

30. The composition of claim 1, wherein the composition is stable for at least 1 year when stored at from 28° C. to 32° C.

31. The composition of claim 30, wherein the composition is stable for at least 2 years when stored at from 28° C. to 32° C.

32. The composition of claim 1, wherein the composition is considered stable as long as the percentage of immunoglobulin in the aggregated state is from 0% to 2% and the percentage of immunoglobulin in the monomeric state is from 85% to 100%.

33. The composition of claim 1, wherein a composition having the same components, but formulated at pH 4.8, is stable for less than 1 month when stored at from 38° C. to 42° C.

34. The composition of claim 1, wherein a composition having the same components, but formulated at pH 4.8, is stable for less than 6 months when stored at from 28° C. to 32° C.

* * * * *